(12) United States Patent
Malamas et al.

(10) Patent No.: US 9,963,444 B2
(45) Date of Patent: May 8, 2018

(54) N-ACYLETHANOLAMINE HYDROLYZING ACID AMIDASE (NAAA) INHIBITORS AND THEIR USE THEREOF

(71) Applicant: Northeastern University, Boston, MA (US)

(72) Inventors: Michael Malamas, Boston, MA (US); Alexandros Makriyannis, Boston, MA (US); Kumara Vadivel Subramanian, Boston, MA (US); Kyle M. Whitten, Boston, MA (US); Nikolai M. Zvonok, Boston, MA (US); Jay Matthew West, Boston, MA (US); Michael Mccormack, Boston, MA (US); Spiro Pavlopoulos, Boston, MA (US)

(73) Assignee: Northeastern University, Boston, MA (US)

( * ) Notice: Subject to any disclaimer, the term of this patent is extended or adjusted under 35 U.S.C. 154(b) by 0 days. days.

(21) Appl. No.: 15/311,817

(22) PCT Filed: May 13, 2015

(86) PCT No.: PCT/US2015/030583
§ 371 (c)(1),
(2) Date: Nov. 16, 2016

(87) PCT Pub. No.: WO2015/179190
PCT Pub. Date: Nov. 26, 2015

(65) Prior Publication Data
US 2017/0114050 A1 Apr. 27, 2017

Related U.S. Application Data

(60) Provisional application No. 62/000,331, filed on May 19, 2014.

(51) Int. Cl.

| | | |
|---|---|---|
| *C07C 255/46* | (2006.01) | |
| *C07D 405/12* | (2006.01) | |
| *C07D 403/12* | (2006.01) | |
| *C07D 317/54* | (2006.01) | |
| *C07D 319/18* | (2006.01) | |
| *C07D 231/12* | (2006.01) | |
| *C07D 401/12* | (2006.01) | |
| *C07D 413/12* | (2006.01) | |
| *C07D 261/08* | (2006.01) | |
| *C07D 205/04* | (2006.01) | |
| *C07D 207/12* | (2006.01) | |

(Continued)

(52) U.S. Cl.
CPC .......... *C07D 405/12* (2013.01); *C07C 255/46* (2013.01); *C07C 331/20* (2013.01); *C07C 331/24* (2013.01); *C07C 331/26* (2013.01); *C07D 205/04* (2013.01); *C07D 207/12* (2013.01); *C07D 211/10* (2013.01); *C07D 211/26* (2013.01); *C07D 211/46* (2013.01); *C07D 213/30* (2013.01); *C07D 213/36* (2013.01); *C07D 213/46* (2013.01); *C07D 213/64* (2013.01); *C07D 231/12* (2013.01); *C07D 239/26* (2013.01); *C07D 239/28* (2013.01); *C07D 241/18* (2013.01); *C07D 261/08* (2013.01); *C07D 295/13* (2013.01); *C07D 295/135* (2013.01); *C07D 317/54* (2013.01); *C07D 317/58* (2013.01); *C07D 319/18* (2013.01); *C07D 401/12* (2013.01); *C07D 403/12* (2013.01); *C07D 413/12* (2013.01); *C07B 2200/07* (2013.01); *C07C 2601/04* (2017.05); *C07C 2601/08* (2017.05); *C07C 2601/14* (2017.05); *C07C 2602/08* (2017.05)

(58) Field of Classification Search
CPC ............................ C07D 405/12; C07C 255/46
USPC ....................................................... 540/360
See application file for complete search history.

(56) References Cited

U.S. PATENT DOCUMENTS

| | | |
|---|---|---|
| 4,001,254 A | 1/1977 | Schmid et al. |
| 6,124,323 A | 9/2000 | Bigge et al. |

(Continued)

FOREIGN PATENT DOCUMENTS

| | | |
|---|---|---|
| KR | 20130122361 A | 11/2013 |

OTHER PUBLICATIONS

PCT/US2015/030583 Written Opinion of the International Searching Authority dated Jul. 29, 2015 entitled "N-Acylethanolamine Hydrolyzing Acid Amidase (NAAA) Inhibitors and Their Use Thereof."

(Continued)

*Primary Examiner* — Kahsay Habte
(74) *Attorney, Agent, or Firm* — Hamilton, Brook, Smith & Reynolds, P.C.

(57) ABSTRACT

A compound is represented as Formula I, a tautomer thereof, a stereoisomer thereof, or a pharmaceutically acceptable salt thereof. Compounds of Formula I are inhibitors of N-acylethanolamine hydrolyzing acid amidase (NAAA). The present technology is directed to compounds, compositions, and methods to inhibit N-acylethanolamine hydrolyzing acid amidase and to treat N-acylethanolamine hydrolyzing acid amidase mediated conditions in a subject.

Formula I

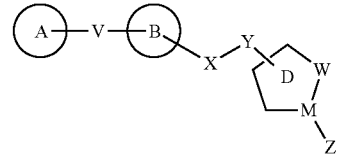

14 Claims, 3 Drawing Sheets

(51) Int. Cl.

| | | |
|---|---|---|
| *C07D 211/10* | (2006.01) | |
| *C07D 211/26* | (2006.01) | |
| *C07D 211/46* | (2006.01) | |
| *C07D 213/46* | (2006.01) | |
| *C07D 213/64* | (2006.01) | |
| *C07C 331/20* | (2006.01) | |
| *C07C 331/24* | (2006.01) | |
| *C07C 331/26* | (2006.01) | |
| *C07D 213/30* | (2006.01) | |
| *C07D 213/36* | (2006.01) | |
| *C07D 239/26* | (2006.01) | |
| *C07D 239/28* | (2006.01) | |
| *C07D 241/18* | (2006.01) | |
| *C07D 295/13* | (2006.01) | |
| *C07D 295/135* | (2006.01) | |
| *C07D 317/58* | (2006.01) | |

(56) References Cited

U.S. PATENT DOCUMENTS

| | | |
|---|---|---|
| 6,835,727 B2 | 12/2004 | Okamoto et al. |
| 7,868,177 B2 | 1/2011 | Cee et al. |
| 2011/0112127 A1 | 5/2011 | Zhang et al. |
| 2014/0094508 A1 | 4/2014 | Piomelli et al. |

OTHER PUBLICATIONS

Whitten, K.M., "Synthesis and Biological Evaluation of Novel Endocannabinoid Probes, Metabolically Stable Analogs, and Nacylethanolamine-Hydrolyzing Acid Amidase Inhibitors,", (2012) Chemistry Dissertations, Paper 56. [retrieved on Jul. 16, 2015] Retrieved from the Internet. <URL: hitp://hdl.handle.net/2047/d20002788>, pp. 2, 3, 7-18, 182-233.

West, et al., "Mass Spectrometric Characterization of Human N-Acylethanolamine-Hydrolyzing Acid Amidase," J. Proteome Res., 11(2): 972-981 (2012).

PCT/US2015/030583 International Search Report dated Jul. 29, 2015 entitled "N-Acylethanolamine Hydrolyzing Acid Amidase (NAAA) Inhibitors and Their Use Thereof."

Notification Concerning Transmittal of International Preliminary Report on Patentability for International Application No. PCT/US2015/030583, "N-Acylethanolamine Hydrolyzing Acid Amidase (NAAA) Inhibitors and Their Use Thereof", dated Nov. 22, 2016.

Supplemental Partial European Search Report for European Application No. 15 79 5556, "N-Acylethanolamine Hydrolyzing Acid Amidase (NAAA) Inhibitors and Their Use Thereof", dated Oct. 12, 2017.

N-ACYLETHANOLAMINE HYDROLYZING ACID AMIDASE (NAAA) INHIBITORS AND THEIR USE THEREOF

CROSS-REFERENCE TO RELATED PATENT APPLICATIONS

This application is the U.S. National Stage of International Application No. PCT/US2015/030583, filed May 13, 2015, which designates the U.S., published in English, and claims the benefit of U.S. Provisional Patent Application No. 62/000,331, filed May 19, 2014. The entire teachings of the above applications are incorporated herein by reference.

GOVERNMENT RIGHTS

The United States Government has rights in this technology pursuant to Contract No. R01-DA003801 awarded by the National Institute of Health.

FIELD

The present technology is directed to compounds, compositions, and methods for inhibiting N-acylethanolamine hydrolyzing acid amidase and for treating N-acylethanolamine hydrolyzing acid amidase mediated conditions in a subject.

BACKGROUND

N-Acylethanolamine-hydrolyzing acid amidase (NAAA) is a lysosomal enzyme, which plays a central role in the deactivation of N-palmitoylethanolamine (PEA) (Chemistry & Biodiversity. 2007; 4: 1914-25). PEA is an endogenous lipid produced on-demand by most mammalian cells (The Journal of biological chemistry. 2004; 279: 5298-305). A growing body of evidence links PEA in the regulation of inflammatory and pain processes. PEA reduces peripheral inflammation (Eur. J Pharmacol. 1996; 300: 227-36; Neuropharmacology. 2005; 48: 1154-63; Gut. 2013) and exerts neuroprotective (Epilepsia 2001; 42: 321-7) and antinociceptive effects (Nature. 1998; 394: 277-81) in rats and mice. Local and systemic administration of PEA alleviated pain behaviors elicited by chemical irritants and was effective even when administered after induction (Pain 1998; 76: 189-99) of acute inflammation (Br. J. Pharmacol. 2002; 137: 413-20). The PEA levels in ulcerative colitis patients were assessed by biopsy of the mast cells (Am. J. Gastroenterol. 2002; 97: 3071-7; Inflamm. Bowel Dis. 2003; 9: 224-9). Mast cells produce high amounts of PEA (The Journal of Biological Chemistry. 1997; 272: 3315-23) that potently inhibit mouse small intestine motility and visceral pain in mice (Br. J. Pharmacol. 2001; 134: 945-50). Thus, the presence of elevated levels of PEA in colonic biopsies strengthens the hypothesis that this compound participates in the control of visceral pain and intestinal motility.

PEA is an endogenous agonist for the peroxisome proliferator-activated receptor-α (PPARα) (Nature. 2003; 425: 90-3; Life Sci. 2005; 77: 1685-98), which is expressed in the intestinal mucosa of the small intestine and colon. Activation of PPARα with endogenous or exogenous ligands resulted in the amelioration of di-nitrobenzene sulfonic acid (DNBS)-induced colitis, suggestive of the potential role of PPARα ligands as novel therapies for GI inflammatory conditions (The Journal of Investigative Dermatology. 2002; 118: 94-101; Laboratory Investigation; a journal of Technical Methods and Pathology. 2004; 84: 1643-54). However, the prolonged clinical use of exogenous PPARα ligands was linked to a variety of severe side-effects, including oncogenesis, renal dysfunction, rhabdomyolysis, and cardiovascular toxicity (JAMA. 2007; 297: 1362-73), therefore, modulation of PPARα activity with endogenous ligands such as PEA may provide a safer treatment. Pharmacologic strategies aimed at correcting a deficit in PEA/PPARα signaling by preventing PEA degradation provide a new mechanism for the treatment of inflammatory disorders. NAAA inhibition offers the advantage of blocking PEA degradation under inflammatory stress and stimulating PPARα activation. A reduction in the reinforcing addictive nature for drugs of abuse has also been reported for inhibition of NAAA (Addict Biol. 2010; 15(3):277-88). These characteristics make NAAA an excellent therapeutic target for discovery of novel compounds to treat pain and inflammation without the addictive properties of opioids.

SUMMARY

The present technology is directed to compounds, compositions, and methods to inhibit N-acylethanolamine hydrolyzing acid amidase and to treat N-acylethanolamine hydrolyzing acid amidase mediated conditions in a subject.

In one aspect, a compound of Formula I, a tautomer thereof, a stereoisomer thereof, or a pharmaceutically acceptable salt thereof, is provided:

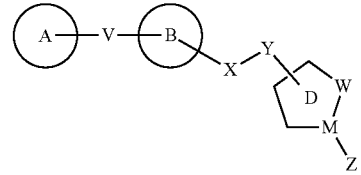

Formula I wherein:
M is N, C, or CR, wherein R is H or alkyl;
Z is NCS, $-(CH_2)_n NCS$, CN, $-(CH_2)_n CN$, or $-CR^1 R^2 CN$, wherein n is 1, 2, 3, 4, or 5, $R^1$ and $R^2$ are each independently H or $C_1$-$C_4$ alkyl, or $R^1$ and $R^2$ together with the carbon to which they are joined form a $C_3$-$C_8$ cycloalkyl; with the proviso that where Z is NCS, M is C or CR;
W is $(CH_2)_n$, and n is 0, 1, 2, or 3;
D is a cycloalkyl, aryl, heterocyclyl, heteroaryl, or D is an a $C_1$-$C_3$ alkylenyl linking Y and M;
Y is $(CH_2)_n$, $O(CH_2)_n$, $NR_3(CH_2)_n$, $(CH_2)_n O$, $(CH_2)_n NR_3$, where n is 0, 1, or 2, and $R^3$ is H or $C_1$-$C_4$ alkyl;
X is $CR^4 R^5$ or $(CH_2)_n$, where n is 0, 1, or 2, and $R^4$ and $R^5$ are each independently H, $C_1$-$C_4$ alkyl, cycloalkyl, aryl, heterocyclyl, heteroaryl, or together with the C to which they are attached form a saturated or unsaturated ring; with the proviso that one of $R^4$ and $R^5$ is H or that $R^4$ and $R^5$ together with the C to which they are attached form a saturated or unsaturated ring;
V is absent, O, $NR^5$, $SO_2$, SO, CO, $CONR^6$, $CR^7 R^8$, or $(CH_2)_n$, wherein $R^6$ is H or $C_1$-$C_4$ alkyl; and $R^7$ and $R^8$ are each independently H, $C_1$-$C_4$ alkyl, cycloalkyl, aryl, heterocyclyl, heteroaryl, or together with the C to which they are attached form a saturated or unsaturated ring;
B is $(CH_2)_n$, where n is 2, 3, or 4, cycloalkyl, heterocyclyl, aryl, heteroaryl; and
A is absent, cycloalkyl, aryl, heterocyclyl, heteroaryl.

In another aspect, a compound of Formula II, a tautomer thereof, a stereoisomer thereof, or a pharmaceutically acceptable salt thereof, is provided:

Formula II

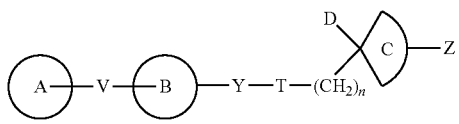

wherein:
Z is CN, NCS, or a CN-substituted $C_1$-$C_3$ alkyl;
C is a 4-12 membered heterocyclyl or heteroaryl containing at least one N
D is hydrogen, $C_1$-$C_3$ alkyl, aryl, or heteroaryl;
T is O or $NR^1$, wherein $R^1$ is H or $C_1$-$C_3$ alkyl;
Y is absent or $C_1$-$C_3$ alkylene;
B is a 5-10 membered aryl or heteroaryl;
V is absent or O;
A is absent, a 5-10 membered aryl, or heteroaryl; and
n is 0, 1, 2, or 3.

In yet another aspect, a composition is provided, the composition containing any of the compounds disclosed herein.

In one aspect, a method of inhibiting NAAA is provided, the method including contacting the NAAA with any of the compounds disclosed herein.

In another aspect, a method of treating an NAAA mediated condition in a subject is provided, the method including administering to the subject any composition disclosed herein. The composition includes an effective amount of any of the compounds disclosed herein.

In yet another aspect, a method of treating an inflammatory gastrointestinal motility disorder, irritable bowel syndrome, or an inflammatory bowel disorder in a subject in need thereof is provided, the method including administering to the subject a therapeutically effective amount of any of the compounds disclosed herein.

In a further aspect, a method of treating ulcerative colitis or Crohn's disease to a patient in need thereof is provided, the method including administering to the patient a therapeutically effective amount of any of the compounds disclosed herein.

In one aspect, a method for modulating the activity of NAAA is provided, the method including contacting an NAAA receptor with an effective amount of any of the compounds disclosed herein.

In another aspect, a method for expression, purification, protein characterization for hNAAA and assay development to screen for hNAAA inhibitors is provided, the method including constructing of mammalian vectors for expressing of C-terminal hexa-histidine tagged hNAAA; using these constructs for generation of a stable transfected HEK293 cell lines; optimization of hNAAA expression, secretion and purification conditions; developing of fluorogenic assay for compounds screening and inhibitor characterization.

In yet another aspect, a method for inhibiting NAAA is provided, the method including administering an effective amount of a compound of Formula III, $S=C=N-(CH_2)_n X$, a tautomer thereof, a stereoisomer thereof, or a pharmaceutically acceptable salt thereof, wherein X is aryl, heteroaryl, amidyl, heterocyclyl, $OR^{20}$, or $(OCH_2CH_2)_p OR^{20}$; p is 0 to 20; and $R^{20}$ is alkyl.

The details of one or more embodiments of the disclosure are set forth in the accompanying description below. Other features, objects, and advantages of the disclosure will be apparent from the description and drawings, and from the claims.

DETAILED DESCRIPTION

Figure 1:
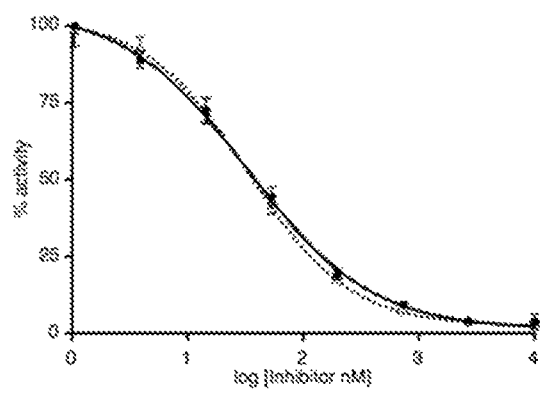
FIG. 1 shows the concentration dependent inhibition of hNAAA by Example 4. The curves represent 15 minutes (filled circles, solid line) and 3 hours (open circles, dotted line) preincubation of hNAAA with NAAA inhibitor Example 4.

In various aspects, the present technology provides compounds, compositions, and methods to inhibit NAAA and to treat NAAA mediated conditions in a subject. Also provided are methods for modulating the activity of NAAA and for expression, purification, protein characterization for hNAAA and assay development to screen for hNAAA inhibitors.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents.

Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms.

Examples of straight chain alkyl groups include groups such as methyl, ethyl, n-propyl, n-butyl, n-pentyl, n-hexyl, n-heptyl, and n-octyl groups.

Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds.

Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Representative substituted alkenyl groups may be mono-substituted or substituted more than once, such as, but not limited to, mono-, di- or tri-substituted with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds.

Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups.

The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group. A "substituted carboxylate" refers to a —C(O)O-G where G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which may be added or removed using the procedures set forth therein and which is hereby incorporated by reference in its entirety and for any and all purposes as if fully set forth herein.

The term "ester" as used herein refers to —COOR$^{70}$ groups. R$^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "halogen" or "halo" as used herein refers to bromine, chlorine, fluorine, or iodine. In some embodiments, the halogen is fluorine. In other embodiments, the halogen is chlorine or bromine.

The term "hydroxy" as used herein can refer to —OH or its ionized form, —O$^-$.

The term "isocyano" refers to —NC.

The term "isothiocyano" refers to —NCS.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable).

When the compound of the present technology has a basic group, such as, for example, an amino group, pharmaceutically acceptable salts may be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid).

When the compound of the present technology has an acidic group, such as for example, a carboxylic acid group, it can form salts with metals, such as alkali and earth alkali metals (e.g. Na$^+$, Li$^+$, K$^-$, Ca$^{2+}$, Mg$^{2+}$, Zn$^{2-}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts may be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

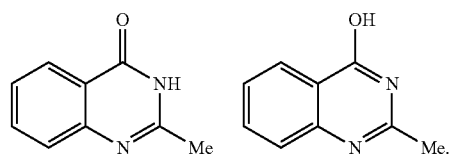

As another example, guanidines may exhibit the following isomeric forms in protic organic solution, also referred to as tautomers of each other:

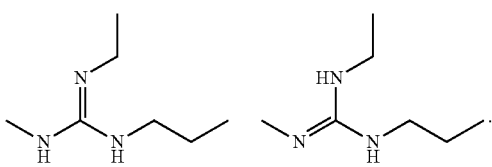

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers may be isolated or synthesized so as to be substantially free of their enantiomeric or diastereomeric partners, and these stereoisomers are all within the scope of the present technology.

Some stereoisomers may be more active or may exhibit beneficial effects when enriched relative to the other stereoisomer(s) or when separated from the other stereoisomer(s). Accordingly, the present disclosure comprises compounds of Formula I, the stereoisomers thereof, and the pharmaceutically acceptable salts thereof. The compounds of the disclosure may be present as a mixture of stereoisomers, individual stereoisomers, or as an optically active or enantiomerically pure form.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

The present technology provides compounds, compositions, and methods to inhibit NAAA and to treat NAAA mediated conditions in a subject. Also provided are methods for modulating the activity of NAAA and for expression, purification, protein characterization for hNAAA and assay development to screen for hNAAA inhibitors.

The present disclosure relates to composition and methods of isothiocyanates and nitrile-based compounds and their use thereof for inhibiting N-acylethanolamine hydrolyzing acid amidase (NAAA) for the treatment and prevention of inflammation and pain and other disorders in which modulation of N-palmitoylethanolamine (PEA) is clinically relevant. Modulation of endogenous PEA concentration is known to exert analgesic, neuroprotective, anti-allergic and GI track antiinflammatory properties. The present disclosure also provides methods for preparing these compounds and pharmaceutical compositions comprising these compounds.

The inventors of the present technology have developed a fluorescence-based assay through which first a library of compounds was screened and several lead compounds were found that have distinct NAAA inhibitory profiles. A new series of NAAA inhibitors have been designed and synthesized based on computational applications and evaluated them in the fluorescence-based assay to identify novel series of NAAA inhibitors. To further these efforst, milligram amounts of NAAA have been cloned, expressed and purified, and the first NMR spectrum of the enzyme obtained. With these tools in hand, the lead compounds have been utilized to probe the molecular features involved in the catalytic site of the enzyme, using a combined biophysical/biochemical approach to elaborate structural details to inform the synthesis of next-generation NAAA-specific inhibitors. Such inhibitors were used as probes to exploit NAAA modulation as potential novel therapeutic targets.

The present technology relates to the discovery of novel NAAA inhibitors and methods suitable for the treatment of various diseases associated with reduced PEA levels in a cell, organ, or even the entire body. In some embodiments, such modulation will result in treatment and/or prevention of pain, inflammation, and other disorders in which abnormal PEA levels are associated with the condition.

In other aspects, the inhibitors are also considered useful as probes for investigation into the mechanism and various pathways in which PEA plays a regulatory and/or modulating role. Surprisingly, it has now been found isothiocyanates and nitrile-based compounds of Formula I demonstrate inhibition of NAAA. Advantageously, such compounds may be used as effective therapeutic agents for the treatment, prevention or amelioration of a disease or disorder characterized by inflammation and pain manifestations in a patient.

The present technology provides compositions and methods of inhibiting NAAA using small organic compounds. Applicant has discovered NAAA inhibitors represented by Formula I, below, and pharmaceutically acceptable salts thereof, wherein variables A, B, D, M, X, Y, V, Z, W are as defined herein.

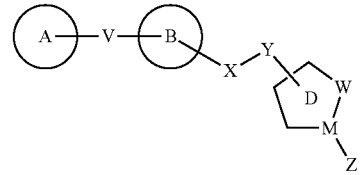

Formula I

In one aspect, a compound of Formula I, a tautomer thereof, a stereoisomer thereof, or a pharmaceutically acceptable salt thereof, is provided:

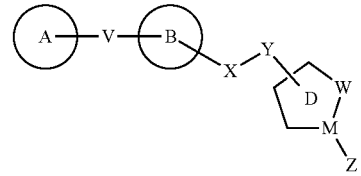

Formula I wherein:
M is N, C, or CR, wherein R is H or alkyl;
Z is NCS, —$(CH_2)_n$NCS, CN, —$(CH_2)_n$CN, or —$CR^1R^2$CN, wherein n is 1, 2, 3, 4, or 5, $R^1$ and $R^2$ are each independently H or $C_1$-$C_4$ alkyl, or $R^1$ and $R^2$ together with the carbon to which they are joined form a $C_3$-$C_8$ cycloalkyl; with the proviso that where Z is NCS, M is C or CR;
W is $(CH_2)_n$, and n is 0, 1, 2, or 3;

D is a cycloalkyl, aryl, heterocyclyl, heteroaryl, or D is an a $C_1$-$C_3$ alkylenyl linking Y and M;

Y is $(CH_2)_n$, $O(CH_2)_n$, $NR_3(CH_2)_n$, $(CH_2)_nO$, $(CH_2)_nNR_3$, where n is 0, 1, or 2, and $R^3$ is H or $C_1$-$C_4$ alkyl;

X is $CR^4R^5$ or $(CH_2)_n$, where n is 0, 1, or 2, and $R^4$ and $R^5$ are each independently H, $C_1$-$C_4$ alkyl, cycloalkyl, aryl, heterocyclyl, heteroaryl, or together with the C to which they are attached form a saturated or unsaturated ring; with the proviso that one of $R^4$ and $R^5$ is H or that $R^4$ and $R^5$ together with the C to which they are attached form a saturated or unsaturated ring;

V is absent, O, $NR^5$, $SO_2$, SO, CO, $CONR^6$, $CR^7R^8$, or $(CH_2)_n$, wherein $R^6$ is H or $C_1$-$C_4$ alkyl; and $R^7$ and $R^8$ are each independently H, $C_1$-$C_4$ alkyl, cycloalkyl, aryl, heterocyclyl, heteroaryl, or together with the C to which they are attached form a saturated or unsaturated ring;

B is $(CH_2)_n$, where n is 2, 3, or 4, cycloalkyl, heterocyclyl, aryl, heteroaryl; and A is absent, cycloalkyl, aryl, heterocyclyl, heteroaryl.

In one embodiment, M may be C or CR, and D may be pyridyl, pyrazinyl, pyridazinyl, or pyrimidinyl, with the proviso that where Z is CN, M is C or CR and a N of the pyridyl, pyrazinyl, pyridazinyl, or pyrimidinyl is attached to M.

In any of the above embodiments, Z may be NCS, CN, $CH_2CN$, $CH(CH_3)CN$, or $C$(cyclopropane)CN; W may be $(CH_2)_n$ where n is 0 or 1; D may be $CH_2$, $CH_2CH_2$, or pyridyl, with the proviso that where D is pyridyl, M is C or CR, and Z is —CN and M is attached to a N atom of the pyridyl group; Y may be $(CH_2)_n$, $O(CH_2)_n$, $NR_3(CH_2)_n$, $(CH_2)_nO$, $(CH_2)_nNH$, or $(CH_2)_nNCH_3$; V may be O, $NCH_3$, $SO_2$, $CONCH_3$, or $(CH_2)_n$ wherein n is 0 or 1; B may be $(CH_2)_{n'}$, phenyl, or a 5 or 6-member heterocyclyl; and A may be phenyl or a 5 or 6-member heterocyclyl.

In any of the above embodiments, Z may be NCS, —$(CH_2)_{1-5}$NCS, CN, —$(CH_2)_{1-5}$CN, or —$CR^1R^2$CN, wherein $R^1$ and $R^2$ are H or form cyclopropyl; M may be N or C; W may be $(CH_2)_n$, and n may be 0, 1, or 2; D may be a cycloalkyl, aryl, heterocyclyl, or heteroaryl; Y may be O, $(CH_2)_n$, $O(CH_2)_n$, $(CH_2)_nO$, $NR^3(CH_2)_n$, $(CH_2)_nNR^3$, where n may be 0, 1, or 2, and $R^3$ may be H or $C_1$-$C_4$ alkyl; X may be $(CH_2)_n$, wherein n may be 0, 1, or 2; B may be $(CH_2)_{n'}$, wherein n' may be 2, 3, or 4, cycloalkyl, heterocyclyl, aryl, heteroaryl; V may be O, $NR^5$, $SO_2$, SO, CO, $CONR^6$, $CR^7R^8$, or $(CH_2)_n$, wherein $R^6$ may be H or $C_1$-$C_4$ alkyl; and $R^7$ and $R^8$ are each independently H, $C_1$-$C_4$ alkyl, cycloalkyl, aryl, heterocyclyl, heteroaryl, or together with the C to which they are attached form a saturated or unsaturated ring; and A may be cycloalkyl, aryl, heterocyclyl, heteroaryl.

In any of the above embodiments, Z may be NCS, —$(CH_2)_{1-5}$NCS, CN, —$(CH_2)_{1-5}$CN, or —$CR^1R^2$CN, wherein $R^1$ and $R^2$ are H or form cyclopropyl; M may be N or C; W may be $(CH_2)_n$, and n may be 0; D may be a cycloalkyl, aryl, heterocyclyl, or heteroaryl; Y may be O, $(CH_2)_n$, $O(CH_2)_n$, $(CH_2)_nO$, $NR^3(CH_2)_n$, $(CH_2)_nNR^3$, where n may be 0, 1, or 2, and $R^3$ may be H or $C_1$-$C_4$ alkyl; X may be $(CH_2)_n$, wherein n may be 0, 1, or 2; B may be $(CH_2)_{n'}$, wherein n' may be 2, 3, or 4, cycloalkyl, heterocyclyl, aryl, heteroaryl; V may be O, $NR^5$, $SO_2$, SO, CO, $CONR^6$, $CR^7R^8$, or $(CH_2)_n$, wherein $R^6$ may be H or $C_1$-$C_4$ alkyl; and $R^7$ and $R^8$ are each independently H, $C_1$-$C_4$ alkyl, cycloalkyl, aryl, heterocyclyl, heteroaryl, or together with the C to which they are attached form a saturated or unsaturated ring; and A may be cycloalkyl, aryl, heterocyclyl, heteroaryl.

In any of the above embodiments, Z may be NCS, —$(CH_2)_{1-5}$NCS, CN, —$(CH_2)_{1-5}$CN, or —$CR^1R^2$CN, wherein $R^1$ and $R^2$ are H or form cyclopropyl; M may be N or C; W may be $(CH_2)_n$, and n may be 0, 1, or 2; D may be a cycloalkyl, aryl, heterocyclyl, or heteroaryl; Y may be O; X may be $(CH_2)_n$, wherein n may be 0, 1, or 2; B may be aryl; V may be $(CH_2)_n$, where n may be 0; and A may be cycloalkyl, aryl, heterocyclyl, heteroaryl.

In another aspect, a compound of Formula II, a tautomer thereof, a stereoisomer thereof, or a pharmaceutically acceptable salt thereof is provided:

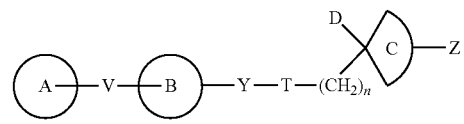

Formula II wherein:

Z is CN, NCS, or a CN-substituted $C_1$-$C_3$ alkyl;

C is a 4-12 membered heterocyclyl or heteroaryl containing at least one N

D is hydrogen, $C_1$-$C_3$ alkyl, aryl, or heteroaryl;

T is O or $NR^1$, wherein $R^1$ is H or $C_1$-$C_3$ alkyl;

Y is absent or $C_1$-$C_3$ alkylene;

B is a 5-10 membered aryl or heteroaryl;

V is absent or O;

A is absent, 5-10 membered aryl or heteroaryl; and n is 0, 1, 2, or 3.

In any of the above embodiments, C may be

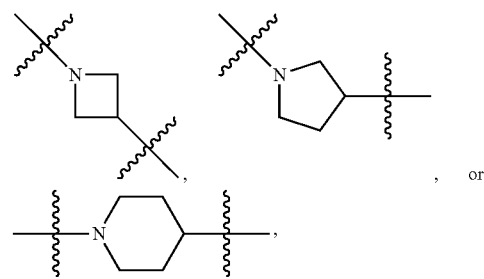

and Z may be CN or —$CH_2$—CN.

In another embodiment, C may be cyclobutyl, cyclopentyl, cyclohexyl, or

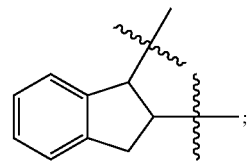 [SMILES: *C1Cc2ccccc2C1*]

and Z may be NCS.

In any of the above embodiments, B may be phenyl. In a further embodiment, B may be substituted phenyl.

In one embodiment, n may be 0.

In another aspect, the following compounds are provided: n-(2-isothiocyanatoethyl)palmitamide; n-(2-isothiocyanatoethyl)-7-(naphthalene-2-yl)heptanamide; 1-isothiocyanato-2-(4-benzylpiperazino)ethane; 4-(4-(isothiocyanatomethyl)

phenyl)morpholine; 4-benzyl-1-(2-isothiocyanatoethyl) piperidine; 4-(morpholinomethyl)benzylisothiocyanate; benzyl-4-(isothiocyanatomethyl)tetrahydro-1(2h)-pyridinecarboxylate; 2-(4-(isothiocyanatomethyl)phenoxy)-6-methylpyrazine; 1-(isothiocyanatomethyl)-4-(phenoxymethyl)benzene; 1-(10-isothiocyanatodecyl)-2-(trifluoromethyl)benzene; 1-(10-isothiocyanatodecyl)-4-methoxybenzene; 2-(10-isothiocyanatodecyl)pyridine; 4-(10-isothiocyanatodecyl)pyridine; 2-(10-isothiocyanatodecyl)pyrimidine; ((2-(2-(2-isothiocyanatoethoxy)ethoxy) ethoxy)methyl)benzene; 3-((3-isothiocyanatopropoxy) methyl)-1,1'-biphenyl; 4-((3-isothiocyanatopropoxy) methyl)-1,1'-biphenyl; 1-((3-isothiocyanatopropoxy) methyl)-4-phenoxybenzene; 4-benzyl-1-(5-isothiocyanatopentyl)piperidine; 4-(((1R,3R)-3-isothiocyanatocyclobutoxy)methyl)-4'-methyl-1,1'-biphenyl; 4-(((1S,3S)-3-isothiocyanatocyclobutoxy) methyl)-4'-methyl-1,1'-biphenyl; 4-(((1R,3R)-3-isothiocyanatocyclobutoxy)methyl)-1,1'-biphenyl; 4-(((1S, 3S)-3-isothiocyanatocyclobutoxy)methyl)-1,1'-biphenyl; 3,4'-difluoro-4-(((1S,3S)-3-isothiocyanatocyclobutoxy) methyl)-1,1'-biphenyl; 3,3'-difluoro-4-(((1S,3S)-3-isothiocyanatocyclobutoxy)methyl)-4'-methoxy-1,1'-biphenyl; 4'-(((1R,3R)-3-isothiocyanatocyclobutoxy)methyl)-3-methoxy-1,1'-biphenyl; 4'-(((1S,3S)-3-isothiocyanatocyclobutoxy)methyl)-3-methoxy-1,1'-biphenyl; 4-ethoxy-3,3'-difluoro-4'-(((1S,3S)-3-isothiocyanatocyclobutoxy)methyl)-1,1'-biphenyl; 3,3'-difluoro-4-isopropoxy-4'-(((1S,3S)-3-isothiocyanatocyclobutoxy)methyl)-1,1'-biphenyl; 6-(3-fluoro-4-(((1S,3S)-3-isothiocyanatocyclobutoxy)methyl) phenyl)-2,3-dihydrobenzo[b][1,4]dioxine; 5-(3-fluoro-4-(((1S,3S)-3-isothiocyanatocyclobutoxy)methyl)phenyl) benzo[d][1,3]dioxole; 3-fluoro-4-(((1S,3S)-3-isothiocyanatocyclobutoxy)methyl)-3',4'-dimethoxy-1,1'-biphenyl; 3-(3-fluoro-4-(((1R,3R)-3-isothiocyanatocyclobutoxy)methyl)phenyl)-2-methoxypyridine; 5-(3-fluoro-4-methoxyphenyl)-2-(((1R, 3R)-3-isothiocyanatocyclobutoxy)methyl)pyridine; 3,4'-difluoro-3'-(((1S,3S)-3-isothiocyanatocyclobutoxy)methyl)-4-methoxy-1,1'-biphenyl; 4-bromo-2-fluoro-1-(((1R,3R)-3-isothiocyanatocyclobutoxy)methyl)benzene; 4-(3-fluoro-4-(((1R,3R)-3-isothiocyanatocyclobutoxy)methyl)phenyl)-3,5-dimethylisoxazole; 4-(3-fluoro-4-(((1R,3R)-3-isothiocyanatocyclobutoxy)methyl)phenyl)-1-methyl-1h-pyrazole; 3-fluoro-4-(((1R,3R)-3-isothiocyanatocyclobutoxy)methyl)-3'-(trifluoromethyl)-1, 1'-biphenyl; 3'-(benzyloxy)-3-fluoro-4-(((1R,3R)-3-isothiocyanatocyclobutoxy)methyl)-1,1'-biphenyl; 2-bromo-1-(((1S,3S)-3-isothiocyanatocyclobutoxy) methyl)-4-phenoxybenzene; 4,2-(((1S,3S)-3-isothiocyanatocyclobutoxy)methyl)-5-phenoxy-1,1'-biphenyl; 3-fluoro-4'-((1R,3R)-3-isothiocyanatocyclobutoxy)-4-methoxy-1,1'-biphenyl; 3-fluoro-4'-((1S,3S)-3-isothiocyanatocyclobutoxy)-4-methoxy-1,1'-biphenyl; (1R,3R)-n-([1, 1'-biphenyl]-4-ylmethyl)-3-isothiocyanato-n-methylcyclobutan-1-amine; (1S,3S)-n-([1,1'-biphenyl]-4-yl)methyl)-3-isothiocyanato-n-methylcyclobutan-1-amine; (1R,3R)-n-(4-(benzo[d][1,3]dioxol-5-yl)benzyl)-3-isothiocyanato-n-methylcyclobutan-1-amine; (1R,3R)-n-(4-(benzo[d][1,3]dioxol-5-yl)benzyl)-n-ethyl-3-isothiocyanatocyclobutan-1-amine; 4-(((1S,3S)-3-(isothiocyanatomethyl) cyclobutoxy)methyl)-1,1'-biphenyl; 4'-(((3-isothiocyanatocyclohexyl)oxy)methyl)-3-(trifluoromethyl)-1,1'-biphenyl; 3-fluoro-4'-((((1R,4R)-4-isothiocyanatocyclohexyl)oxy)methyl)-4-methoxy-1,1'-biphenyl; 1-bromo-4-((((1R,3R)-3-isothiocyanatocyclopentyl)oxy)methyl)benzene; (1R,2S)-1-isothiocyanato-2-((3'-(trifluoromethyl)-[1,1'-biphenyl]-4-yl)methoxy)-2,3-dihydro-1h-indene; (1S,2R)-2-((3'-fluoro-4'-methoxy-[1,1'-biphenyl]-4-yl)methoxy)-1-isothiocyanato-2,3-dihydro-1H-indene; 3-((4'-methoxy-[1,1'-biphenyl]-4-yl)methoxy) azetidine-1-carbonitrile; 3-([1,1'-biphenyl]-4-ylmethoxy) azetidine-1-carbonitrile; 3-((2',4'-dimethoxy-[1,1'-biphenyl]-4-yl)methoxy)azetidine-1-carbonitrile; 3-([1,1'-biphenyl]-3-ylmethoxy)azetidine-1-carbonitrile; 3-((3'-methoxy-[1,1'-biphenyl]-4-yl)methoxy)azetidine-1-carbonitrile; 3-((2',5'-dimethyl-[1,1'-biphenyl]-4-yl) methoxy)azetidine-1-carbonitrile; 3-((2',3'-dimethoxy-[1,1'-biphenyl]-4-yl)methoxy)azetidine-1-carbonitrile; 3-((3'-(trifluoromethyl)-[1,1'-biphenyl]-4-yl)methoxy)azetidine-1-carbonitrile; 3-((3',5'-bis(trifluoromethyl)-[1,1'-biphenyl]-4-yl)methoxy)azetidine-1-carbonitrile; 3-((4-(pyridin-3-yl) benzyl)oxy)azetidine-1-carbonitrile; 3-((4-(6-methoxypyridin-3-yl)benzyl)oxy)azetidine-1-carbonitrile; 3-((4-(2-methoxypyridin-3-yl)benzyl)oxy)azetidine-1-carbonitrile; 3-((2'-methoxy-[1,1'-biphenyl]-4-yl)methoxy)azetidine-1-carbonitrile; 3-((4'-methyl-[1,1'-biphenyl]-4-yl) methoxy)azetidine-1-carbonitrile; 3-((4'-fluoro-[1,1'-biphenyl]-4-yl)methoxy)azetidine-1-carbonitrile; 3-((3-fluoro-3'-methoxy-[1,1'-biphenyl]-4-yl)methoxy)azetidine-1-carbonitrile; 3-((3'-methoxy-3-(trifluoromethyl)-[1,1'-biphenyl]-4-yl)methoxy)azetidine-1-carbonitrile; 3-((3,3'-dimethoxy-[1,1'-biphenyl]-4-yl)methoxy)azetidine-1-carbonitrile; 3-((4-phenoxybenzyl)oxy)azetidine-1-carbonitrile; 3-((1-(3'-methoxy-[1,1'-biphenyl]-4-yl) cyclopropyl)methoxy)azetidine-1-carbonitrile; 3-((2',6'-dimethoxy-[1,1'-biphenyl]-4-yl)methoxy)azetidine-1-carbonitrile; 3-((4-(2,3-dihydrobenzo[b][1,4]dioxin-6-yl) benzyl)oxy)azetidine-1-carbonitrile; 3-((3'-(benzyloxy)-[1, 1'-biphenyl]-4-yl)methoxy)azetidine-1-carbonitrile; 3-(([1, 1'-biphenyl]-4-ylmethoxy)methyl)azetidine-1-carbonitrile; 3-((5-phenoxy-[1,1'-biphenyl]-2-yl)methoxy)azetidine-1-carbonitrile; 3-((2'-methoxy-5-phenoxy-[1,1'-biphenyl]-2-yl)methoxy)azetidine-1-carbonitrile; 3-((3'-methoxy-5-phenoxy-[1,1'-biphenyl]-2-yl)methoxy)azetidine-1-carbonitrile; 3-((4'-methoxy-5-phenoxy-[1,1'-biphenyl]-2-yl)methoxy)azetidine-1-carbonitrile; 3-((2-(2-methoxypyridin-3-yl)-4-phenoxybenzyl)oxy)azetidine-1-carbonitrile; 3-((4'-cyano-5-phenoxy-[1,1'-biphenyl]-2-yl) methoxy)azetidine-1-carbonitrile; 3-((2'-cyano-5-phenoxy-[1,1'-biphenyl]-2-yl)methoxy)azetidine-1-carbonitrile; 3-((4-(bis(4-fluorophenyl)methoxy)-2-bromobenzyl)oxy) azetidine-1-carbonitrile; 3-((3'-methoxy-[1,1'-biphenyl]-4-yl)methoxy)-3-methylazetidine-1-carbonitrile; 3-((3'-methoxy-[1,1'-biphenyl]-4-yl)methoxy)-3-phenylazetidine-1-carbonitrile; 3-((4-(benzo[d][1,3]dioxol-5-yl)benzyl) oxy)-3-phenylazetidine-1-carbonitrile; 3-((4-(2,3-dihydrobenzo[b][1,4]dioxin-6-yl)benzyl)oxy)-3-phenylazetidine-1-carbonitrile; 3-((4-bromophenyl)(phenyl) methoxy)azetidine-1-carbonitrile; 3-((3'-methoxy-[1,1'-biphenyl]-4-yl)(phenyl)methoxy)azetidine-1-carbonitrile; 3-((4-(3,5-dimethylisoxazol-4-yl)phenyl)(phenyl)methoxy) azetidine-1-carbonitrile; 3-((4-(1-methyl-1h-pyrazol-4-yl) phenyl)(phenyl)methoxy)azetidine-1-carbonitrile; 3-((4-(1-methyl-1h-pyrazol-4-yl)phenyl)(phenyl)methoxy)azetidine-1-carbonitrile; 3-(([1,1'-biphenyl]-4-ylmethyl)(methyl) amino)azetidine-1-carbonitrile; (S)-3-([1,1'-biphenyl]-4-ylmethoxy)pyrrolidine-1-carbonitrile; (R)-3-([1,1'-biphenyl]-4-ylmethoxy)pyrrolidine-1-carbonitrile; (1R,3R)-3-([1,1'-biphenyl]-4-ylmethoxy)cyclobutane-1-carbonitrile; (1S,3S)-3-([1,1'-biphenyl]-4-ylmethoxy)cyclobutane-1-carbonitrile; 2-(3-((3'-methoxy-[1,1'-biphenyl]-4-yl)methoxy) azetidin-1-yl)acetonitrile; 5-((2-bromo-4-phenoxybenzyl)

oxy)picolinonitrile; 5-([1,1'-biphenyl]-4-ylmethoxy) picolinonitrile; 5-([1,1'-biphenyl]-4-ylmethoxy)-3-fluoropicolinonitrile; 3-([1,1'-biphenyl]-4-ylmethoxy)-5-fluoropicolinonitrile; 5-phenylpentyl6-cyanopicolinate; 5-((6-phenylhexyl)oxy)pyrimidine-2-carbonitrile; 5-((5-phenylpentyl)oxy)pyrimidine-2-carbonitrile; 5-(2-(2-(benzyloxy)ethoxy)ethoxy)pyrimidine-2-carbonitrile; a tautomer thereof; a stereoisomer thereof; or a pharmaceutically acceptable salt thereof.

In one aspect, a composition is provided, the composition containing any of the compounds disclosed herein, and a pharmaceutically acceptable excipient.

In one aspect, the compositions include one or more compounds of formula I and one or more pharmaceutically acceptable carriers. Pharmaceutical compositions may also contain compounds of the above-described Formula I, Formula II, or any other described herein, along with a pharmaceutically acceptable carrier.

The term "carrier," as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. Oral formulations containing the active compounds of this disclosure may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. In one embodiment, the powders and tablets contain up to 99% of the active ingredient. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins.

In one embodiment, the surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine.

Oral formulations herein may utilize standard delay or time release formulations to alter the absorption of the active compound(s). The oral formulation may also consist of administering the active ingredient in water or fruit juice, containing appropriate solubilizers or emulisifiers as needed. Liquid carriers may be used in preparing solutions, suspensions, emulsions, syrups and elixirs. The active ingredient of this disclosure may be dissolved or suspended in a pharmaceutically acceptable liquid carrier such as water, an organic solvent, a mixture of both or pharmaceutically acceptable oils or fat.

The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, sodium carboxymethyl cellulose solution), alcohols (including monohydric alcohols and polyhydric alcohols, e.g. glycols) and their derivatives, and oils (e.g. fractionated coconut oil and arachis oil). In one embodiment, the additive is sodium carboxymethyl cellulose solution.

For parenteral administration the carrier can also be an oily ester such as ethyl oleate and isopropyl myristate. Sterile liquid carriers are used in sterile liquid form compositions for parenteral administration. The liquid carrier for pressurized compositions may be halogenated hydrocarbon or other pharmaceutically acceptable propellant. Liquid pharmaceutical compositions, which are sterile solutions or suspensions, may be utilized by, for example, intramuscular, intraperitoneal or subcutaneous injection. Sterile solutions can also be administered intravenously.

Compositions for oral administration may be in either liquid or solid form. In one embodiment, the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms may be packaged compositions, for example, packeted powders, vials, ampoules, prefilled syringes or sachets containing liquids.

The unit dosage form may be, for example, a capsule or tablet itself, or it may be the appropriate number of any such compositions in package form. Such unit dosage form may contain from about 1 mg/kg to about 250 mg/kg, and may be given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally and transdermally. Such administrations may be carried out using the compounds disclosed herein, or pharmaceutically acceptable salts thereof, in lotions, creams, foams, patches, suspensions, solutions, and suppositories (rectal). When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated.

In therapeutic application, compounds of the present disclosure are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient. The compounds of this disclosure may be administered parenterally or intraperitoneally. Solutions or suspensions of these active compounds as a free base or pharmaceutically acceptable salt may be prepared in water suitably mixed with a surfactant such as hydroxylpropylcellulose. Dispersions may also be prepared in glycerol, liquid polyethylene glycols and mixtures thereof in oils. Under ordinary conditions of storage and use, these preparations contain a preservative to inhibit the growth of microorganisms. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The carrier may be a solvent or dispersion medium containing, for example, water, ethanol, polyol (e.g., glycerol, propylene glycol and liquid polyethylene glycol), suitable mixtures thereof, and vegetable oils. In certain embodiments, the present disclosure is directed to pro-drugs. It is understood that the dosage, regimen and mode of administration of these compounds will vary according to the malady and the individual being treated and will be subject to the judgment of the medical practitioner involved.

In one embodiment, the administration of one or more of the compounds disclosed herein begin at a low dose and be increased until the desired effects are achieved.

As used herein, the term "providing," with respect to providing a compound or substance disclosed herein, means either directly administering such a compound or substance, or administering a pro-drug, derivative, or analog which will form the effective amount of the compound or substance within the body. This disclosure also covers providing the compounds disclosed herein to treat the disease states disclosed herein for which the compounds are useful for treating.

The term "patient," as used herein, refers to a mammal, preferably a human.

The terms "administer," "administering," or "administration," as used herein, refer to either directly administering a compound or composition to a patient, or administering a pro-drug derivative or analog of the compound to the patient, which will form an equivalent amount of the active compound or substance within the patient's body.

The terms "effective amount," "therapeutically effective amount" and "effective dosage" as used herein, refer to the amount of a compound that, when administered to a patient, is effective to at least partially ameliorate (and, in preferred embodiments, cure) a condition from which the patient is suspected to suffer. It is understood that the effective dosage of the active compounds of this disclosure may vary depending upon the particular compound utilized, the mode of administration, the condition, and severity thereof, of the condition being treated, as well as the various physical factors related to the individual being treated.

For treating IBD diseases and other related inflammatory diseases, generally, satisfactory results may be obtained when the compounds of this disclosure are administered to the individual in need at a daily dosage of from about 1 mg to about 10 mg per kilogram of body weight, preferably administered in divided doses two to six times per day, or in a sustained release form. For most large mammals, the total daily dosage is from about 10 mg to about 100 mg preferably from about 5 to about 20 mg. In the case of a 70 kg human adult, the total daily dose will generally be from about 10 mg to about 150 mg and may be adjusted to provide the optimal therapeutic result. This regimen may be adjusted to provide the optimal therapeutic response.

The compounds disclosed herein act as NAAA inhibitors for the treatment of inflammation, pain and other neuroinflammation disorders. Accordingly, in one aspect, the present disclosure provides a method for inhibiting NAAA, the method including contacting the NAAA with any compound disclosed herein.

In another aspect, a method for treating an NAAA-mediated condition in a subject is provided, the method including administering to the subject a composition containing an effective amount of a compound disclosed herein.

In yet another aspect, provided herein is a method of treating, preventing, or ameliorating inflammatory conditions of the gastrointestinal tract. In one embodiment, the inflammatory condition is ulcerative colitis and Crohn's disease.

In a further aspect, provided is a method of treating an inflammatory gastrointestinal motility disorder, irritable bowel syndrome, or an inflammatory bowel disorder in a subject in need thereof, the method including administering to the subject a therapeutically effective amount of a compound disclosed herein.

In one embodiment, the disease or disorder is ulcerative colitis or Crohn's disease.

In one aspect, provided is a method for the treatment of ulcerative colitis in a patient in need thereof, the method including administering to the patient a therapeutically effective amount of a compound disclosed herein.

In one aspect, provided is a method for the treatment of Crohn's disease in a patient in need thereof, the method including administering to the patient a therapeutically effective amount of a compound disclosed herein.

In another aspect, a method for modulating the activity of NAAA is provided, the method including contacting a receptor thereof with an effective amount of a compound disclosed herein.

In yet another aspect is provided a method for expression, purification, protein characterization for hNAAA and assay development to screen for hNAAA inhibitors, the method including constructing of mammalian vectors for expressing of C-terminal hexa-histidine tagged hNAAA; using these constructs for generation of a stable transfected HEK293 cell lines; optimization of hNAAA expression, secretion and purification conditions; developing of fluorogenic assay for compounds screening and inhibitor characterization.

In a further aspect, provided is a method for inhibiting NAAA, the method including administering an effective amount of a compound of Formula III, a tautomer thereof, a stereoisomer thereof, or a pharmaceutically acceptable salt thereof:

$$S=C=N-(CH_2)_nX \qquad \text{Formula III;}$$

wherein:

X is aryl, heteroaryl, amidyl, heterocyclyl, OR[20], or (OCH$_2$CH$_2$)$_p$OR[20];

p is 0 to 20; and

R[20] is alkyl.

In one embodiment, X is substituted aryl, substituted heteroaryl, or substituted heterocyclyl, wherein the substitution is F, Cl, Br, I, perhaloalkyl, C$_1$-C$_{20}$ alkyl, C$_1$-C$_3$ alkoxy, aryl, arylalkenyl, aryloxy, heteroarylalkenyl, heterocyclyl, heterocyclylalkenyl, carboxy, heteroaryloxy, or —CH$_2$—O-phenyl.

Also provided is a method of treating pain and related analgesia in humans or other mammals which includes administering to a human or other mammal an effective amount of a compound of the present disclosure.

Certain methods further include determining NAAA activity, either before or after the contacting step.

For a more clear understanding, and in order to illustrate the disclosure more clearly, specific examples thereof are set forth herein below.

The following examples herein are provided to illustrate advantages of the present technology and to further assist a person of ordinary skill in the art with preparing or using the compounds of the present technology or salts, pharmaceutical compositions, derivatives, metabolites, prodrugs, racemic mixtures or tautomeric forms thereof.

The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Unless otherwise stated, all parts are parts by weight.

The terms TEA, DMSO and DMF designate triethyl amine, dimethyl sulfoxide and N,N-dimethylformamide, respectively.

The term TLC designates thin layer chromatography.

The term NMR designates nuclear magnetic resonance, and the term MS designates mass spectroscopy with (+) referring to the positive mode which generally gives a M$^+$1 (or M$^+$H) absorption where M=the molecular mass. Proton nuclear magnetic resonance spectra were obtained on a VARIAN 400 spectrometer at 500 MHz. Spectra are reported in ppm (δ) and coupling constants, J values, are reported in Hertz (Hz). Tetramethylsilane was used as an internal reference standard.

Infrared spectra were obtained on a Perikn Elmer Spectrum One FT-IR spectrometer. Mass spectra were obtained on a Waters Micromass ZQ spectrometer.

Method A.

Isothiocyanates 3 (Scheme 1) were accessed either through their corresponding amines 4 or alcohols 1. Amines 4 were treated with 1,1'-thiocarbonyldipyridin-2(1H)-one to yield isothiocyanates 3. In the case of the alcohols, they were first converted to azides 2, which were further treated with PPh$_3$ and CS$_2$ to provide isothiocyanates 3.

Scheme 1:

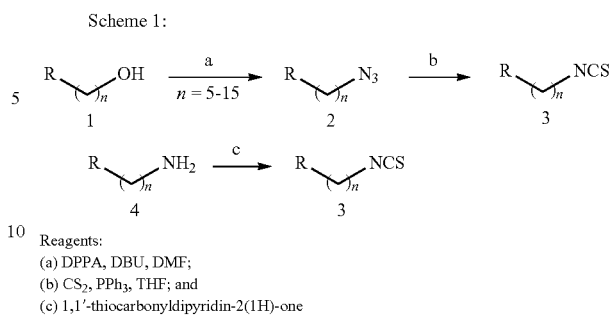

Reagents:
(a) DPPA, DBU, DMF;
(b) CS$_2$, PPh$_3$, THF; and
(c) 1,1'-thiocarbonyldipyridin-2(1H)-one The following examples were prepared according to Method A.

Example 1

(4-isothiocyanatobutyl)benzene: $^1$H NMR (500 MHz, CDCl$_3$) δ 7.27-7.32 (m, 2H), 7.14-7.23 (m, 3H), 3.52 (t, J=6.4 Hz, 2H), 2.66 (t, J=7.1 Hz, 2H), 1.67-1.81 (m, 4H). IR (neat) cm$^{-1}$ 3026, 2926, 2859, 2183, 2089. HRMS for C$_{11}$H$_{13}$NS (M$^+$) 191.0760. Calcd. 191.0769.

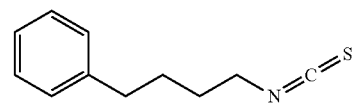 [SMILES: S=C=NCCCCc1ccccc1]

Example 2

(5-Isothiocyanatopentyl)benzene: $^1$H NMR (500 MHz, CDCl$_3$) δ 7.25-7.29 (m, 2H), 7.15-7.22 (m, 3H), 3.50 (t, J=6.6 Hz, 2H), 2.63 (t, J=7.3 Hz, 2H), 1.72 (td, J=6.8, 15.1 Hz, 2H), 1.66 (td, J=7.6, 15.5 Hz, 2H), 1.42-1.50 (m, 2H). IR (neat) cm$^{-1}$ 3026, 2935, 2857, 2183, 2086. HRMS for C$_{12}$H$_{15}$NS (M$^+$) 205.0938. Calcd. 205.0925.

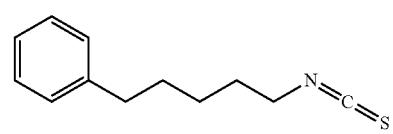 [SMILES: S=C=NCCCCCc1ccccc1]

Example 3

(8-Isothiocyanatooctyl)benzene: $^1$H NMR (500 MHz, CDCl$_3$) δ 7.26-7.30 (m, 2H), 7.13-7.21 (m, 3H), 3.50 (t, J=6.8 Hz, 2H), 2.60 (t, J=6.8 Hz, 2H), 1.58-1.72 (m, 4H), 1.37-1.44 (m, 2H), 1.28-1.37 (m, 6H). IR (neat) cm$^{-1}$ 3026, 2927, 2955, 2179, 2090. HRMS for C$_{15}$H$_{21}$NS (M$^+$) 247.1387. Calcd. 247.1395.

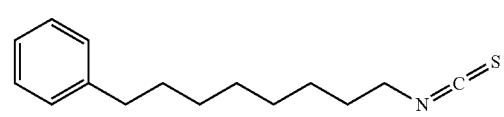 [SMILES: S=C=NCCCCCCCCc1ccccc1]

Example 4

(10-Isothiocyanatodecyl)benzene: $^1$H NMR (500 MHz, CDCl$_3$) δ 7.24-7.31 (m, 2H), 7.14-7.21 (m, 3H), 3.50 (t, J=6.6 Hz, 2H), 2.60 (t, J=7.3 Hz, 2H), 1.65-1.72 (m, 2H), 1.61 (quin, J=7.5 Hz, 2H), 1.36-1.44 (m, 2H), 1.24-1.35 (m, 10H). IR (neat) cm$^{-1}$ 3026, 2924, 2854, 2178, 2088. HRMS for $C_{17}H_{25}NS$ (M$^+$) 275.1715. Calcd. 275.1708.

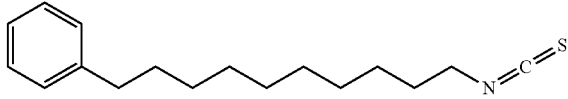 [SMILES: S=C=NCCCCCCCCCCc1ccccc1]

Example 5

2-(7-Isothiocyanatoheptyl)naphthalene: $^1$H NMR (500 MHz, CDCl$_3$) δ 7.72-7.82 (m, 4H), 7.60 (s, 1H), 7.37-7.48 (m, 3H), 7.32 (dd, J=1.5, 8.3 Hz, 1H), 3.47 (t, J=6.8 Hz, 2H), 2.77 (t, J=7.6 Hz, 2H), 1.62-1.75 (m, 4H), 1.31-1.43 (m, 6H). IR (neat) cm$^{-1}$ 3053, 2929, 2856, 2093. HRMS for $C_{18}H_{21}NS$ (MH+) 284.1478. Calcd. 284.1473.

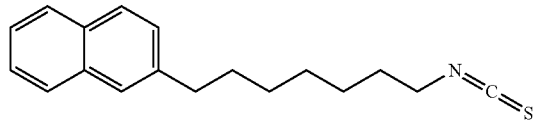 [SMILES: S=C=NCCCCCCCc1ccc2ccccc2c1]

Method B.

Amides 2 and 6 (Scheme 2) were synthesized from corresponding acids 1 and 5 being coupled with ethanolamine through 1-ethyl-3-(3-dimethylaminopropyl)carbodiimide (EDCI) and 4-dimethylaminopyridine (DMAP). The alcohol was then converted to the azide with diphenylphosphoryl azide (DPPA) and 1,8-diazabicyclo[5.4.0]undec-7-ene (DBU) to yield 3 and 7. Triphenylphosphine (PPh$_3$) and carbon disulfide (CS$_2$) were then used to convert the azide to the desired isothiocyanate of compounds 4 and 8.

Scheme 2:

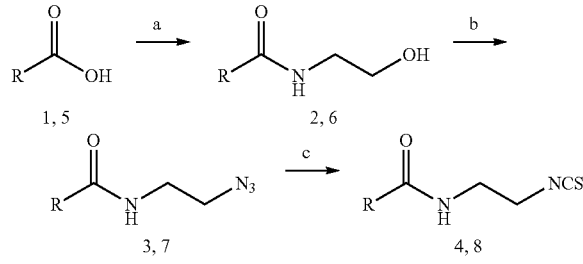

For 1, 2, 3, and 4, R = (CH$_2$)$_6$C$_{10}$H$_7$
For 5, 6, 7, and 8, R = C$_{15}$H$_{32}$
Reagents: (a) C$_2$H$_5$Cl$_2$ (EDCl), 4-dimethylaminopyridine (DMAP), CH$_2$Cl$_2$, ethanolamine, 0° C., 2 h; (b) diphenylphosphoryl azide (DPPA), 1,8-diazabicyclo[5.4.0]undec-7-ene(DBU), DMF, 120° C., 4 h; (c) PPh$_3$, CS$_2$, THF The following examples were prepared according to Method B.

Example 6

N-(2-isothiocyanatoethyl)palmitamide: Step 1. Palmitoylethanolamide, 2: EDCI (673 mg, 3.51 mmol), DMAP (44 mg, 0.35 mmol), and ethanolamine (0.141 mL, 2.34 mmol) were added to a solution palmitic acid 1 (300 mg, 1.17 mmol) was stirred in 10 mL of anhydrous CH$_2$Cl$_2$ at 0° C. The reaction was allowed to stir under argon for 4 hours while warming to room temperature. Upon completion the reaction mixture was diluted with CH$_2$Cl$_2$, washed with water and brine. The organic layer was collected and concentrated. The resulting residue was chromatographed on silica to yield 2 (312 mg, 72%) as a white solid. $^1$H NMR (500 MHz, CDCl$_3$) δ 3.70-3.76 (m, 2H), 3.43 (q, J=5.37 Hz, 2H), 2.17-2.24 (m, 2H), 1.64 (quin, J=7.45 Hz, 2H), 1.52 (d, J=1.0 Hz, 1H), 1.19-1.35 (m, 26H).

Step 2. N-(2-azidoethyl)palmitamide, 3: DBU (0.039 mL, 0.26 mmol) and DPPA (0.056 mL, 0.26 mmol) were added to a solution of 2 (50 mg, 0.17 mmol) was stirred in 4 mL of anhydrous DMF at 120° C. The reaction was allowed to stir under argon for 2 hours. The reaction mixture was diluted with ether, washed with water and brine and the organic layer was separated and concentrated. The resulting residue was chromatographed on silica gel to yield 3 (36 mg, 66%) as an off white solid. $^1$H NMR (500 MHz, CDCl$_3$) d 3.35-3.49 (m, 4H), 2.19 (t, J=7.3 Hz, 2H), 1.63 (quin, J=7.5 Hz, 2H), 1.19-1.37 (m, 24H), 0.88 (t, J=6.8 Hz, 3H).

Step 3. N-(2-isothiocyanatoethyl)palmitamide, 4: PPh$_3$ (36 mg, 0.14 mmol) and CS$_2$ (0.01 mL, 0.16 mmol) were added to a solution of 3 (35 mg, 0.11 mmol) in 5 mL of anhydrous THF under an atmosphere of argon. The reaction was allowed to stir for 48 hours. The reaction mixture was concentrated and the resulting residue was chromatographed on silica gel to yield 4 (25 mg, 68%) as a white solid. Mp 72-74° C. $^1$H NMR (500 MHz, CDCl$_3$) δ 5.79-5.99 (m, 1H), 3.68 (t, J=5.4 Hz, 2H), 3.51 (q, J=5.9 Hz, 2H), 2.22 (t, J=7.6 Hz, 2H), 1.64 (td, J=7.5, 14.4 Hz, 2H), 1.22-1.39 (m, 24H), 0.88 (t, J=7.1 Hz, 3H). IR (neat) cm$^{-1}$ 3288, 2917, 2849, 2182, 2094, 1645. HRMS for $C_{19}H_{36}N_2OS$ (MH$^+$) 341.2623. Calcd. 341.2627.

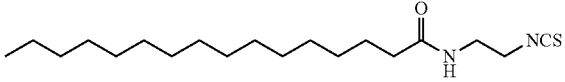

Example 7

N-(2-Isothiocyanatoethyl)-7-(naphthalene-2-yl)heptanamide: $^1$H NMR (500 MHz, CDCl$_3$) δ 7.89-7.92 (m, 1H), 7.71-7.82 (m, 4H), 7.41-7.50 (m, 2H), 3.68 (t, J=5.4 Hz, 2H), 3.52 (q, J=5.9 Hz, 2H), 2.51 (t, J=6.8 Hz, 2H), 2.32 (t, J=7.8 Hz, 2H), 1.88 (quin, J=7.8 Hz, 3H), 1.67-1.77 (m, 4H), 1.48-1.55 (m, 2H). IR (neat) cm$^{-1}$ 3303, 3058, 2930, 2856, 2198, 2110, 1652. HRMS for $C_{20}H_{24}N_2OS$ (M$^+$) 340.1584. Calcd. 340.1609.

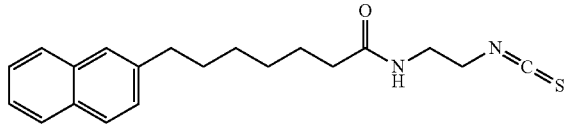 [SMILES: O=C(CCCCCCc1ccc2ccccc2c1)NCCN=C=S]

Example 8

4-(4-Isothiocyanatobenzyl)pyridine: $^1$H NMR (400 MHz, CDCl$_3$) δ 8.50-8.53 (m, 2H), 7.13-7.20 (m, 4H), 7.05-7.09 (m, 2H), 3.96 (s, 2H). IR (neat) cm$^{-1}$ 3067, 3027, 2932, 2174, 2088, 1597. HRMS for $C_{13}H_{10}N_2S$ (MH+) 227.0637. Calcd. 227.0643.

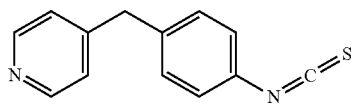 [SMILES: S=C=Nc1ccc(Cc2ccncc2)cc1]

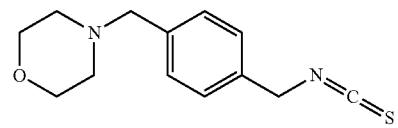

Example 9

1-Isothiocyanato-2-(4-benzylpiperazino)ethane: $^1$H NMR (400 MHz, CDCl$_3$) δ 7.28-7.37 (m, 4H), 7.21-7.28 (m, 1H), 3.58 (t, J=6.2 Hz, 2H), 3.51 (s, 2H), 2.67 (t, J=6.6 Hz, 2H), 2.45-2.57 (m, 8H). IR (neat) cm$^{-1}$ 3027, 2939, 2810, 2190, 2097. HRMS for C$_{14}$H$_{19}$N$_3$S (MH+) 262.1371. Calcd. 262.1378.

Example 13

Benzyl 4-(isothiocyanatomethyl)tetrahydro-1(2H)-pyridinecarboxylate: $^1$H NMR (500 MHz, CDCl$_3$) δ 7.30-7.39 (m, 5H), 5.13 (s, 2H), 4.14-4.41 (m, 2H), 3.42 (d, J=6.4 Hz, 2H), 2.79 (br. s., 2H), 1.80-1.92 (m, 1H), 1.76 (d, J=13.2 Hz, 2H), 1.16-1.33 (m, 2H). IR (neat) cm$^{-1}$ 3027, 2934, 2855, 2187, 2097, 1697. HRMS for C$_{15}$H$_{18}$N$_2$O$_2$S (MH$^+$) 291.1175. Calcd. 291.1167.

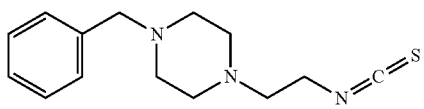 [SMILES: S=C=NCCN1CCN(Cc2ccccc2)CC1]

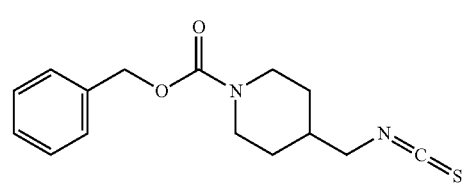

Example 10

4-(4-(Isothiocyanatomethyl)phenyl)morpholine: $^1$H NMR (400 MHz, CDCl$_3$) δ 7.19-7.28 (m, 2H), 6.88-6.96 (m, 2H), 4.62 (s, 2H), 3.83-3.90 (m, 4H), 3.13-3.24 (m, 4H). IR (neat) cm$^{-1}$ 3031, 2957, 2856, 2172, 2090, 1724. HRMS for C$_{12}$H$_{14}$N$_2$OS (MH$^+$) 235.0902. Calcd. 235.0905.

Example 14

2-(4-(Isothiocyanatomethyl)phenoxy)-6-methylpyrazine: $^1$H NMR (400 MHz, CDCl$_3$) δ 8.18 (s, 2H), 7.36 (d, J=8.8 Hz, 2H), 7.12-7.23 (m, 2H), 4.74 (s, 2H), 2.43 (s, 4H). IR (neat) cm$^{-1}$ 3048, 2926, 2852, 2172, 2090. HRMS for C$_{13}$H$_{11}$N$_3$OS (MH$^+$) 258.0697. Calcd. 258.0701.

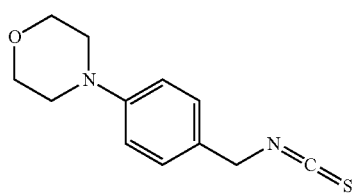 [SMILES: S=C=NCc1ccc(N2CCOCC2)cc1]

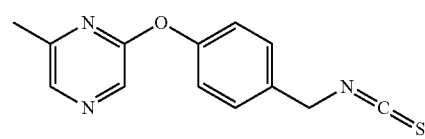

Example 11

4-Benzyl-1-(2-isothiocyanatoethyl)piperidine: $^1$H NMR (400 MHz, CDCl$_3$) δ 7.24-7.32 (m, 2H), 7.16-7.22 (m, 1H), 7.14 (d, J=7.3 Hz, 2H), 3.57 (t, J=6.2 Hz, 2H), 2.85 (d, J=11.7 Hz, 2H), 2.64 (t, J=6.6 Hz, 2H), 2.53 (d, J=6.6 Hz, 2H), 2.03 (dt, J=2.6, 11.5 Hz, 2H), 1.59-1.71 (m, 2H), 1.47-1.56 (m, 1H), 1.23-1.37 (m, 2H). IR (neat) cm$^{-1}$ 3026, 2928, 2804, 2190, 2101. HRMS for C$_{15}$H$_{20}$N$_2$S (MH$^+$) 261.1414. Calcd. 261.1425.

Example 15

1-(Isothiocyanatomethyl)-4-(phenoxymethyl)benzene: $^1$H NMR (400 MHz, CDCl$_3$) δ 8.18 (s, 2H), 7.36 (d, J=8.8 Hz, 2H), 7.12-7.23 (m, 2H), 4.74 (s, 2H), 2.43 (s, 4H). IR (neat) cm$^{-1}$ 3058, 3032, 2925, 2856, 2172, 2091, 1723, 1598. HRMS for C15H13NOS (MH+) 255.0728. Calcd. 255.0718.

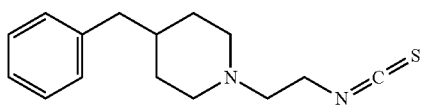 [SMILES: S=C=NCCN1CCC(Cc2ccccc2)CC1]

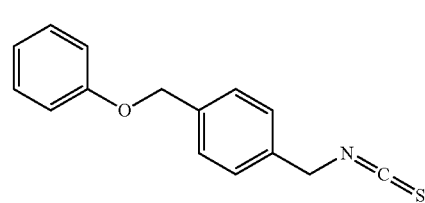 [SMILES: S=C=NCc1ccc(COc2ccccc2)cc1]

Example 12

4-(Morpholinomethyl)benzylisothiocyanate: $^1$H NMR (400 MHz, CDCl$_3$) δ 7.37 (s, 2H), 7.23-7.29 (m, 2H), 4.70 (s, 2H), 3.67-3.76 (m, 4H), 3.50 (s, 2H), 2.45 (d, J=4.4 Hz, 4H). IR (neat) cm$^{-1}$ 3030, 2961, 2854, 2162, 2084, 1612. HRMS for C$_{13}$H$_{16}$N$_2$OS (MH$^+$) 249.1052. Calcd. 249.1062.

Method C.

Aryl substituted alkyl chain isothiocyanates were prepared through a four-step synthetic route (Scheme 3). Sonagashira coupling (step a) of hydroxyl-alkynes with aryliodides and heteroarylbromides either in neat amine base such as diisopropylethylamine or in a polar aprotic solvent such as tetrahydrofuran or 1,4 dioxane with palladium catalysts such as palladium (0) tetrakis or palladium (II) sources and catalytic copper at rt over 16-20 h. Subsequent hydrogenation with palladium on carbon (step b) gave aryl substituted alcohols which were converted to the desired isothiocyanates following the procedures outlined in Method B by conversion to azide then isothiocyanate.

Scheme 3:

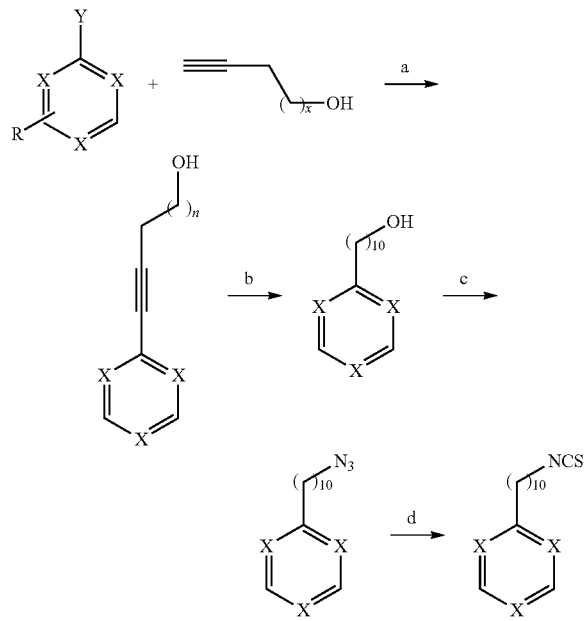

X = C, N
R = CF₃, alkoxy
Y = Br, Cl
n = 3-8

Reagents: (a) DIEA, Pd(PPh₃)₂Cl₂, CuI, dioxane (b) H₂, Pd/C, EtOH (c) DPPA, PPH₃, DIAD, THF (d) PPh₃, CS₂, THF, rt, 48 h.

The following examples were prepared according to Method C.

Example 16

Step 1. 10-(2-(Trifluoromethyl)phenyl)dec-9-yn-1-ol. A stirring solution of 2-iodotrifluoromethylbenzene (272 mg, 1.0 mmol), 9-decyn-1-ol (154 mg, 1.0 mmol) in DIEA (2.5 mL) was purged with argon for 10 mins, then CuI (19 mg, 0.1 mmol), PdCl₂(PPh₃)₂ (3 mg, 0.0025 mmol) were added and the reaction mixture was stirred at rt for 16 h. The reaction mixture was quenched by the addition of sat. ammonium chloride, extracted with EtOAc (3×25 mL). The combined organic phase was washed with brine, dried over sodium sulfate and concentrated under reduced pressure. The crude residue was further purified by silica gel chromatography using 10-100% EtOAc/Hexanes gradient eluent to afford 10-(2-(trifluoromethyl)phenyl)dec-9-yn-1-ol as a colorless oil (135 mg, 35%): ¹H NMR (500 MHz, CDCl₃) δ ppm 7.60 (d, J=7.8 Hz, 1H), 7.45 (app t, J=7.8 Hz, 1H), 7.32 (d, J=7.8 Hz, 1H), 7.23-7.29 (m, 1H), 3.64 (t, J=6.6 Hz, 2H), 2.76 (t, J=7.8 Hz, 2H), 1.55-1.65 (m, 4H), 1.27-1.40 (m, 8H).

Step 2. 10-(2-(Trifluoromethyl)phenyl)decan-1-ol. A stirring solution of 10-(2-(trifluoromethyl)phenyl)dec-9-yn-1-ol (125 mg, 0.42 mmol) and 5% Pd on carbon (25 mg) in EtOH (10 mL) was purged with hydrogen gas and stirred 12 h at rt. The crude reaction mixture was degassed and diluted with EtOAc (100 mL), filtered through celite, and concentrated to afford 10-(2-(trifluoromethyl)phenyl)decan-1-ol as an oily solid (119 mg, 94%): ¹H NMR (500 MHz, CDCl₃) δ ppm 7.60 (d, J=7.8 Hz, 1H), 7.45 (app t, J=7.3 Hz, 1H), 7.33 (d, J=7.6 Hz, 1H), 7.24-7.29 (m, 1H), 3.26 (t, J=7.1 Hz, 2H), 2.76 (t, J=7.8 Hz, 2H), 1.55-1.65 (m, 4H), 1.25-1.40 (m, 8H).

Step 3. 1-(10-Azidodecyl)-2-(trifluoromethyl)benzene. To a stirring solution of triphenylphosphine (123 mg, 0.47) in THF (4.5) at 0° C. under argon was added dropwise DIAD (0.10 mL), and the reaction mixture was stirred for 10 mins. Then 10-(2-(trifluoromethyl)phenyl)decan-1-ol (119 mg, 0.39 mmol) in THF (2.0 mL) was added and the mixture warmed to rt and stirred for 10 mins before adding DPPA ( ) and stirring at rt for 16 h. The reaction was quenched by addition of water (0.5 mL), concentrated and purified by silica gel chromatography using 20-50% EtOAc/Hexanes gradient eluent to afford 1-(10-azidodecyl)-2-(trifluoromethyl)benzene as an oily solid (79 mg, 36%): ¹H NMR (500 MHz, CDCl₃) δ ppm 7.60 (d, J=7.8 Hz, 1H), 7.45 (app t, J=7.8 Hz, 1H), 7.32 (d, J=7.8 Hz, 1H), 7.24-7.29 (m, 1H), 3.51 (t, J=6.6 Hz, 2H), 2.76 (t, J=8.3 Hz, 2H), 1.69 (quin, J=6.8 Hz, 2H), 1.61 (quin, J=6.8 Hz, 2H), 1.25-1.45 (m, 8H).

Step 4. 1-(10-Isothiocyanatodecyl)-2-(trifluoromethyl)benzene. To a stirring solution of 1-(10-azidodecyl)-2-(trifluoromethyl)benzene (60 mg, 0.36 mmol) in THF (0.76 mL) and CS₂ (0.18 mL) was added triphenylphosphine (123 mg, 0.47 mmol) and the reaction mixture was stirred at rt for 48 h. The crude reaction mixture was concentrated and purified by silica gel chromatography by 0-20 EtOAc/Hexanes gradient elution to afford 1-(10-isothiocyanatodecyl)-2-(trifluoromethyl)benzene as an oily solid (53 mg, 86%): ¹H NMR (500 MHz, CDCl₃) δ ppm 7.6 (d, J=7.8 Hz, 1H), 7.45 (t, J=7.3 Hz, 1H), 7.32 (d, J=7.8 Hz, 1H), 7.27 (t, J=7.8 Hz, 1H), 3.51 (t, J=6.6 Hz, 2H), 2.76 (t, J=8.3 Hz, 2H), 1.69 (quin, J=6.8 Hz, 2H), 1.61 (quin, J=8.0 Hz, 2H), 1.29-1.43 (m, 12H).

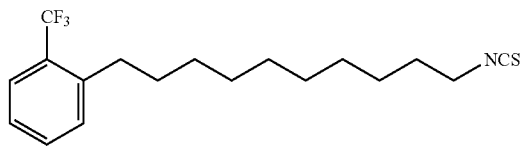

Example 17

1-(10-Isothiocyanatodecyl)-4-methoxybenzene: ¹H NMR (500 MHz, CDCl₃) δ ppm 7.09 (d, J=8.8 Hz, 2H), 6.84 (d, J=8.3 Hz, 2H), 3.79 (s, 3H), 3.50 (t, J=6.6 Hz, 2H), 2.54 (t, J=7.8 Hz, 2H), 1.69 (quin, J=7.3 Hz, 2H), 1.57 (quin, J=7.3 Hz, 2H), 1.40 (m, 2H), 1.25-1.33 (m, 10H).

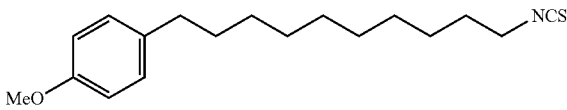

Example 18

2-(10-Isothiocyanatodecyl)pyridine: ¹H NMR (500 MHz, CDCl₃) δ ppm 8.52 (d, J=4.9 Hz, 1H), 7.58 (td, J=7.6, 2.0

Hz, 1H), 7.14 (d, J=7.8 Hz, 1H), 7.09 (dd, J=5.4, 7.3 Hz, 1H), 3.50 (t, J=6.6 Hz, 2H), 2.78 (t, J=7.8 Hz, 2H), 1.65-1.76 (m, 4H), 1.26-1.43 (m, 10H).

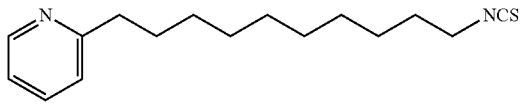

Example 19

4-(10-Isothiocyanatodecyl)pyridine: ¹H NMR (500 MHz, CDCl₃) δ ppm 8.48 (bs, 2H), 7.11 (bs, 2H), 3.40 (t, J=6.6 Hz, 2H), 2.6 (t, J=7.33 Hz, 2H), 1.85 (quin, J=7.33 Hz, 2H), 1.56-1.66 (m, 2H), 1.25-1.45 (m, 12H).

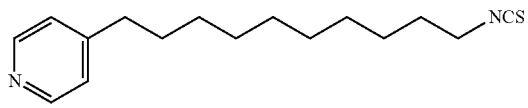

Example 20

2-(10-Isothiocyanatodecyl)pyrimidine: ¹H NMR (500 MHz, CDCl₃) δ ppm 8.67 (d, J=5.1 Hz, 2H), 7.12 (t, J=4.8 Hz, 1H), 4.05 (t, J=6.6 Hz, 2H), 2.96 (t, 7.3 Hz, 2H), 1.83 (quin, J=8.0 Hz, 2H), 1.61 (quin, J=7.3 Hz, 2H), 1.25-1.40 (m, 10H).

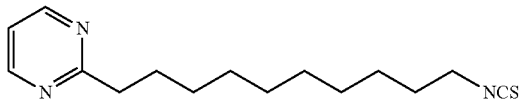

Example 21

(11-Isothiocyanatoundecyl)benzene: ¹H NMR (500 MHz, CDCl₃) δ ppm 7.25-7.27 (m, 2H), 7.14-7.20 (m, 3H), 3.50 (t, J=6.6 Hz, 2H), 2.60 (t, J=8.1 Hz, 2H), 1.69 (quin, J=7.3 Hz, 2H), 1.61 (quin, J=7.3 Hz, 2H), 1.24-1.43 (m, 12H).

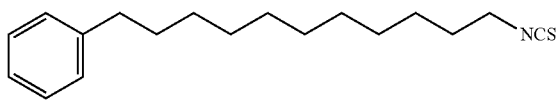

Example 22

(9-Isothiocyanatononyl)benzene: ¹H NMR (500 MHz, CDCl₃) δ ppm 7.24-7.29 (m, 2H), 7.14-7.19 (m, 3H), 3.47 (t, J=6.8 Hz, 2H), 2.60 (t, J=7.8 Hz, 2H), 1.66 (quin, J=6.8 Hz, 2H), 1.61 (quin, J=7.3 Hz, 2H), 1.26-1.41 (m, 10H).

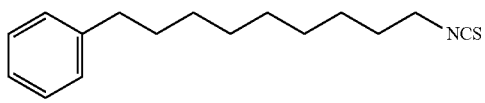

Method D.

Commercial alcohols were deprotonated using a strong base like NaH and alkylated with bromopropionitrile or bromoacetonitrile in dimethylformamide. Reduction of these nitriles to primary amines using a reducing agent such as LiAlH₄ in the presence of aluminum trichloride (Scheme 4). These were then converted to the desired isothiocyanates using techniques described in Method B.

Scheme 4:

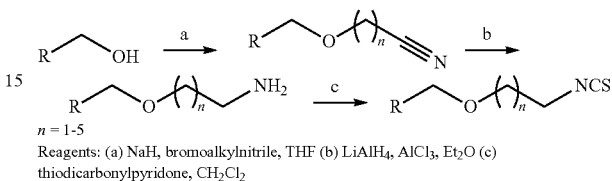

n = 1-5
Reagents: (a) NaH, bromoalkylnitrile, THF (b) LiAlH₄, AlCl₃, Et₂O (c) thiodicarbonylpyridone, CH₂Cl₂

The following examples were prepared according to Method D.

Example 23

Step 1. 2-(2-(2-(Benzyloxy)ethoxy)ethoxy)acetonitrile. To a stirring solution of diethylene glycol benzyl ether (1.0 g, 5.1 mmol) in THF (10 mL) at 0° C., was added in small portions NaH (408 mg, 10.2 mmol), then the reaction mixture was warmed to rt and stirred for 30 mins. The reaction mixture was cooled to 0° C., and bromoacetonitrile (0.39 mL, 5.6 mmol) was added dropwise and stirred for 3 h. The reaction was quenched with saturated ammonium chloride, and extracted with EtOAc (3×50 mL). The combined organic phase was washed with brine, dried over magnesium sulfate, filtered and concentrated. The crude residue was further purified by silica gel chromatography using 25% acetone/hexanes eluent to afford 2-(2-(2-(benzyloxy)ethoxy)ethoxy)acetonitrile as a colorless oil (437 mg, 37%): ¹H NMR (500 MHz, CDCl₃) δ ppm 7.35 (d, J=4.9 Hz, 4H), 7.27-7.32 (m, 1H), 4.57 (s, 2H), 4.33 (s, 2H), 3.76-3.80 (m, 2H), 3.67-3.74 (m, 4H), 3.62-3.66 (m, 2H).

Step 2. 2-(2-(2-(Benzyloxy)ethoxy)ethoxy)ethan-1-amine. To a stirring suspension of LiAlH₄ (66 mg, 1.73 mmol) in Et₂O (7.5 mL) was added dropwise a solution of AlCl₃ (300 mg, 2.25 mmol) in Et₂O (7.5 mL) and stirred 10 mins at rt, then a solution of 2-(2-(2-(benzyloxy)ethoxy)ethoxy)acetonitrile (408 mg, 1.73 mmol) in Et₂O (10 mL) was added dropwise and stirred at rt 2 h. The reaction was cooled to 0° C. and quenched with 3 M HCl (50 mL) dropwise and stirred 1 h. The crude reaction mixture was washed with Et₂O (50 mL), basified with NaOH pellets and potassium sodium tartrate, extracted with DCM (3×50 mL). The combined organic phase was washed with brine, dried over sodium sulfate, filtered and concentrated to afford 2-(2-(2-(benzyloxy)ethoxy)ethoxy)ethan-1-amine as a clear colorless oil (392 mg, 95%): ¹H NMR (500 MHz, CDCl₃) δ ppm 7.32-7.35 (m, 4H), 7.25-7.30 (m, 1H), 4.57 (s, 2H), 3.59-3.72 (m, 10H), 3.50 (t, J=5.4 Hz, 2H), 2.85 (bs, 2H).

Step 3. ((2-(2-(2-Isothiocyanatoethoxy)ethoxy)ethoxy)methyl)benzene. To a stirring solution of 2-(2-(2-(benzyloxy)ethoxy)ethoxy)ethan-1-amine (113 mg, 0.42 mmol) in DCM (4.2 mL) at 0° C. was added thiocarbonyldipyridone (290 mg, 1.25 mmol), and the reaction mixture was warmed to rt and stirred for 2 h. The crude reaction mixture was concentrated and purified by silica gel chromatography using 10% acetone/hexanes eluent to afford ((2-(2-(2-isothiocyanatoethoxy)ethoxy)ethoxy)methyl)benzene as clear colorless oil (80 mg, 68%): $^1$H NMR (500 MHz, CDCl$_3$) δ ppm 7.34-7.39 (m, 4H), 7.26-7.33 (m, 1H), 4.60 (s, 2H), 3.60-3.75 (m, 12H).

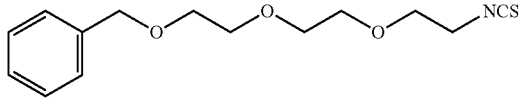

Example 24

3-((3-Isothiocyanatopropoxy)methyl)-1,1'-biphenyl: $^1$H NMR (500 MHz, CDCl$_3$) δ ppm 7.6 (dd, J=1.5, 7.3 Hz, 2H), 7.55 (s, 1H), 7.53 (d, J=7.8 Hz, 1H), 7.41-7.47 (m, 3H), 7.36 (app tt, J=2.0, 7.3 Hz, 1H), 7.32 (d, J=7.8 Hz, 1H), 4.59 (s, 2H), 3.68 (t, J=6.3 Hz, 2H), 3.63 (t, J=5.9 Hz, 2H), 1.99 (quin, J=6.0 Hz, 2H).

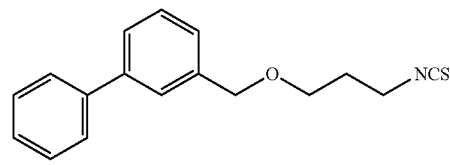

Example 25

4-((3-Isothiocyanatopropoxy)methyl)-1,1'-biphenyl: $^1$H NMR (500 MHz, CDCl$_3$) δ ppm 7.57-7.61 (m, 4H), 7.42-7.46 (m, 2H), 7.40 (d, J=7.8 Hz, 2H), 7.34 (app tt, J=1, 7.3 Hz, 1H), 4.56 (s, 2H), 3.68 (t, J=6.3 Hz, 2H), 3.61 (t, J=5.6 Hz, 2H), 1.98 (quin, J=6.1 Hz, 2H).

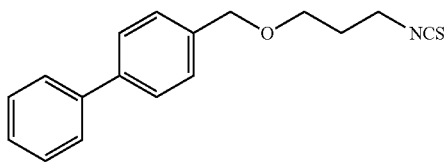

Example 26

1((3-Isothiocyanatopropoxy)methyl)-4-phenoxybenzene: $^1$H NMR (500 MHz, CDCl$_3$) δ ppm 7.25-7.40 (m, 5H), 6.98-7.15 (m, 4H), 4.49 (s, 2H), 3.67 (t, J=6.8 Hz, 2H), 3.60 (t, J=5.9 Hz, 2H), 1.98 (quin, J=6.8 Hz, 2H).

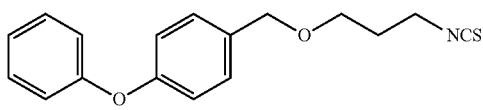

Method E.

Alkylation of 4-benzylpiperidine with bromovaleronitrile, followed by hydride reduction in the presence of a aluminum chloride followed by basic workup gave aminoalkyl-benzylpiperidine (Scheme 5). Acylation with 1,1-thiodicarbonylpyridin-2(1H)-one at rt gave the desired isocyanatobenzylpiperidine.

Scheme 5:

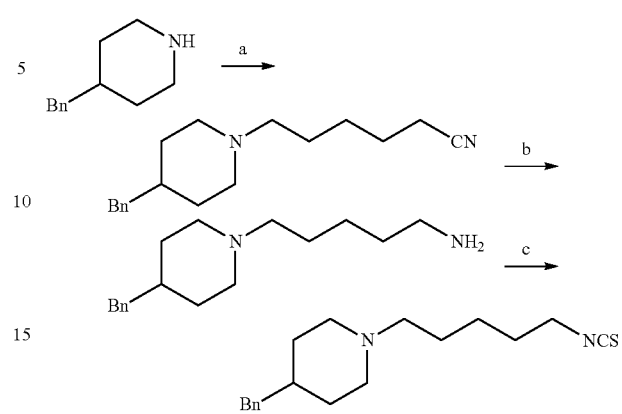

Reagents: (a) bromovaleronitrile, K$_2$CO$_3$, MeCN (b) LiAlH$_4$, AlCl$_3$, Et$_2$O (c) 1,1-thiodicarbonylpyridin-2(1H)-one, CH$_2$Cl$_2$ The following examples were prepared according to Method E.

Example 27

Step 1. 6-(4-Benzylpiperidin-1-yl)hexanenitrile. A solution of 4-benzylpiperidine (176 mg, 1.0 mmol), bromovaleronitrile (162 mg, 1.0 mmol) and potassium carbonate (276 mg, 2.0 mmol) in acetonitrile (3 mL) was heated to 70° C. for 18 h. The reaction mixture was cooled to rt, quenched with sat. NaHCO$_3$, and extracted with EtOAc (3×). The organic extracts were washed with brine, and dried over sodium sulfate. The reaction mixture was concentrated under reduced pressure, and the residue was purified by silica gel chromatography eluting with acetone to afford 6-(4-benzylpiperidin-1-yl)hexanenitrile as an oily solid (256 mg, 95%): $^1$H NMR (500 MHz, CDCl$_3$) δ ppm 7.27 (t, J=7.3 Hz, 2H), 7.16-7.21 (m, 1H), 7.14 (d, J=7.3 Hz, 2H), 2.86 (d, J=11.2 Hz, 2H), 2.53 (d, J=7.3 Hz, 2H), 2.37 (t, J=6.9 Hz, 2H), 2.31 (t, J=7.1 Hz, 2H), 1.84 (td, J=2, 11.7 Hz, 2H), 1.59-1.72 (m, 7H), 1.51 (dtd, J=15, 7.5, 3.7 Hz, 1H), 1.23-1.33 (m, 2H).

Step 2. 5-(4-Benzylpiperidin-1-yl)pentan-1-amine. To a stirring suspension of LiAlH$_4$ (18 mg, 0.48 mmol), in Et$_2$O (1.5 mL) was added dropwise a solution of AlCl$_3$ (83 mg, 0.45 mmol) in Et$_2$O (3 mL), then a solution of 6-(4-benzylpiperidin-1-yl)hexanenitrile (122 mg, 0.48 mmol) in Et$_2$O (4 mL) was added dropwise and the mixture stirred at rt for 2 h. The reaction mixture was poured over ice cold 6M HCl (50 mL), stirred 30 minutes, washed with Et$_2$O (50 mL). The aqueous phase was neutralized with KOH, then sodium potassium tartrate, stirred at rt 10 min, and extracted with Et$_2$O. The combined organic phase was washed with brine, dried over sodium sulfate and concentrated under reduced pressure to afford 5-(4-benzylpiperidin-1-yl)pentan-1-amine as a colorless oil (120 mg, 96%): $^1$H NMR (500 MHz, CDCl$_3$) δ ppm 7.27 (t, J=7.3 Hz, 2H), 7.16-7.21 (m, 1H), 7.14 (d, J=6.8 Hz, 2H), 2.95 (d, J=11.2 Hz, 2H), 2.71 (bs, 1H), 2.54 (d, J=6.8 Hz, 2H), 2.34 (t, J=8.3 Hz, 2H), 1.90 (t, J=11.5 Hz, 2H), 1.2-1.7 (m, 12H).

Step 3. 4-Benzyl-1-(5-isothiocyanatopentyl)piperidine. To a stirring solution of 5-(4-benzylpiperidin-1-yl)pentan-1-amine (28.5 mg, 0.096 mmol) in DCM (3 mL) at 0° C. was added 1,1-thiodicarbonylpyridin-2(1H)-one (67 mg, 0.29 mmol). The reaction mixture was allowed to warm to rt and stirred for 2 h. The reaction mixture was concentrated and purified by silica gel chromatography eluting with 50-100% EtOAc/hexanes to afford 4-benzyl-1-(5-isothiocyanatopentyl)piperidine as an colorless oil (19 mg, 65%): $^1$H NMR (500 MHz, CDCl$_3$) δ ppm 7.27 (t, J=7.3 Hz, 2H), 7.18 (t, J=7.3 Hz, 1H), 7.14 (d, J=8.3 Hz, 2H), 3.5 (t, J=6.6 Hz, 2H), 2.88 (d, J=11.7 Hz, 2H), 2.53 (d, J=7.3 Hz, 2H), 2.29 (t, J=7.8 Hz, 2H), 1.85 (t, J=11.7 Hz, 2H), 1.71 (quin, J=7.8 Hz, 2H), 1.64 (d, J=12.7 Hz, 2H), 1.37-1.56 (m, 4H), 1.25-1.36 (m, 2H).

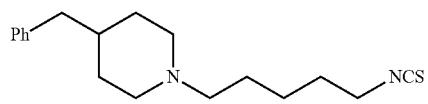

Method F.

Cyclobutane-isothiocyanates 10 and 11 were prepared according to Scheme 6. 3-Oxocyclobutane-1-carboxylic acid 1 was first converted to acyl chloride 2 with thionyl chloride, which upon application of the Curtius Reaction protocol (NaN$_3$), afforded amine 3. Masking of amine with di-tert-butyl dicarbonate and reduction of ketone 4 with NaBH$_4$ produced isomeric alcohol mixtures 5 in 4:1 cis/trans ratio. The preparation of the cis-isomer 6 was accomplished upon reduction with L-selectride at low temperature (−78° C.). Coupling of hydroxy-cyclobutane 5 with an aryl-alkyl bromide (e.g. 1-bromo-4-(bromomethyl)benzene) was accomplished upon treatment with a base such as sodium hydride in an aprotic polar solvent as tetrahydrofuran. Palladium mediated cross-coupling reaction between aryl-bromide 7 and the appropriate boronic acid was used to generate the biphenyl-type analogs 8. Palladium catalysts suitable for use in the process of the disclosure include Pd(0) or Pd(II) catalysts such as dichlorobis(tri-o-tolylphosphine)palladium (II), tetrakis(triphenylphosphine)palladium(0), or the like. Inorganic bases suitable for use in the inventive process include Na or K hydroxides, carbonates or bicarbonates, preferably Na$_2$CO$_3$ or K$_2$CO$_3$. Solvents suitable for use in the inventive process include polar or non-polar organic solvents such as toluene, dioxane. Unmasking of the amino-group of 8 was achieved upon treatment with an organic strong acid as trifluoroacetic acid in a chlorinated solvent such as dichloromethane. Generation of the isothiocyanates 10 and 11 was accomplished upon treatment with 1,1'-thiocarbonyldi-2(1H)-pyridone and an organic base such as triethylamine in an inert solvent as dichloromethane.

Scheme 6:

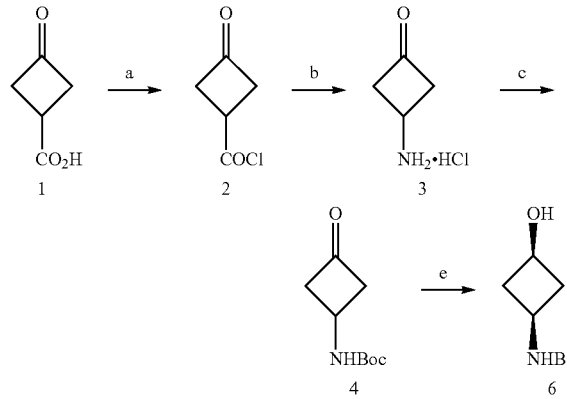

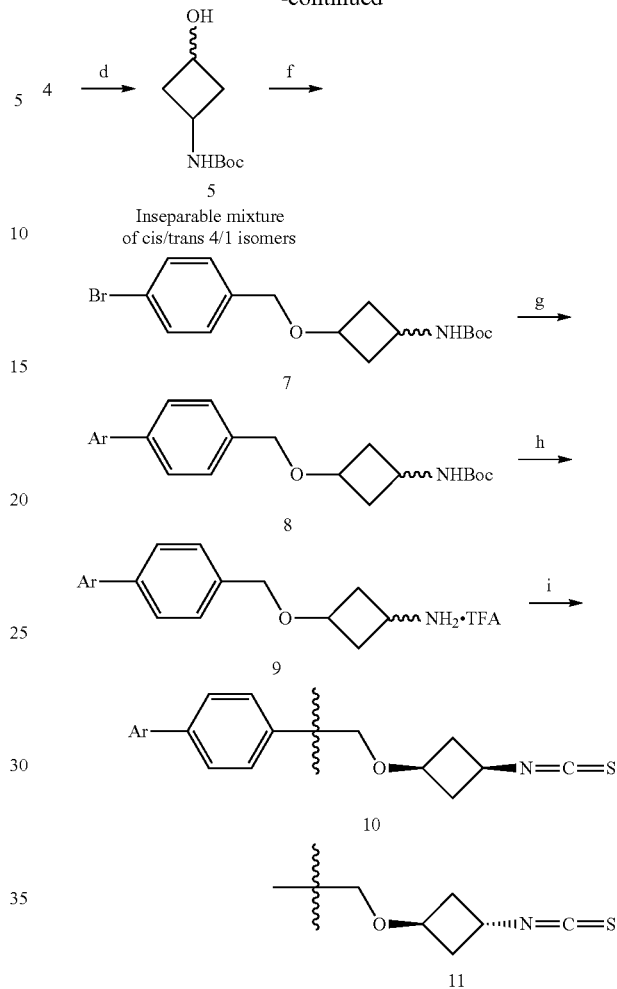

Reagents: (a) SOCl$_2$, benzene; (2) NaN$_3$, benzene, H$_2$O, HCl; (c) (Boc)$_2$O, Et$_3$N; (d) NaBH$_4$, MeOH; (e) L-Selectride, NaOH, 30% H$_2$O$_2$; (f) 4-Br-benzyl bromide, NaH, THF; (g) Ar—B(OH)$_2$, K$_2$CO$_3$, Pd(PPh$_3$)$_4$, dioxane, H$_2$O; (h) TFA, CH$_2$Cl$_2$; (i) 1,1'-thiocarbonyldi-2(1H)-pyridone, Et$_3$N, CH$_2$Cl$_2$ The following examples were prepared according to Method F.

Example 28

4-(((1R,3R)-3-Isothiocyanatocyclobutoxy)methyl)-4'-methyl-1,1'-biphenyl: $^1$H NMR (500 MHz, CDCl$_3$) δ ppm 7.57 (d, J=8.0 Hz, 2H), 7.49 (d, J=7.5 Hz, 2H), 7.37 (d, J=8.0 Hz, 2H), 7.25 (d, J=7.5 Hz, 2H), 4.44 (s, 2H), 4.37-4.34 (m, 1H), 4.31-4.27 (m, 1H), 2.51-2.48 (m, 4H), 2.39 (s, 3H).

Step 1. 3-Oxocyclobutane-1-carbonyl chloride. To a mixture of 3-oxocyclobutane-1-carboxylic acid (4.0 g, 35.09 mmol) and benzene (40 mL) was added thionyl chloride (7.6 mL, 105.3 mmol) and the mixture was stirred at 70° C. for 18 hours. The volatiles were removed under vacuum and then benzene (20 mL) was added twice and removed under vacuum to remove excess thionyl chloride. The residue was distilled to afford 3-oxocyclobutane-1-carbonyl chloride as oil (3.7 g). $^1$H NMR (500 MHz, CDCl$_3$) δ ppm 3.27-3.68 (m, 1H), 3.58-3.52 (m, 2H), 3.45-3.38 (m, 2H).

Step 2. 3-Aminocyclobutan-1-one hydrochloride. To a cold (0° C.) mixture of 3-oxocyclobutane-1-carbonyl chloride (1.0 g, 7.54 mmol)) and benzene (10 mL) was added a solution of sodium azide (0.98 g, 15.1 mmol) in water 10 mL. The mixture was allowed to come to room temperature and stirred for 2 hours. The organic layer was separated, washed with saturated aqueous NaHCO$_3$ and dried over MgSO$_4$. The organic layer was slowly heated to 60° C. and stirred for an additional 1 hour. The mixture cooled to room temperature and HCl (20%, 10 mL) was added and the mixture was heated at 90° C. for 18 hours. Then, the aqueous layer was separated and the organic layer was washed with water. The combined aqueous layer was concentrated under vacuum to give 3-aminocyclobutan-1-one hydrochloride as a white solid (0.75 g, 81.8% yield). The product was carried to the next step without any further purification.

Step 3. tert-Butyl (3-oxocyclobutyl)carbamate. Di-tert-butyl dicarbonate (1.61 g, 7.41 mmol) was added into a cold (0° C.) mixture of 3-aminocyclobutan-1-one hydrochloride (750 mg, 6.17 mmol), DMF (10 mL) and Et$_3$N (1.28 mL, 9.25 mmol). The mixture was allowed to come to room temperature and stirred for 4 hours. The mixture poured into water and extracted (3×) with EtOAc. The organics were dried over anhydrous MgSO4. The solvents were removed under vacuum and the residue was purified on silica gel (Biotage; eluting solvents hexanes: EtOAc 3/1 ratio) to afford tert-butyl (3-oxocyclobutyl)carbamate as white solid (980 mg, 86.2% yield). $^1$H NMR (500 MHz, CDCl$_3$) δ ppm 4.89 (brs, 1H), 4.25 (brs, 1H), 3.42-3.57 (m, 2H), 3.06-3.0 (m, 2H), 1.43 (s, 9H).

Step 4. tert-Butyl (3-hydroxycyclobutyl)carbamate. To a cold (0° C.) mixture of tert-butyl (3-oxocyclobutyl)carbamate (620 mg, 3.35 mmol) in MeOH (10 mL) was added NaBH$_4$ (126.7 mg, 3.35 mmol) portionwise over 20 minutes. The mixture was stirred for 30 additional minutes and then it was poured into cold water. The mixture was extracted with EtOAc (3×) and the organics were dried over anhydrous MgSO$_4$. The solvents were removed under vacuum and the residue was purified on silica gel (Biotage; eluting solvents hexanes: EtOAc 1/1 ratio) to afford tert-butyl (3-hydroxycyclobutyl)carbamate (4/1 cis/trans isomeric ratio) as white solid (590 mg, 95% yield). The cis/trans isomers 4/1 ratio were inseparable and carried to the next step. $^1$H NMR (500 MHz, CDCl$_3$) δ ppm [4.64 (brs), 4.22 (brs) (1H)], [4.47 (m), 4.02 (m), 1H)], [3.66 (m), 2.77 (m), 2H], [2.31 (m), 2.22 (m), 2H], [1.39 (m), 1.79 (m), 2H], 1.43 (s, 9H).

Step 5. tert-Butyl (3-((4-bromobenzyl)oxy)cyclobutyl) carbamate. Sodium hydride (60% dispersion in mineral oil; 58.8 mg, 1.47 mmol) was added into a cold (0° C.) mixture of tert-butyl (3-hydroxycyclobutyl)carbamate (260 mg, 1.39 mmol) and anhydrous THF (5 mL). After stirring for 1 hour, 1-bromo-4-(bromomethyl)benzene (422 mg, 1.69 mmol) was added and the mixture was allowed to come to room temperature and stirred for 8 hours. Then, the mixture was poured into saturated aqueous ammonium chloride and extracted with ethyl acetate (2×). The organic extracts were dried over anhydrous MgSO$_4$. The solvents were removed under vacuum and the residue was purified on silica gel (Biotage; eluting solvents hexanes: EtOAc 4/1 ratio) to afford tert-butyl (3-((4-bromobenzyl)oxy)cyclobutyl)carbamate as oil (382 mg, 63.5% yield). $^1$H NMR (500 MHz, CDCl$_3$) δ ppm 7.47 (d, J=8.5 Hz, 2H), 7.2 (d, J=8.5 Hz, 2H), 4.61 (m, 1H), 4.35 (s, 2H), [4.16 (m), 3.76-3.7 (m), 2H], [2.71-2.7 (m), 2.41 (m), 2H], [2.14 (m), 1.82-1.76 (m), 2H], 1.43 (s, 9H).

Step 6. tert-Butyl (3-((4'-methyl-[1,1'-biphenyl]-4-yl) methoxy)cyclobutyl)carbamate. Into a microwave vessel were added tert-butyl (3-((4-bromobenzyl)oxy)cyclobutyl) carbamate (150 mg, 0.42 mmol), p-tolylboronic acid (114.2 mg, 0.84 mmol), K$_2$CO$_3$ (174 mg, 1.26 mmol), dioxane (8 mL) and water (2 mL). Argon gas was passed through the mixture for 10 minutes and then tetrakis(triphenylphosphine)palladium(0) (4.8 mg 0.0042 mmol) was added and the argon flow continued for 5 additional minutes. Then, the vessel was sealed and microwaved at 110° C. for 2 hours. The mixture was cooled to room temperature, diluted with EtOAc (30 mL) and washed with water and brine. The organics extracts were dried over anhydrous MgSO$_4$. The solvents were removed under vacuum and the residue was purified on silica gel (Biotage; eluting solvents hexanes: EtOAc 4/1 ratio) to afford tert-butyl (3-((4'-methyl-[1,1'-biphenyl]-4-yl)methoxy)cyclobutyl)carbamate as oil (123.8 mg, 80% yield). $^1$H NMR (500 MHz, CDCl$_3$) δ ppm 7.56 (dd, J=8.0 Hz, 2H), 7.49 (d, J=8.5 Hz, 2H), 7.38 (d, J=8.0 Hz, 2H), 7.25 (d, J=8.5 Hz, 2H), 4.61 (m, 1H), 4.43 (s, 2H), [4.27-4.21 (m), 3.79-3.57 (m) 2H], [2.72 (m), 2.42 (m), 2H], [2.18 (m), 1.85-1.79 (m), 2H], 1.43 (s, 9H).

Step 7. 3-((4'-Methyl-[1,1'-biphenyl]-4-yl)methoxy)cyclobutan-1-amine. TFA salt. Trifluoroacetic acid (0.25 mL, 3.26 mmol) was added into a mixture of tert-butyl (3-((4'-methyl-[1,1'-biphenyl]-4-yl)methoxy)cyclobutyl)carbamate (120 mg, 0.32 mmol) and CH$_2$Cl$_2$ (5 mL). The mixture was stirred at room temperature for 5 h and then the volatiles were removed under vacuum. The residue was successively taken (3×) in CHCl$_3$ (10 mL) and the volatiles were removed under vacuum to ensure removal of excess TFA. The crude 3-((4'-methyl-[1,1'-biphenyl]-4-yl)methoxy)cyclobutan-1-amine TFA (122 mg) was carried to the next step.

Step 8. 4-(((1R,3R)-3-isothiocyanatocyclobutoxy) methyl)-4'-methyl-1,1'-biphenyl and 4-(((1S,3S)-3-isothiocyanatocyclobutoxy)methyl)-4'-methyl-1,1'-biphenyl. Trimethylamine (0.33 mL, 2.35 mmol) was added into a mixture of 3-((4'-methyl-[1,1'-biphenyl]-4-yl)methoxy)cyclobutan-1-amine. TFA (122 mg, 0.32 mmol), and CH$_2$Cl$_2$ (5 mL). After stirring for 10 minutes 1,1'-thiocarbonyldi-2(1H)-pyridone (222.7 mg, 0.96 mmol) was added and the mixture was stirred at room temperature for 2 h. The mixture was diluted in EtOAc (30 mL) and washed with water and brine. The organics extracts were dried over anhydrous MgSO$_4$. The solvents were removed under vacuum and the residue was purified on silica gel (Biotage; eluting solvents hexanes: EtOAc 15/1 ratio) to afford 4-(((1R,3R)-3-isothiocyanatocyclobutoxy)methyl)-4'-methyl-1,1'-biphenyl as oil (12.6 mg), $^1$H NMR (500 MHz, CDCl$_3$) δ ppm 7.57 (d, J=8.0 Hz, 2H), 7.49 (d, J=7.5 Hz, 2H), 7.37 (d, J=8.0 Hz, 2H), 7.25 (d, J=7.5 Hz, 2H), 4.44 (s, 2H), 4.37-4.34 (m, 1H), 4.31-4.27 (m, 1H), 2.51-2.48 (m, 4H), 2.39 (s, 3H), and (((1S,3S)-3-isothiocyanatocyclobutoxy)methyl)-4'-methyl-1,1'-biphenyl (79.8 mg), $^1$H NMR (500 MHz, CDCl$_3$) δ ppm 7.57 (d, J=7.5 Hz, 2H), 7.49 (d, J=8.5 Hz, 2H), 7.37 (d, J=7.5 Hz, 2H), 7.25 (d, J=8.5 Hz, 2H), 4.45 (s, 2H), 3.81-3.78 (m, 1H), 3.71-3.68 (m, 1H), 2.82-2.76 (m, 2H), 2.39 (s, 3H), 2.33-2.27 (m, 2H).

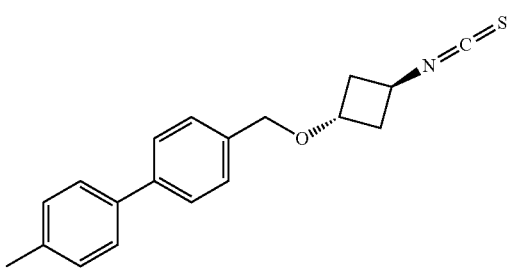 [SMILES: Cc1ccc(-c2ccc(CO[C@H]3C[C@H](N=C=S)C3)cc2)cc1]

The following examples were prepared according to Method F.

Example 29

4-(((1S,3S)-3-Isothiocyanatocyclobutoxy)methyl)-4'-methyl-1,1'-biphenyl: $^1$H NMR (500 MHz, CDCl$_3$) δ ppm 7.57 (d, J=7.5 Hz, 2H), 7.49 (d, J=8.5 Hz, 2H), 7.37 (d, J=7.5 Hz, 2H), 7.25 (d, J=8.5 Hz, 2H), 4.45 (s, 2H), 3.81-3.78 (m, 1H), 3.71-3.68 (m, 1H), 2.82-2.76 (m, 2H), 2.39 (s, 3H), 2.33-2.27 (m, 2H).

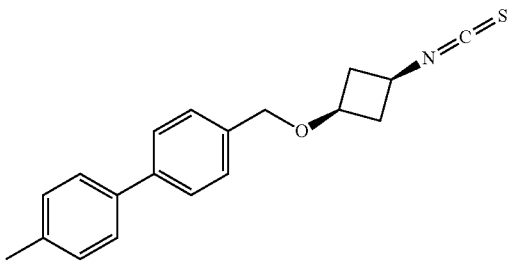 [SMILES: Cc1ccc(-c2ccc(CO[C@H]3C[C@@H](N=C=S)C3)cc2)cc1]

Example 30

4-(((1R,3R)-3-isothiocyanatocyclobutoxy)methyl)-1,1'-biphenyl: $^1$H NMR (500 MHz, CDCl$_3$) δ ppm 7.59-7.57 (m, 4H), 7.44 (t, J=7.5 Hz, 2H), 7.39-7.34 (m, 3H), 4.45 (s, 2H), 4.39-4.34 (m, 1H), 4.31-4.27 (m, 1H), 2.52-2.48 (m, 4H).

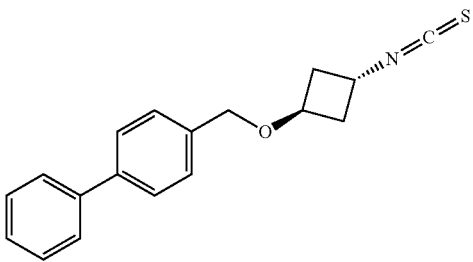 [SMILES: S=C=N[C@H]1C[C@H](OCc2ccc(-c3ccccc3)cc2)C1]

Example 31

4-(((1S,3S)-3-isothiocyanatocyclobutoxy)methyl)-1,1'-biphenyl. $^1$H NMR (500 MHz, CDCl$_3$) δ ppm 7.59-7.57 (m, 4H), 7.46 (t, J=8.5 Hz, 2H), 7.4-7.32 (m, 3H), 4.46 (s, 2H), 3.83-3.77 (m, 1H), 3.74-3.68 (m, 1H), 2.82-2.77 (m, 2H), 2.34-2.27 (m, 2H).

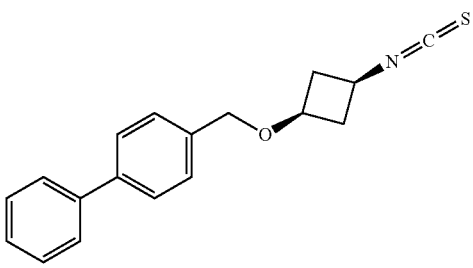 [SMILES: S=C=N[C@H]1C[C@@H](OCc2ccc(-c3ccccc3)cc2)C1]

The following examples were prepared according to Method F with the modification of using L-Selectride for the reduction of ketone 4 (Scheme 5) to obtain the cis product 6.

Example 32

3,4'-Difluoro-4-(((1S,3S)-3-isothiocyanatocyclobutoxy)methyl)-1,1'-biphenyl. Step 1. tert-Butyl ((1S,3S)-3-hydroxycyclobutyl)carbamate (L-Selectride reduction). To a cold (−78° C.) mixture of tert-butyl (3-oxocyclobutyl)carbamate (2 g, 10.8 mmol) in THF (20 mL) was added L-selectride (1M in THF, 16.2 mL, 16.2 mmol) dropwise over 30 minutes. The mixture was stirred for 1 hour and then a solution of NaOH (0.66 g) in water (6 mL) was added dropwise over 15 minutes, followed with the addition of H$_2$O$_2$ (30%, 6 mL) dropwise over 20 minutes. The mixture was allowed to come to room temperature, diluted with EtOAc (100 mL) and washed with Na$_2$SO$_3$ (10%) and brine. The organic extracts were dried over anhydrous MgSO$_4$. The solvents were removed under vacuum and the residue was purified on silica gel (Biotage; eluting solvents hexanes:EtOAc 1/1 ratio) to afford tert-butyl ((1S,3S)-3-hydroxycyclobutyl)carbamate as white solid (1.49 mg, 74% yield). $^1$H NMR (500 MHz, CDCl$_3$) δ ppm 4.64 (brs, 1H), 4.05-3.99 (m, 1H), 3.67-3.66 (m, 1H), 2.77-2.74 (m, 2H), 1.94 (m, 1H), 1.82-1.78 (m, 2H), 1.43 (s, 9H).

Step 2. tert-Butyl ((1S,3S)-3-((4-bromo-2-fluorobenzyl)oxy)cyclobutyl)carbamate. Sodium hydride (60% dispersion in mineral oil; 51.2 mg, 1.28 mmol) was added into a cold (0° C.) mixture of tert-butyl ((1S,3S)-3-hydroxycyclobutyl)carbamate (200 mg, 1.07 mmol) and anhydrous THF (3 mL). After stirring for 1 hour, 4-bromo-1-(bromomethyl)-2-fluorobenzene (294.6 mg, 1.1 mmol) was added and the mixture was allowed to come to room temperature and stirred for 8 hours. Then, the mixture was poured into saturated aqueous ammonium chloride and extracted with ethyl acetate (2×). The organic extracts were dried over anhydrous MgSO$_4$. The solvents were removed under vacuum and the residue was purified on silica gel (Biotage; eluting solvents hexanes:EtOAc 4/1 ratio) to afford tert-butyl ((1S,3S)-3-((4-bromo-2-fluorobenzyl)oxy)cyclobutyl)carbamate as oil (386.2 mg, 91% yield). $^1$H NMR (500 MHz, CDCl$_3$) δ ppm 7.27-7.21 (m, 3H), 4.61 (brs, 1H), 4.41 (s, 2H), 3.78-3.72 (m, 2H), 2.71 (m, 2H), 1.82-1.76 (m, 2H), 1.43 (s, 9H).

Step c. tert-Butyl ((1S,3S)-3-((3,4'-difluoro-[1,1'-biphenyl]-4-yl)methoxy)cyclobutyl) carbamate. Into a microwave vessel were added tert-butyl ((1S,3S)-3-((4-bromo-2-fluorobenzyl) oxy)cyclobutyl)carbamate (160 mg, 0.43 mmol), 4-fluorophenyl boronic acid (120.3 mg, 0.86 mmol), K$_2$CO$_3$ (178 mg, 1.29 mmol), dioxane (8 mL) and water (2 mL). Argon gas was passed through the mixture for 10 minutes and then tetrakis(triphenylphosphine)palladium(0) (5.0 mg 0.0043 mmol) was added and the argon flow continued for 5 additional minutes. Then, the vessel was sealed and microwaved at 110° C. for 2 hours. The mixture was diluted with EtOAc (30 mL) and washed with water and brine. The organics extracts were dried over anhydrous MgSO$_4$. The solvents were removed under vacuum and the residue was purified on silica gel (Biotage; eluting solvents hexanes:EtOAc 4/1 ratio) to afford tert-butyl ((1S,3S)-3-((3,4'-difluoro-[1,1'-biphenyl]-4-yl)methoxy)cyclobutyl) carbamate as oil (148 mg, 89.1% yield). $^1$H NMR (500 MHz, CDCl$_3$) δ ppm 7.53-7.5 (m, 2H), 7.44 (t, J=8.0 Hz, 1H), 7.31 (dd, J=8.0, 2.0 Hz, 1H), 7.23 (dd, J=11.0, 2.0 Hz, 1H), 7.14-7.11 (m, 2H), 4.66 (brs, 1H), 4.49 (s, 2H), 3.83-3.77 (m, 2H), 2.74 (m, 2H), 1.85-1.79 (m, 2H), 1.43 (s, 9H).

Step 4. (1S,3S)-3-((3,4'-Difluoro-[1,1'-biphenyl]-4-yl)methoxy)cyclobutan-1-amine. TFA. Trifluoroacetic acid (0.29 mL, 3.8 mmol) was added into a mixture of ((1S,3S)-3-((3,4'-difluoro-[1,1'-biphenyl]-4-yl)methoxy)cyclobutyl)carbamate (148 mg, 0.38 mmol) and CH$_2$Cl$_2$ (8 mL). The mixture was stirred at room temperature for 5 h and then the volatiles were removed under vacuum. The residue was taken (3×) successively in CHCl$_3$ (10 mL) and the volatiles were removed under vacuum to ensure removal of excess TFA. The crude (1S,3S)-3-((3,4'-difluoro-[1,1'-biphenyl]-4-yl)methoxy)cyclobutan-1-amine. TFA (153 mg) was carried to the next step.

Step 5. 3,4'-Difluoro-4-(((1S,3S)-3-isothiocyanatocyclobutoxy)methyl)-1,1'-biphenyl. Trimethylamine (0.16 mL, 1.14 mmol) was added into a mixture of (1S,3S)-3-((3,4'-difluoro-[1,1'-biphenyl]-4-yl)methoxy)cyclobutan-1-amine. TFA (153 mg, 0.38 mmol), and CH$_2$Cl$_2$ (7 mL). After stirring for 10 minutes 1,1'-thiocarbonyldi-2(1H)-pyridone (211.9 mg, 0.95 mmol) was added and the mixture was stirred at temperature for 2 h. The mixture was diluted in EtOAc (30 mL) and washed with water and brine. The organics extracts were dried over anhydrous MgSO$_4$. The solvents were removed under vacuum and the residue was purified on silica gel (Biotage; eluting solvents hexanes:EtOAc 15/1 ratio) to afford 3,4'-difluoro-4-(((1S,3S)-3-isothiocyanatocyclobutoxy)methyl)-1,1'-biphenyl as oil (98.6 mg, 78.5% yield). $^1$H NMR (500 MHz, CDCl$_3$) δ ppm 7.53-7.51 (m, 2H), 7.45 (t, J=8.0 Hz, 1H), 7.33 (dd, J=8.0, 1.5 Hz, 1H), 7.24 (dd, J=11.0, 1.5 Hz, 1H), 7.15-7.11 (m, 2H), 4.51 (s, 2H), 3.84-3.81 (m, 1H), 3.74-3.7 (m, 1H), 2.84-2.79 (m, 2H), 2.33-2.27 (m, 2H).

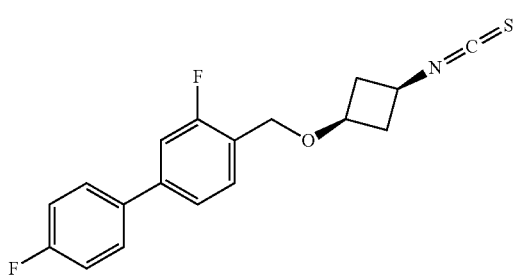 [SMILES: Fc1ccc(-c2ccc(CO[C@H]3C[C@@H](N=C=S)C3)c(F)c2)cc1]

Example 33

3,3'-Difluoro-4-(((1S,3S)-3-isothiocyanatocyclobutoxy)methyl)-4'-methoxy-1,1'-biphenyl: $^1$H NMR (500 MHz, CDCl$_3$) δ ppm 7.44 (t, J=7.5 Hz, 1H), 7.3 (m, 1H), 7.29-7.27 (m, 2H), 7.23 (dd, J=11.0, 2.0 Hz, 1H), 7.04 (t, J=8.5 Hz, 1H), 4.5 (s, 2H), 3.93 (s, 3H), 3.83-3.81 (m, 1H), 3.73-3.7 (m, 1H), 2.84-.78 (m, 2H), 2.33-2.27 (m, 2H).

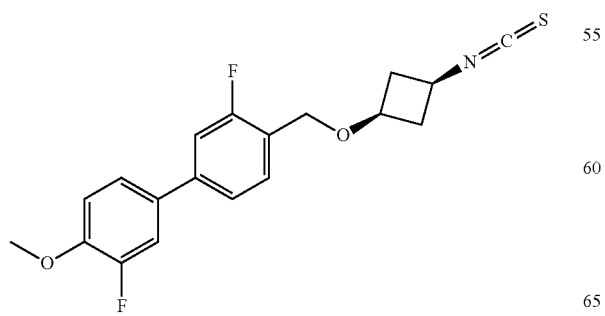

Example 34

4'-(((1R,3R)-3-isothiocyanatocyclobutoxy)methyl)-3-methoxy-1,1'-biphenyl: $^1$H NMR (500 MHz, CDCl$_3$) δ ppm 7.58 (dd, J=8.0, 2.0 Hz, 2H), 7.39 (d, J=8.0 Hz, 2H), 7.35 (d, J=7.5 Hz, 1H), 7.18 (dt, J=8.0, 1.0 Hz, 1H), 7.11 (t, J=2.0 Hz, 1H), 6.91 (dd, J=8.5, 2.5 Hz, 1H), 4.45 (s, 2H), 4.37-4.33 (m, 1H), 4.31-4.25 (m, 1H), 3.86 (s, 3H), 2.52-2.49 (m, 4H).

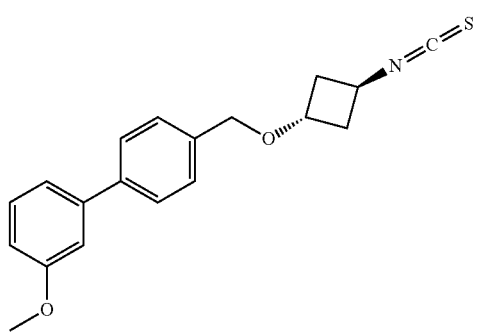 [SMILES: COc1cccc(-c2ccc(CO[C@H]3C[C@H](N=C=S)C3)cc2)c1]

Example 35

4'-(((1S,3S)-3-isothiocyanatocyclobutoxy)methyl)-3-methoxy-1,1'-biphenyl: $^1$H NMR (500 MHz, CDCl$_3$) δ ppm 7.58 (dd, J=8.0, 2.0 Hz, 2H), 7.39 (d, J=8.0 Hz, 2H), 7.35 (d, J=7.5 Hz, 1H), 7.18 (dt, J=8.0, 1.0 Hz, 1H), 7.11 (t, J=2.0 Hz, 1H), 6.91 (dd, J=8.5, 2.5 Hz, 1H), 4.46 (s, 2H), 3.86 (s, 3H), 3.81-3.78 (m, 1H), 3.72-3.68 (m, 1H), 2.82-2.77 (m, 2H), 2.33-2.27 (m, 2H).

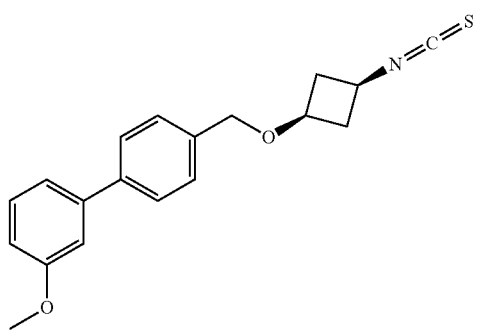 [SMILES: COc1cccc(-c2ccc(CO[C@H]3C[C@@H](N=C=S)C3)cc2)c1]

Example 36

4-Ethoxy-3,3'-difluoro-4'-(((1S,3S)-3-isothiocyanatocyclobutoxy)methyl)-1,1'-biphenyl: $^1$H NMR (500 MHz, CDCl$_3$) δ ppm 7.43 (t, J=7.5 Hz, 1H), 7.32 (d, J=2.0 Hz, 1H), 7.3 (m, 1H), 7.26-7.25 (m, 1H), 7.22 (dd, J=10.5, 2.0 Hz, 1H), 7.03 (t, J=8.0 Hz, 1H), 4.61 (m, 1H), 4.5 (s, 2H), 4.17 (q, J=6.5 Hz, 2H), 3.83-3.8 (m, 1H), 3.75-3.7 (m, 1H), 2.84-2.78 (m, 2H), 2.33-2.27 (m, 2H), 1.47 (t, J=6.5 Hz. 3H).

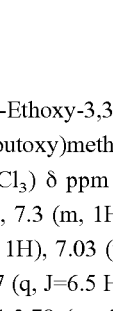

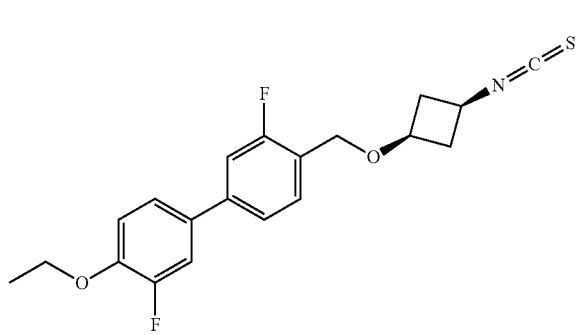 [SMILES: CCOc1ccc(-c2ccc(CO[C@H]3C[C@@H](N=C=S)C3)c(F)c2)cc1F]

Example 37

3,3'-Difluoro-4-isopropoxy-4'-(((1S,3S)-3-isothiocyanatocyclobutoxy)methyl)-1,1'-biphenyl: $^1$H NMR (500 MHz, CDCl$_3$) δ ppm 7.43 (t, J=7.5 Hz, 1H), 7.32-7.28 (m, 2H), 7.26-7.24 (m, 1H), 7.24 (dd, J=11.0, 2.0 Hz, 1H), 7.05 (t, J=7.0 Hz, 1H), 4.61 (m, 1H), 4.5 (s, 2H), 3.84-3.8 (m, 1H), 3.75-3.7 (m, 1H), 2.84-2.78 (m, 2H), 2.33-2.27 (m, 2H), 1.4 (s, 3H), 1.38 (s, 3H).

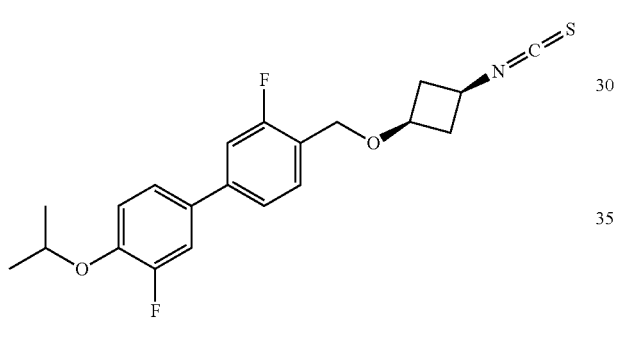

Example 38

6-(3-Fluoro-4-(((1S,3S)-3-isothiocyanatocyclobutoxy)methyl)phenyl)-2,3-dihydrobenzo[b][1,4]dioxine: $^1$H NMR (500 MHz, CDCl$_3$) δ ppm 7.42 (t, J=8.0 Hz, 1H), 7.3 (dd, J=7.5, 1.5 Hz, 1H), 7.22 (dd, J=9.5, 1.5 Hz, 1H), 7.08 (d, J=1.5 Hz, 1H), 7.06 (dd, J=8.5, 2.0 Hz, 1H), 6.93 (d, J=8.5 Hz, 1H), 4.49 (s, 2H), 4.3 (s, 4H), 3.82-3.79 (m, 1H), 3.73-3.69 (m, 1H), 2.83-2.78 (m, 2H), 2.33-2.27 (m, 2H).

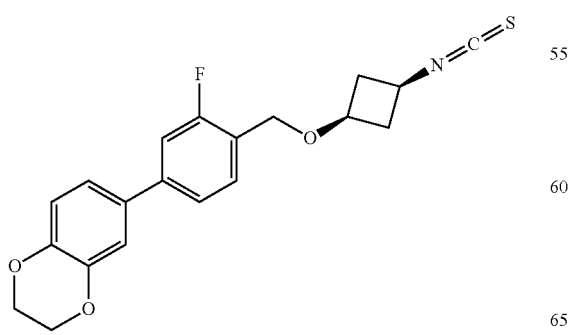

Example 39

5-(3-Fluoro-4-(((1S,3S)-3-isothiocyanatocyclobutoxy)methyl)phenyl)benzo[d][1,3]dioxole: $^1$H NMR (500 MHz, CDCl$_3$) δ ppm 7.42 (t, J=8.0 Hz, 1H), 7.3 (dd, J=8.0, 1.5 Hz, 1H), 7.21 (dd, J=11.5, 1.5 Hz, 1H), 7.05 (m, 2H), 6.89 (d, J=8.5 Hz, 1H), 6.01 (s, 2H), 4.49 (s, 2H), 3.85-3.80 (m, 1H), 3.73-3.7 (m, 1H), 2.84-2.78 (m, 2H), 2.33-2.27 (m, 2H).

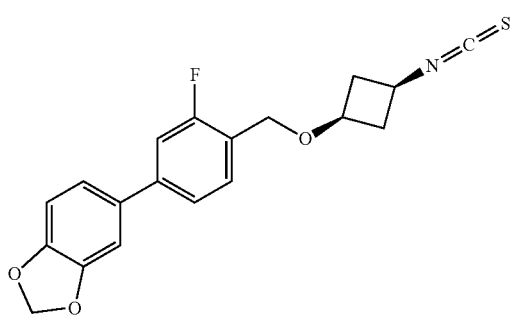 [SMILES: Fc1cc(-c2ccc3c(c2)OCO3)ccc1CO[C@H]1C[C@@H](N=C=S)C1]

Example 40

3-Fluoro-4-(((1S,3S)-3-isothiocyanatocyclobutoxy)methyl)-3',4'-dimethoxy-1,1'-biphenyl: $^1$H NMR (500 MHz, CDCl$_3$) δ ppm 7.42 (t, J=8.0 Hz, 1H), 7.35 (dd, J=8.0, 2.0 Hz, 1H), 7.25 (dd, J=11.5, 2.0 Hz, 1H), 7.14 (dd, J=8.0, 2.0 Hz, 1H), 7.07 (d, J=2.5 Hz, 1H), 6.95 (d, J=8.5 Hz, 1H), 4.51 (s, 2H), 3.95 (s, 3H), 3.93 (s, 3H), 3.87-3.81 (m, 1H), 3.73-3.7 (m, 1H), 2.84-2.78 (m, 2H), 2.33-2.27 (m, 2H).

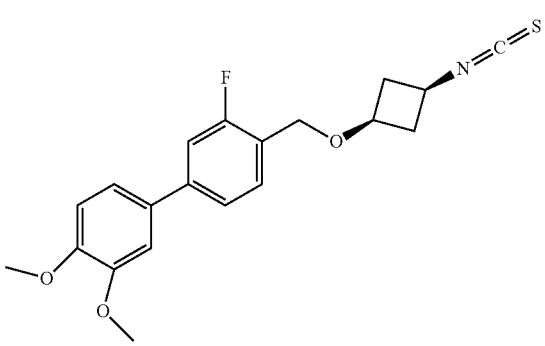 [SMILES: COc1ccc(-c2ccc(CO[C@H]3C[C@@H](N=C=S)C3)c(F)c2)cc1OC]

Example 41

3-(3-Fluoro-4-(((1R,3R)-3-isothiocyanatocyclobutoxy)methyl)phenyl)-2-methoxypyridine: $^1$H NMR (500 MHz, CDCl$_3$) δ ppm 8.18 (dd, J=5.0, 2.0, 1H), 7.61 (dd, J=7.0, 2.0, 1H), 7.44 (t, J=7.5 Hz, 1H), 7.34-7.3 (m, 2H), 6.98 (m, 1H), 4.51 (s, 2H), 3.98 (s, 3H), 3.86-3.81 (m, 1H), 3.78-3.70 (m, 1H), 2.85-2.79 (m, 2H), 2.34-2.28 (m, 2H).

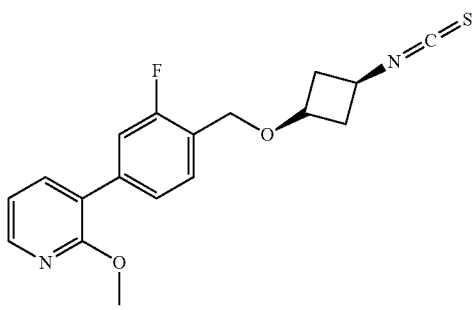

Example 42

5-(3-Fluoro-4-methoxyphenyl)-2-((((1R,3R)-3-isothiocyanatocyclobutoxy)methyl)pyridine: ¹H NMR (500 MHz, CDCl₃) δ ppm 7.54 (d, J=2.0 Hz, 1H), 7.84 (dd, J=8.0, 2.0, 1H), 7.48 (d, J=7.5 Hz, 1H), 7.33 (m, 2H), 7.08 (t, J=8.5 Hz, 1H), 4.57 (s, 2H), 3.95 (s, 3H), 3.92-3.86 (m, 1H), 3.78-3.71 (m, 1H), 2.86-2.83 (m, 2H), 2.36-2.33 (m, 2H).

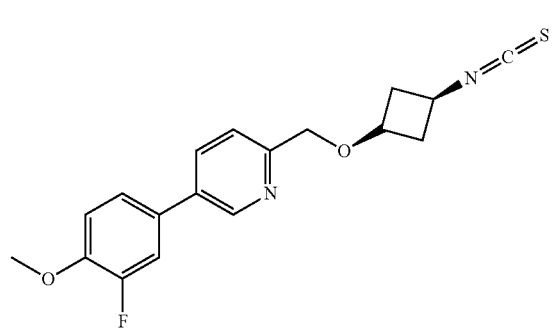

Example 43

3,4'-Difluoro-3'-((((1S,3S)-3-isothiocyanatocyclobutoxy)methyl)-4-methoxy-1,1'-biphenyl: ¹H NMR (500 MHz, CDCl₃) δ ppm 7.54 (dd, J=7.0, 2.0 Hz, 1H), 7.44-7.41 (m, 1H), 7.3-7.25 (m, 2H), 7.1 (t, J=9.0 Hz, 1H), 7.03 (t, J=8.5 Hz, 1H), 4.50 (s, 2H), 3.85-3.81 (m, 1H), 3.76-3.70 (m, 1H), 2.85-2.8 (m, 2H), 2.34-2.29 (m, 2H).

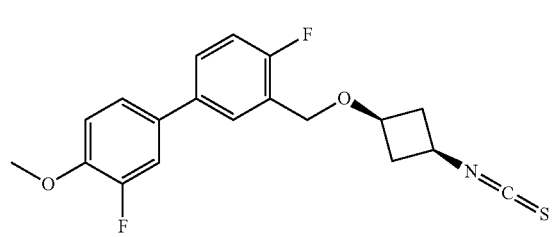 [SMILES: COc1ccc(-c2ccc(F)c(CO[C@H]3C[C@@H](N=C=S)C3)c2)cc1F]

Example 44

4-Bromo-2-fluoro-1-((((1R,3R)-3-isothiocyanatocyclobutoxy)methyl)benzene: ¹H NMR (500 MHz, CDCl₃) δ ppm 7.31-7.27 (m, 2H), 7.24 (dd, J=10.0, 2.0 Hz, 1H), 4.42 (s, 2H), 3.81-3.77 (m, 1H), 3.75-3.69 (m, 1H), 2.83-2.77 (m, 2H), 2.31-2.25 (m, 2H).

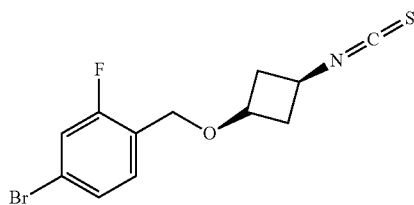

Example 45

4-(3-Fluoro-4-((((1R,3R)-3-isothiocyanatocyclobutoxy)methyl)phenyl)-3,5-dimethylisoxazole: ¹H NMR (500 MHz, CDCl₃) δ ppm 7.46 (t, J=7.5 Hz, 1H), 7.06 (dd, J=7.5, 2.0 Hz, 1H), 6.97 (dd, J=10.5, 2.0 Hz, 1H), 4.50 (s, 2H), 3.82-3.81 (m, 1H), 3.75-3.70 (m, 1H), 2.86-2.72 (m, 2H), 2.42 (s, 3H), 2.34-2.27 (m, 2H), 2.28 (s, 3H).

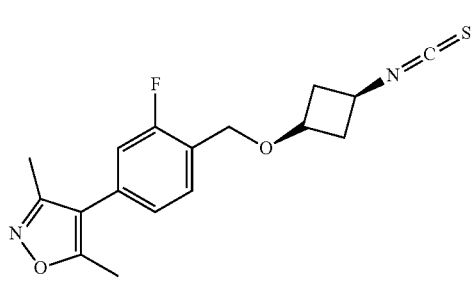

Example 46

4-(3-Fluoro-4-((((1R,3R)-3-isothiocyanatocyclobutoxy)methyl)phenyl)-1-methyl-1H-pyrazole: ¹H NMR (500 MHz, CDCl₃) δ ppm 7.74 (s, 1H), 7.61 (s, 1H), 7.34 (t, J=7.5 Hz, 1H), 7.24 (dd, J=8.0, 2.0 Hz, 1H), 7.15 (dd, J=11.0, 2.0 Hz, 1H), 4.46 (s, 2H), 3.95 (s, 3H), 3.83-3.81 (m, 1H), 3.75-3.71 (m, 1H), 2.86-2.75 (m, 2H), 2.34-2.28 (m, 2H).

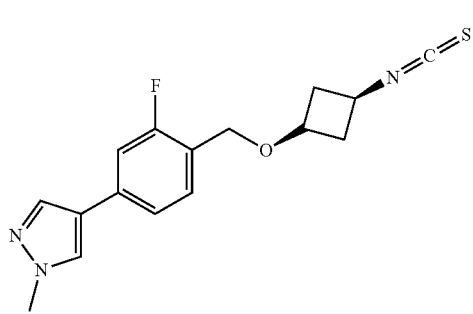

Example 47

3-Fluoro-4-((((1R,3R)-3-isothiocyanatocyclobutoxy)methyl)-3'-(trifluoromethyl)-1,1'-biphenyl: ¹H NMR (500 MHz, CDCl₃) δ ppm 7.8 (s, 1H), 7.75 (d, J=7.5 Hz, 1H), 7.64 (d, J=7.5 Hz, 1H), 7.57 (t, J=8.0 Hz, 1H), 7.49 (t, J=8.0 Hz, 1H), 7.39 (dd, J=7.5, 1.5 Hz, 1H), 7.3 (dd, J=10.5, 1.5 Hz, 1H), 4.53 (s, 2H), 3.83-3.81 (m, 1H), 3.75-3.71 (m, 1H), 2.86-2.8 (m, 2H), 2.34-2.28 (m, 2H).

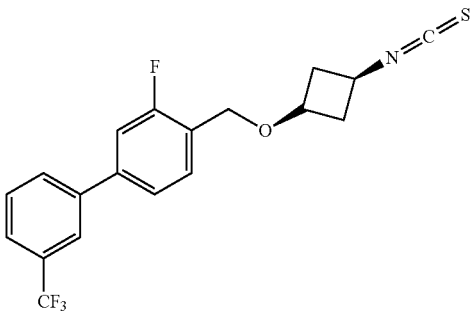

Example 48

3'-(Benzyloxy)-3-fluoro-4-(((1R,3R)-3-isothiocyanatocyclobutoxy)methyl)-1,1'-biphenyl: $^1$H NMR (500 MHz, CDCl$_3$) δ ppm 7.46-7.34 (m, 8H), 7.27 (dd, J=11.0, 1.5 Hz, 1H), 7.18-7.16 (m, 2H), 6.99 (dd, J=8.5, 2.5 HZ, 1H), 5.12 (s, 2H), 4.51 (s, 2H), 3.83-3.81 (m, 1H), 3.74-3.7 (m, 1H), 2.84-2.79 (m, 2H), 2.33-2.27 (m, 2H).

Method G.

The phenoxy cyclobutane isothiocyanates 7 and 11 were prepared according to Scheme 8. Coupling of benzaldehyde 1 with phenol using an inorganic base, as potassium carbonate, in a polar solvent, as N,N-dimethylformamide produced adduct 2, which was further reduced with sodium borohydride to give benzylic alcohol 3. Treatment of 3 with phosphorus tribromide, in an aprotic solvent as tetrahydrofuran produced benzyl bromide 4. Coupling of benzyl bromide 4 with tert-butyl 3-hydroxyazetidine-1-carboxylate was accomplished upon treatment with a base such as sodium hydride in an aprotic polar solvent as tetrahydrofuran to yield 5. Unmasking of the cyclobutane amino group of 5 to generate amine 6 was achieved upon treatment with a strong organic acid as trifluoroacetic acid in a chlorinated solvent such as dichloromethane. Cyclobutane isothiocyanate 7 was prepared from 6 upon treatment with 1,1'-thiocarbonyldi-2(1H)-pyridone and an organic base such as triethylamine in an inert solvent as dichloromethane. Furthermore, amine 6 was converted to amide 8 with trifluoroacetic anhydride. Palladium mediated cross-coupling reaction between amide 8 and the appropriate boronic acid was used to generate phenoxy analog 9. Palladium catalysts suitable for use in the process of the disclosure include Pd(0) or Pd(II) catalysts such as dichlorobis(tri-o-tolylphosphine)palladium(II), tetrakis(triphenylphosphine)palladium(0), or the like. Hydrolysis of amide 9 with potassium carbonate and methanol produced amine 10, which was converted, as above, to cyclobutane isothiocyanate 11.

Scheme 8:

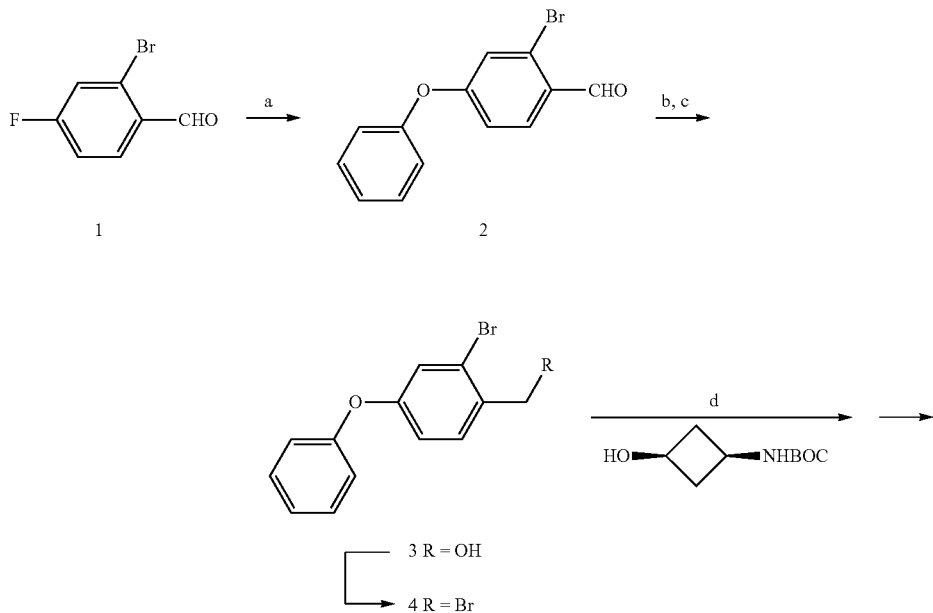

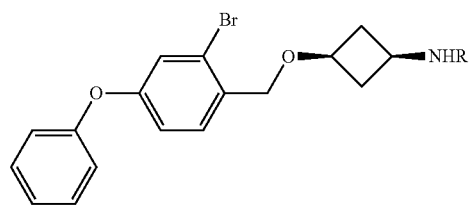
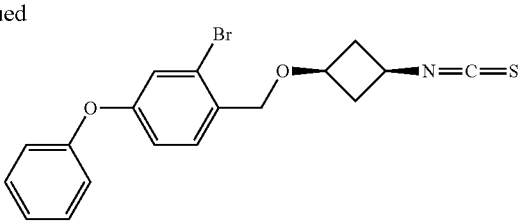

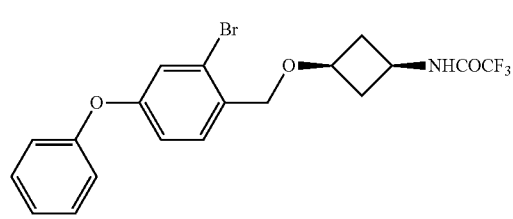
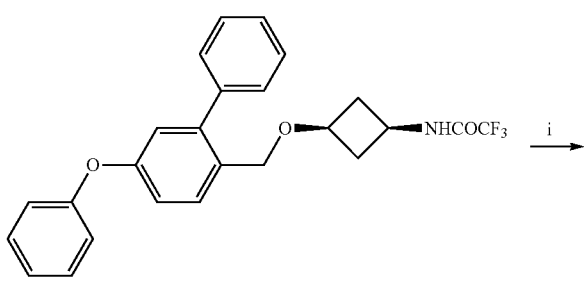

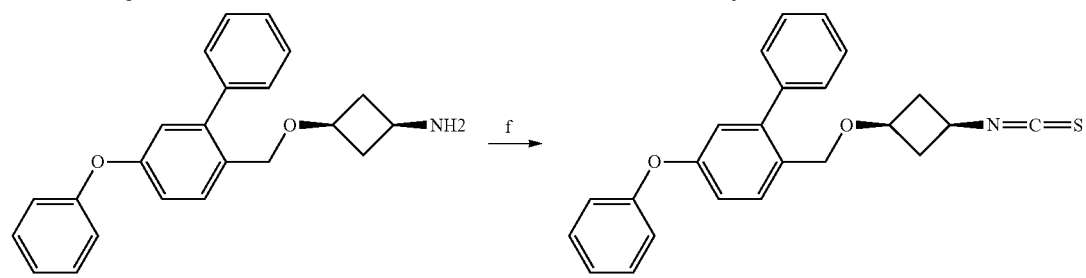

Reagents: (a) phenol, K₂CO₃, DMF; (b) NaBH₄, MeOH; (c) PBr₃, THF; (d) NaH, DMF; (e) TFA, CH₂Cl₂; (f) 1,1′-thiocarbonyldi-2-(1H)-pyridone, Et₃N, CH₂Cl₂; (g) PhB(OH)₂•(PPh₃)₄Pd, K₂CO₃; (h) (CF₃CO)₂O, pyridine; (i) K₂CO₃, MeOH The following examples were prepared according to Method G.

Example 49

2-Bromo-1-(((1S,3S)-3-isothiocyanatocyclobutoxy)methyl)-4-phenoxybenzene. Step 1. 2-Bromo-4-phenoxybenzaldehyde. Potassium carbonate (5.98 g, 43.28 mmol) was added into a mixture of phenol (2.31 g, 24.6 mmol), 2-bromo-4-fluorobanzaldehyde and DMF (50 mL). The mixture was stirred at 100° C. for 18 hours, cooled to room temperature and then poured into water (200 mL). The mixture was stirred for 30 minutes and the precipitated solid filtered and washed with water. 2-Bromo-4-phenoxybenzaldehyde as an off-white sold (6.15 g, 90% yield) was collected and used to the next step. $^1$H NMR (500 MHz, CDCl₃) δ ppm 10.24 (s, 1H), 7.9 (d, J=9.0 Hz, 1H), 7.45-7.42 (m, 2H), 7.27 (t, J=7.5 Hz, 1H), 7.17 (d, J=2.5 Hz, 1H), 7.09-7.08 (m, 2H), 6.98 (dd, J=9.0, 2.5 Hz, 1H).

Step 2. (2-Bromo-4-phenoxyphenyl)methanol. Sodium borohydride (544.3 mg, 14.4 mmol) was added in portions into a cold (0° C.) mixture of 2-bromo-4-phenoxybenzaldehyde (6.25 g, 22.56 mmol) and anhydrous methanol (30 mL). After the addition the mixture stirred for 30 minutes, and then it was carefully poured into ice water. The mixture was extracted with ethyl acetate and the organic extracts washed with water and brine and dried over anhydrous MgSO₄. The solvents were removed under vacuum and the residue was purified on silica gel (Biotage; eluting solvents hexanes: EtOAc 3/1 ratio) to afford (2-bromo-4-phenoxyphenyl)methanol as oil (5.92 g, 94.4% yield): $^1$H NMR (500 MHz, CDCl₃) δ ppm 7.42 (d, J=8.5 Hz, 1H), 7.38-7.34 (m, 4H), 7.2 (d, J=2.5 Hz, 1H), 7.16 (t, J=7.5 Hz, 1H), 7.0 (dd, J=8.5, 2.5 Hz, 1H), 4.71 (d, J=6.5 Hz, 2H), 1.97 (t, J=6.5 Hz, 1H).

Step 3. 2-Bromo-1-(bromomethyl)-4-phenoxybenzene. Phosphorus tribromide (4.3 mL, 44.74 mmol) was added dropwise into a cold (0° C.) mixture of (2-bromo-4-phenoxyphenyl)methanol (4.9 g, 17.56 mmol) and anhydrous tetrahydrofuran (50 mL). After the addition the mixture stirred at room temperature for 5 hours, and then it was carefully poured into ice water. The mixture was extracted with ethyl acetate and the organic extracts washed with saturated aqueous sodium bicarbonate (three times), water and brine and dried over anhydrous MsSO₄. The solvents were removed under vacuum and the residue was purified on silica gel (Biotage; eluting solvents hexanes: EtOAc 30/1 ratio) to afford 2-bromo-1-(bromomethyl)-4-phenoxybenzene as oil (4.26 g, 71% yield): $^1$H NMR (500 MHz, CDCl$_3$) δ ppm 7.4-7.36 (m, 3H), 7.19-7.16 (m, 2H), 7.04-7.03 (m, 2H), 6.92 (dd, J=8., 2.5 Hz, 1H), 4.6 (s, 2H).

Step 4. tert-Butyl ((1S,3S)-3-((2-bromo-4-phenoxybenzyl)oxy)cyclobutyl)carbamate. Sodium hydride (60% dispersion in mineral oil; 235 mg, 5.88 mmol) was added into a cold (0° C.) mixture of tert-butyl ((1S,3S)-3-hydroxycyclobutyl)carbamate (1.1 mg, 5.86 mmol) and anhydrous THF (10 mL). After stirring for 1 hour, 2-bromo-1-(bromomethyl)-4-phenoxybenzene (2.01 g, 5.88 mmol) was added and the mixture was allowed to come to room temperature and stirred for 8 hours. Then, the mixture was poured into saturated aqueous ammonium chloride and extracted with ethyl acetate (2×). The organic extracts were dried over anhydrous MgSO$_4$. The solvents were removed under vacuum and the residue was purified on silica gel (Biotage; eluting solvents hexanes: EtOAc 6/1 ratio) to afford tert-butyl ((1S,3S)-3-((2-bromo-4-phenoxybenzyl)oxy)cyclobutyl)carbamate as oil (2.16 g, 82% yield). $^1$H NMR (500 MHz, CDCl$_3$) δ ppm 7.38-7.34 (m, 3H), 7.18 (d, J=2.5 Hz, 1H), 7.15 (dt, J=7.5 Hz, 1.5 Hz, 1H), 7.09-7.0 (m, 2H), 6.96 (dd, J=9.0, 2.5 Hz 1H,), 4.63 (brs, 1H), 4.43 (s, 2H), 3.83-3.77 (m, 2H), 2.76-2.74 (m, 2H), 1.87-1.81 (m, 2H), 1.43 (s, 9H).

Step 5. (1S,3S)-3((2-Bromo-4-phenoxybenzyl)oxy)cyclobutan-1-amine. TFA. Trifluoroacetic acid (0.49 mL, 6.44 mmol) was added into a mixture of tert-butyl ((1S,3S)-3-((2-bromo-4-phenoxybenzyl)oxy)cyclobutyl)carbamate (288.6 mg, 0.64 mmol) and CH$_2$Cl$_2$ (10 mL). The mixture was stirred at room temperature for 5 h and then the volatiles were removed under vacuum. The residue was taken (3×) successively in CHCl$_3$ (10 mL) and the volatiles were removed under vacuum to ensure removal of excess TFA. The crude (1S,3S)-3-((2-bromo-4-phenoxybenzyl)oxy)cyclobutan-1-amine. TFA (297 mg) was carried to the next step. Step 5. 2-Bromo-1-(((1S,3S)-3-isothiocyanatocyclobutoxy)methyl)-4-phenoxybenzene. Trimethylamine (0.27 mL, 1.93 mmol) was added into a mixture of (1S,3S)-3-((2-bromo-4-phenoxybenzyl)oxy)cyclobutan-1-amine. TFA (297 mg, 0.64 mmol), and CH$_2$Cl$_2$ (8 mL). After stirring for 10 minutes 1,1'-thiocarbonyldi-2(1H)-pyridone (374 mg, 1.61 mmol) was added and the mixture was stirred at temperature for 2 h. The mixture was diluted in EtOAc (30 mL) and washed with water and brine. The organics extracts were dried over anhydrous MgSO$_4$. The solvents were removed under vacuum and the residue was purified on silica gel (Biotage; eluting solvents hexanes: EtOAc 10/1 ratio) to afford 2-bromo-1-(((1S,3S)-3-isothiocyanatocyclobutoxy) methyl)-4-phenoxybenzene as oil (169 mg, 67.3% yield). $^1$H NMR (500 MHz, CDCl$_3$) δ ppm 7.38-7.34 (m, 3H), 7.19 (t, J=2.5 Hz, 1H), 7.15 (t, J=7.5 Hz, 1H), 7.03-7.0 (m, 2H), 6.97 (dd, 8.0, 2.5 Hz, 1H), 4.45 (s, 2H), 3.84-3.89 (m, 1H), 3.74-3.71 (m, 1H), 2.85-2.8 (m, 2H), 2.35-2.29 (m, 2H).

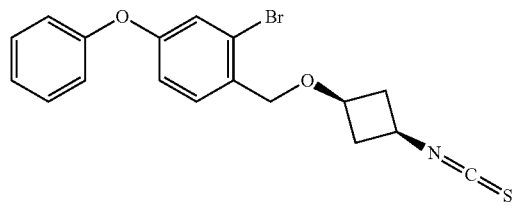 [SMILES: S=C=N[C@H]1C[C@@H](OCc2ccc(Oc3ccccc3)cc2Br)C1]

Example 50

Step 1. N-((1S,3S)-3-((2-Bromo-4-phenoxybenzyl)oxy)cyclobutyl)-2,2,2-trifluoroacetamide. Trifluoroacetic anhydride (0.15 mL, 1.08 mmol) was added into a cold (0° C.) mixture of (1S,3S)-3-((2-bromo-4-phenoxybenzyl)oxy)cyclobutan-1-amine. TFA (332.6 mg, 0.72 mmol), pyridine (0.17, 2.16 mmol), and CH$_2$Cl$_2$ (4 mL). After stirring for 2 hours, the mixture was diluted in ethyl ether (30 mL) and washed with water and brine. The organics extracts were dried over anhydrous MgSO$_4$. The solvents were removed under vacuum and the residue was purified on silica gel (Biotage; eluting solvents hexanes: EtOAc 4/1 ratio) to afford N-((1S,3S)-3-((2-bromo-4-phenoxybenzyl)oxy)cyclobutyl)-2,2,2-trifluoroacetamide as oil (262 mg, 82.1% yield). $^1$H NMR (500 MHz, CDCl$_3$) δ ppm 7.38-7.35 (m, 3H), 7.2 (t, J=2.5 Hz, 1H), 7.15 (t, J=7.5 Hz, 1H), 7.03-7.0 (m, 2H), 6.97 (dd, 8.0, 2.5 Hz, 1H), 6.42 (brs, 1H), 4.48 (s, 2H), 4.11-4.0 (m, 1H), 3.92-3.9 (m, 1H), 2.88-24.8 (m, 2H), 2.02-1.99 (m, 2H).

Step 2. 2,2,2-Trifluoro-N-((1S,3S)-3-((5-phenoxy-[1,1'-biphenyl]-2-yl)methoxy)cyclobutyl) acetamide. Into a microwave vessel were added N-((1s,3s)-3-((2-bromo-4-phenoxybenzyl)oxy)cyclobutyl)-2,2,2-trifluoroacetamide (262 mg, 0.59 mmol), phenylboronic acid (144 mg, 1.18 mmol), cesium fluoride (269 mg, 1.77 mmol) and anhydrous dimethoxyethane (8 mL). Dry argon gas was passed through the mixture for 10 minutes and then tetrakis(triphenylphosphine)palladium(0) (6.8 mg 0.0059 mmol) was added and the argon flow continued for 5 additional minutes. Then, the vessel was sealed and microwaved at 100° C. for 1 h. The mixture was diluted with EtOAc (30 mL) and washed with water and brine. The organics extracts were dried over anhydrous MgSO$_4$. The solvents were removed under vacuum and the residue was purified on silica gel (Biotage; eluting solvents hexanes: EtOAc 4/1 ratio) to afford 3-((5-phenoxy-[1,1'-biphenyl]-2-yl)methoxy)azetidine-1-carbonitrile as oil (185 mg, 79% yield): $^1$H NMR (500 MHz, CDCl$_3$) δ ppm 7.44-7.39 (m, 4H), 7.38-7.31 (m, 4H), 7.14 (dt, J=7.5 Hz, 1.5 Hz, 1H), 7.07-7.05 (m, 2H), 7.01 (dd, J=8.0, 2.5 Hz, 1H), 6.94 (d, J=2.5 Hz, 1H), 4.26 (s, 2H), 4.25-4.2 (m, 1H), 4.14-4.11 (m, 2H), 3.94-3.91 (m, 2H).

Step 3. (1S,3S)-3-((5-Phenoxy-[1,1'-biphenyl]-2-yl)methoxy)cyclobutan-1-amine. Potassium carbonate (125 mg, 0.91 mmol) was added into a mixture of 3-((5-phenoxy-[1,1'-biphenyl]-2-yl)methoxy)azetidine-1-carbonitrile (160 mg, 0.36 mmol), MeOH (4 mL)) and water (8 mL). After stirring for 2 hours the mixture poured in to water (20 mL) and extracted with dichloromethane (3×). The organics extracts were dried over anhydrous MgSO$_4$. The solvents were removed under vacuum to afford (1S,3S)-3-((5-phenoxy-[1,1'-biphenyl]-2-yl)methoxy)cyclobutan-1-amine (117 mg) was carried to the next step.

Step 4. 2-(((1S,3S)-3-Isothiocyanatocyclobutoxy) methyl)-5-phenoxy-1,1'-biphenyl. Trimethylamine (0.16 mL, 1.14 mmol) was added into a mixture of (1S,3S)-3-((5-phenoxy-[1,1'-biphenyl]-2-yl)methoxy)cyclobutan-1-amine (124 mg, 0.36 mmol), and CH$_2$Cl$_2$ (6 mL). After stirring for 10 minutes 1,1'-thiocarbonyldi-2(1H)-pyridone (240.8 mg, 1.08 mmol) was added and the mixture was stirred at temperature for 2 h. The mixture was diluted in EtOAc (20 mL) and washed with water and brine. The organics extracts were dried over anhydrous MgSO$_4$. The solvents were removed under vacuum and the residue was purified on silica gel (Biotage; eluting solvents hexanes: EtOAc 10/1 ratio) to afford 2-(((1S,3S)-3-isothiocyanatocyclobutoxy) methyl)-5-phenoxy-1,1'-biphenyl as oil (97.5 mg, 70% yield). ¹H NMR (500 MHz, CDCl₃) δ ppm 7.44-7.37 (m, 4H), 7.35-7.32 (m, 4H), 7.12 (dt, J=7.5, 1.5 Hz, 1H), 7.06-7.04 (m, 2H), 7.0 (dd, J=8.0, 2.5 Hz, 1H), 6.94 (d, 2.5 Hz, 1H), 4.23 (s, 2H), 3.67-3.62 (m, 2H), 2.7-2.65 (m, 2H), 2.16-2.1 (m, 2H).

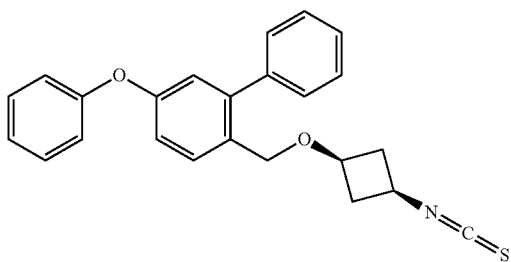 [SMILES: S=C=N[C@H]1C[C@@H](OCc2ccc(Oc3ccccc3)cc2-c2ccccc2)C1]

The preparation of the analogs 5 and 6 (Scheme 9) were prepared according to Method F with a modification in coupling alcohol 2 with an appropriate substituted phenol using the Mitsunobu protocol.

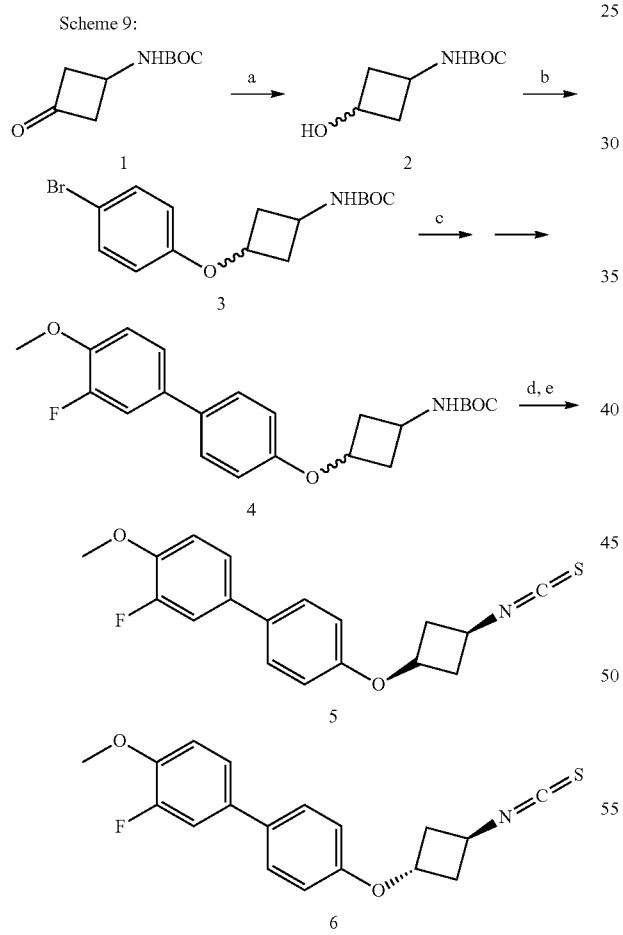

tert-Butyl (3-(4-bromophenoxy)cyclobutyl)carbamate. Diisopropyl azodicarboxylate (0.76 mL, 3.88 mmol) was added into a mixture of tert-butyl (3-hydroxycyclobutyl) carbamate (485 mg, 2.59 mmol), 4-bromophenol (538 mg, 3.11 mmol) and THF (25 mL). The mixture was stirred at 50° C. for 8 hours and then poured into water and extracted with EtOAc. The organics extracts were washed with brine and dried over anhydrous MgSO₄. The solvents were removed under vacuum and the residue was purified on silica gel (Biotage; eluting solvents hexanes: EtOAc 4/1 ratio) to afford tert-butyl (3-(4-bromophenoxy)cyclobutyl) carbamate 1 as oil (487 mg, 55% yield). ¹H NMR (500 MHz, CDCl₃) δ ppm 7.33 (d, J=8.0 Hz, 1H), 7.31 (d, J=8.0 Hz, 1H), 6.74 (d, J=8.0 Hz, 1H), 6.64 (d, J=8.0 Hz, 1H), 4.79 (brs, 1H), 4.74-4.71 (m, 2H), 4.31-4.29 (m, 1H), 2.56-2.51 (m, 2H), 2.37-2.36 (m, 2), 1.45 (s, 9H).

Example 51

3-Fluoro-4'-((1R,3R)-3-isothiocyanatocyclobutoxy)-4-methoxy-1,1'-biphenyl: ¹H NMR (500 MHz, CDCl₃) δ ppm 7.54 (d, J=9.0 Hz, 1H), 7.28-7.23 (m, 2H), 7.0 (t, J=9.0 Hz, 1H), 6.82 (d, J=9.0 Hz, 1H), 4.97-4.93 (m, 1H), 4.43-4.39 (m, 1H), 2.77-2.72 (m, 2H), 2.70-2.64 (m, 2H).

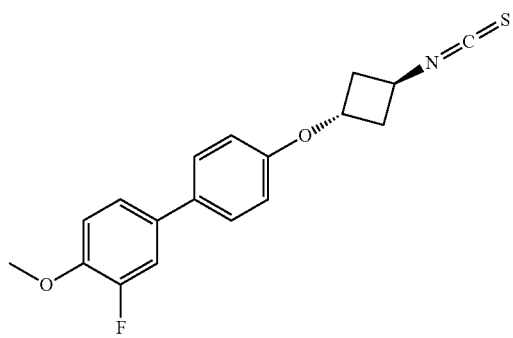 [SMILES: COc1ccc(-c2ccc(O[C@H]3C[C@H](N=C=S)C3)cc2)cc1F]

Example 52

3-Fluoro-4'-((1S,3S)-3-isothiocyanatocyclobutoxy)-4-methoxy-1,1'-biphenyl: ¹H NMR (500 MHz, CDCl₃) δ ppm 7.54 (d, J=8.5 Hz, 1H), 7.28-7.23 (m, 2H), 7.0 (t, J=8.5 Hz, 1H), 6.84 (d, J=8.5 Hz, 1H), 4.45-4.40 (m, 1H), 3.94-3.86 (m, 1H), 3.05-3.03 (m, 2H), 2.53-2.47 (m, 2H).

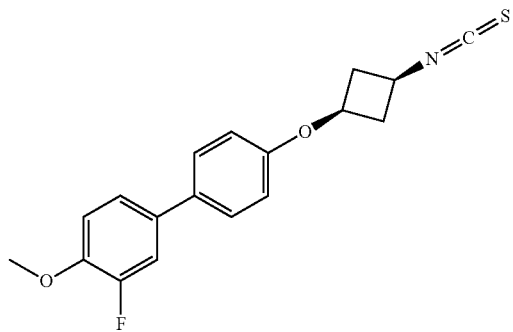 [SMILES: COc1ccc(-c2ccc(O[C@H]3C[C@@H](N=C=S)C3)cc2)cc1F]

Method H.

N-linked cyanamides 5 and 6 were prepared according to Scheme 10. Reductive amination of 3-oxoazetidine 1 with amines 2 using sodiumtriacetoxy borohydride under acidic conditions (i.e. AcOH) produced amines 3. Applications of the processes of Method F, steps 7-8 afforded N-linked cyanamides 5 and 6.

Scheme 10:

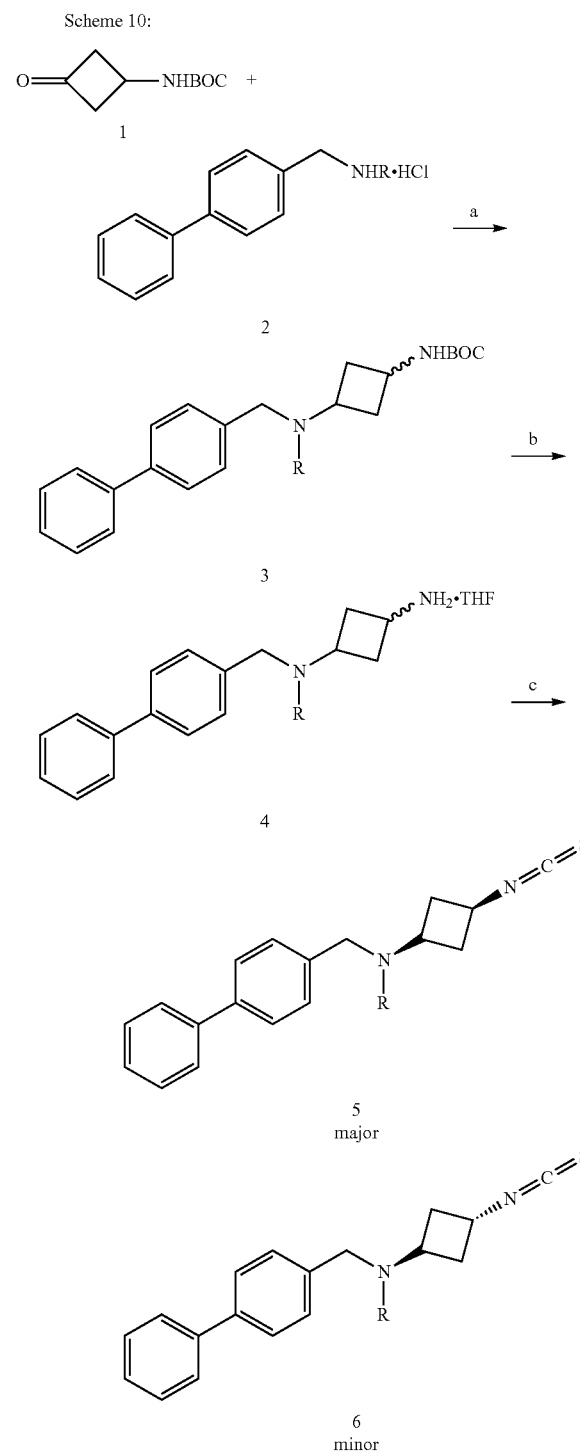

Reagents: (a) Na(OAC)₃BH, AcOH, THF; (b) TFA, CH₂Cl₂; (d) 1,1'-thiocarbonyldipyridin-2(1H)-one, Et₃N, CH₂Cl₂ tert-Butyl (3-(([1,1'-biphenyl]-4-ylmethyl)(methyl) amino)cyclobutyl)carbamate. To a mixture of 1-([1,1'-biphenyl]-4-yl)-N-methylmethanamine hydrochloride (254 mg, 1.09 mmol), tert-butyl (3-oxocyclobutyl)carbamate (183 mg, 0.99 mmol), acetic acid (0.17 mL) and anhydrous tetrahydrofuran (3 mL), was added sodiumtriacetoxy borohydride (292 mg, 1.39 mmol). The mixture was stirred for 5 hours and then was quenched with saturated aqueous sodium bicarbonate. The mixture was extracted with ethyl acetate, washed with brine and dried over anhydrous MgSO4. The solvents were removed under vacuum and the residue was purified on silica gel (Biotage; eluting solvents hexanes: EtOAc 2/1 ratio) to afford tert-butyl (3-(([1,1'-biphenyl]-4-ylmethyl)(methyl)amino)cyclobutyl)carbamate as oil (351 mg, 96.9% yield): ¹H NMR (500 MHz, CDCl₃) δ ppm 7.6 (d, J=5.5 Hz, 2H), 7.5 (d, J=8.0 Hz, 2H), 7.4 (t, J=7.5 Hz, 2H), 7.35 (m, 3H), [4.82 (m), 4.62 (m), 1H], [4.13 (m), 3.86 (m), 1H], 3.4 (s, 2H), [3.08-3.05 (m), 2.57-2.54 (m), 2H], [2.05 (s), 2.04 (m), 3H], [2.39 (m), 1.73-1.71 (m), 2H], [1.45 (s), 1.44 (s), 9H].

The following examples were prepared according to Method H.

Example 53

(1R,3R)—N-([1,1'-Biphenyl]-4-ylmethyl)-3-isothiocyanato-N-methylcyclobutan-1-amine: ¹H NMR (500 MHz, CDCl₃) δ ppm 7.61-7.58 (m, 2H), 7.56 (d, J=8.0, 2H), 7.43 (t, J=7.5 Hz, 2H), 7.36-7.32 (m, 3H), 3.83-3.78 (m, 1H), 3.40 (s, 2H), 2.64-2.59 (m, 3H), 2.24-2.18 (m, 2H), 2.06 (s, 3H).

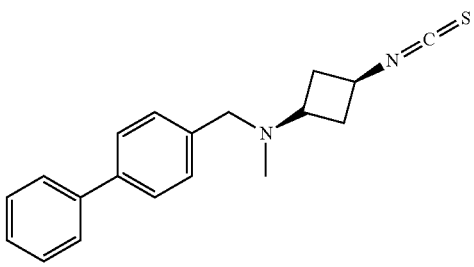

Example 54

(1S,3S)—N-([1,1'-biphenyl]-4-ylmethyl)-3-isothiocyanato-N-methylcyclobutan-1-amine: ¹H NMR (500 MHz, CDCl₃) δ ppm 7.6-7.58 (m, 2H), 7.56 (d, J=8.0, 2H), 7.45 (t, J=7.5 Hz, 2H), 7.36-7.32 (m, 3H), 4.2 (m, 1H), 3.41 (s, 2H), 3.27 (m, 1H), 2.41-2.38 (m, 4H), 2.06 (s, 3H).

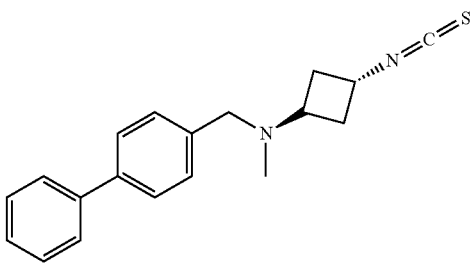

Example 55

(1R,3R)—N-(4-(benzo[d][1,3]dioxol-5-yl)benzyl)-3-isothiocyanato-N-methylcyclobutan-1-amine: ¹H NMR (500 MHz, CDCl₃) δ ppm 7.46 (d, J=8.0, 2H), 7.33 (d, J=8.0, 2H), 7.07 (m, 2H), 6.88 (d, J=7.5 Hz, 1H), 6.0 (s, 2H), 3.83-3.75 (m, 1H), 3.39 (s, 2H), 2.64-2.59 (m, 3H), 2.24-2.18 (m, 2H), 2.05 (s, 3H).

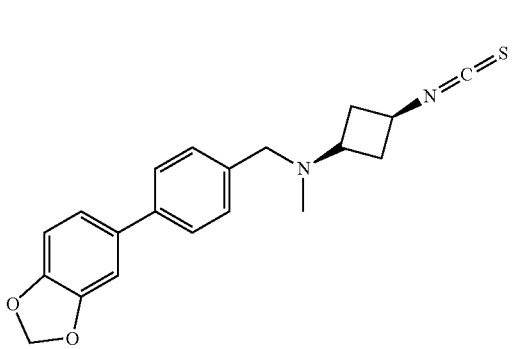

Example 56

(1R,3R)—N-(4-(benzo[d][1,3]dioxol-5-yl)benzyl)-N-ethyl-3-isothiocyanatocyclobutan-1-amine: $^1$H NMR (500 MHz, CDCl$_3$) δ ppm 7.46 (d, J=8.0, 2H), 7.33 (d, J=8.0, 2H), 7.07 (m, 2H), 6.88 (d, J=7.5 Hz, 1H), 6.0 (s, 2H), 3.79-3.72 (m, 1H), 3.54 (s, 2H), 2.89-2.82 (m, 1H), 2.60-2.55 (m, 2H), 2.49-2.45 (m, 2H), 2.19-2.13 (m, 2H), 1.0 (t, J=7 Hz, 3H).

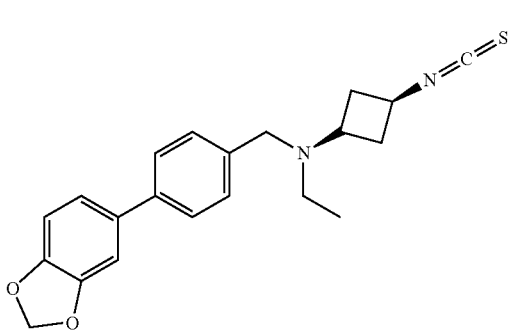

Method I.

The cyclobutane-isothiocyanate 6 (Scheme 11) was prepared according to Method I. Methylenecyclobutane-1-carbonitrile 1 was oxidized with NaIO$_4$/RuCl$_3$ to afford cyclobutanone 2, which upon reduction with NaBH$_4$ and alkylation with aryl-alkyl halides afforded carbonitrile 4. Nitrile 4 was reduced with LiAlH$_4$ to afford amine 5, which was comverted to isothiocyanate 6 according to Method F, step 8.

Scheme 11:

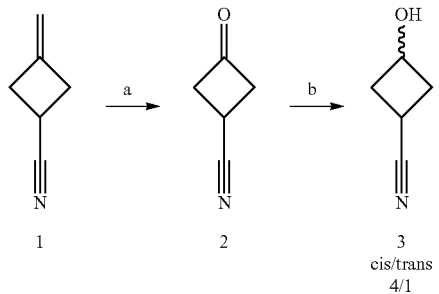

Reagents: (a) RuCl$_3$, NaIO$_4$; (b) NaBH$_4$, MeOH; (c) 4-Ph-benzyl chloride, NaH, DMF, (d) LiAlH$_4$, AlCl$_3$, Et$_2$O; (e) 1,1'-thiocarbonyldi-2(1H)-pyridone, Et$_3$N, CH$_2$Cl$_2$ Step 1. ((1S,3S)-3-([1,1'-Biphenyl]-4-ylmethoxy)cyclobutyl)methanamine. To a cold (0° C.) mixture of (1S,3S)-3-([1,1'-biphenyl]-4-ylmethoxy)cyclobutane-1-carbonitrile (120 mg, 0.45 mmol) and anhydrous Et$_2$O (2 mL) were added AlCl$_3$ (77 mg, 0.58 mmol) and LiALH$_4$ (17.1 mg, 0.45 mmol). The mixture was allowed to come to room temperature and stirred for 2 hours. Then, the mixture cooled to 0° C. and were carefully quenched with water. The mixture was basified with NaOH (4N) and extracted (3×) with CH$_2$Cl$_2$. The solvents were removed under vacuum to afford ((1S,3S)-3-([1,1'-biphenyl]-4-ylmethoxy)cyclobutyl) methanamine as oil (120 mg), which was used to the next step. ((1S,3S)-3-([1,1'-Biphenyl]-4-ylmethoxy)cyclobutyl) methanamine was converted to 4-(((1S,3S)-3-(isothiocyanatomethyl)cyclobutoxy)methyl)-1,1'-biphenyl following Method F, step 8.

The following example was prepared according to Method I.

Example 57

4-(((1S,3S)-3-(isothiocyanatomethyl)cyclobutoxy)methyl)-1,1'-biphenyl. $^1$H NMR (500 MHz, CDCl$_3$) δ ppm 7.57-7.53 (m 4H), 7.43-7.37 (m, 4H), 7.35-7.31 (m, 1H), 4.42 (s, 2H), 3.99-3.92 (m, 1H), 3.54-3.51 (m, 2H), 2.48-2.41 (m, 2H), 2.25-2.16 (m, 1H), 1.82-1.74 (m, 2H).

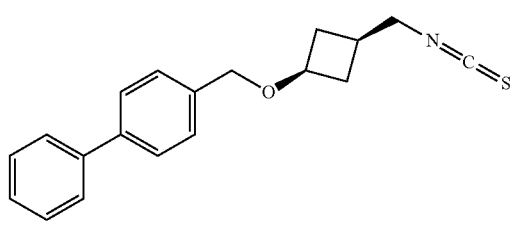 [SMILES: S=C=NC[C@H]1C[C@@H](OCc2ccc(-c3ccccc3)cc2)C1]

Method J.

The cyclohexyl-isothiocyanate 5 (Scheme 12) was prepared according to Method J. Alcohol 1 was alkylated with 4-bromobenzyl bromide in the presence of a base such as sodium hydride in an aprotic polar solvent as tetrahydrofuran to afford ether 3. Palladium mediated cross-coupling reaction between 2 and the appropriate boronic acid was used to generate biphenyl analog 3. Palladium catalysts suitable for use in the process of the disclosure include Pd(0) or Pd(II) catalysts such as dichlorobis(tri-o-tolylphosphine)palladium(II), tetrakis(triphenylphosphine)palladium(0), or the like. Unmasking of the amino group of 3 to generate amine 4 was achieved upon treatment with a strong organic acid as trifluoroacetic acid in a chlorinated solvent such as dichloromethane. Cyclohexyl isothiocyanate 5 was prepared from 4 upon treatment with 1,1'-thiocarbonyldi-2(1H)-pyridone and an organic base such as triethylamine in an inert solvent as dichloromethane.

Scheme 12:

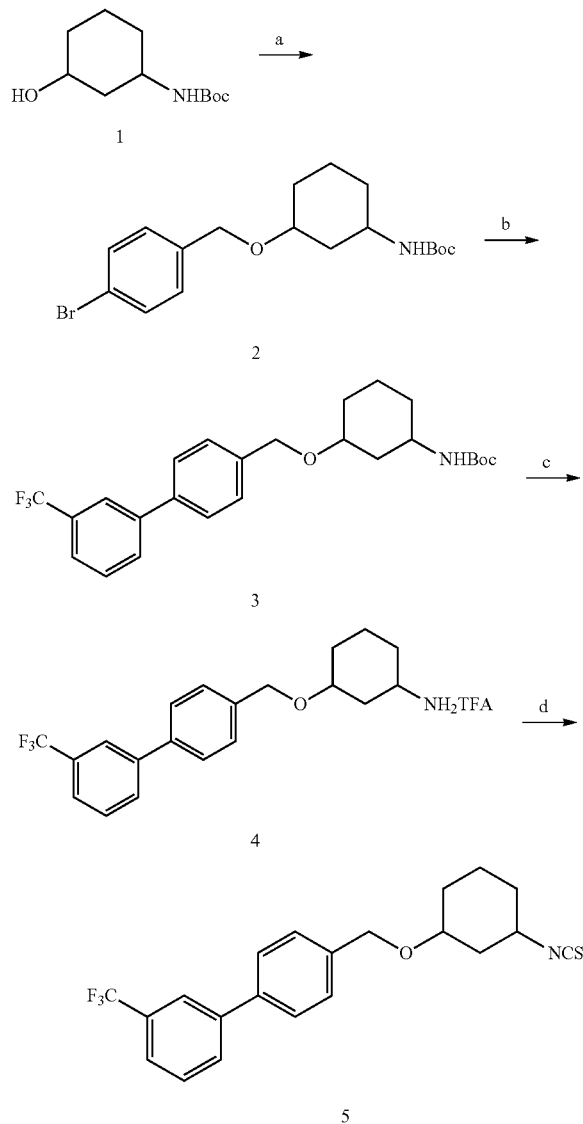

Reagents: (a) NaH, THF, 4-bromobenzylbromide (b) Pd(PPh$_3$)$_4$, aryl boronic acid, K$_2$CO$_3$, dioxane:H$_2$O (c) TFA, DCM (d) thiodicarbonylpyridone, CH$_2$Cl$_2$ The following Examples were prepared according to Method J.

Example 58

4'-(((3-Isothiocyanatocyclohexyl)oxy)methyl)-3-(trifluoromethyl)-1,1'-biphenyl. Step 1. tert-Butyl (3-((4-bromobenzyl)oxy)cyclohexyl)carbamate. To a stirring solution of tert-butyl (3-hydroxycyclohexyl)carbamate (220 mg, 1.02 mmol) in THF (3 mL) at 0° C. was added NaH (41 mg, 1.02 mmol) and stirred at 0° C. for 30 mins, then 4-bromobenzyl bromide (255 mg, 1.02 mmol) was added and the reaction mixture was warmed to rt and stirred for 3 h. The reaction mixture was cooled to 0° C., and quenched by the dropwise addition of sat. ammonium chloride, extracted with EtOAc (3×50 mL). The combined organic layers were washed with brine, dried over sodium sulfate, filtered and concentrated under reduced pressure. The crude residue was purified by silica gel chromatography using 10-25% EtOAc/Hexanes gradient elution to afford tert-butyl (3-((4-bromobenzyl)oxy)cyclohexyl)carbamate as a white solid (184 mg, 48%): $^1$H NMR (500 MHz, CDCl$_3$) δ ppm 7.45 (d, J=8.3 Hz, 2H), 7.21 (d, J=2H), 4.92 (bs, 1H), 4.48 (s, 2H), 3.55 (m, 1H), 3.45 (bs, 1H), 2.19 (d, 11.72 Hz, 1H), 1.70-1.95 (m, 3H)1.44 (s, 9H), 1.15-1.37 (m, 4H).

Step 2. tert-butyl (3((3'-(trifluoromethyl)-[1,1'-biphenyl]-4-yl)methoxy)cyclohexyl) carbamate. A stirring solution of tert-butyl (3-((4-bromobenzyl)oxy)cyclohexyl)carbamate (92 mg, 0.24 mmol), 3-trifluoromethylphenyl boronic acid (68 mg, 0.36 mmol), potassium carbonate (99 mg, 0.72 mmol) in 10:1 dioxane:water (11 mL) was purged for 10 mins with argon, then Pd(PPh$_3$)$_4$ (10 mg, 0.012 mmol) was added and the mixture heated to 80° C. for 12 h under an atmosphere of argon. The reaction mixture was cooled to rt, quenched with sat. sodium bicarbonate (50 mL) and extracted with EtOAc (3×50 mL). The combined organic layers were washed with brine, dried over sodium sulfate, filtered and concentrated under reduced pressure to afford a crude residue which was further purified by silica gel chromatography eluting with 10-50% EtOAc/Hexanes gradient to afford tert-butyl (3-((3'-(trifluoromethyl)-[1,1'-biphenyl]-4-yl)methoxy)cyclohexyl)carbamate as a white solid: $^1$H NMR (500 MHz, CDCl$_3$) δ ppm 7.82 (s, 1H), 7.75 (d, J=7.3 Hz, 1H), 7.52-7.62 (m, 4H), 7.44 (d, J=7.8 Hz, 2H), 4.59 (s, 2H), 3.46-3.65 (m, 2H), 2.25 (d, J=9.8 Hz, 1H), 1.75-1.98 (m, 3H), 1.45 (s, 9H), 1.18-1.40 (m, 4H).

Step 3. 3-((3'-(trifluoromethyl)-[1,1'-biphenyl]-4-yl) methoxy)cyclohexan-1-amine. To a solution of (3-((3'-(trifluoromethyl)-[1,1'-biphenyl]-4-yl)methoxy)cyclohexyl)carbamate (47 mg, 0.105 mmol) in DCM (1.0 mL) was added TFA (0.1 mL, 1.3 mmol) and the mixture was stirred at rt for 4 h. The reaction mixture was quenched with sat. sodium bicarbonate, extracted with DCM (2×25 mL). The combined organic phases were washed with brine, dried of sodium sulfate, filtered and concentrated to afford 3-((3'-(trifluoromethyl)-[1,1'-biphenyl]-4-yl)methoxy)cyclohexan-1-amine (36 mg, 99%): $^1$H NMR (500 MHz, CDCl$_3$) δ ppm 7.82 (s, 1H), 7.75 (d, J=7.3 Hz, 1H), 7.59 (d, J=7.8 Hz, 1H), 7.57 (d, J=8.3 Hz, 2H), 7.53 (d, J=7.8 Hz, 1H), 7.45 (d, J=8.3 Hz, 2H), 4.62 (s, 2H), 3.39 (ddd, J=3.91, 10.25, 14.16 Hz, 1H), 2.69 (bs, 1H), 2.28 (d, J=11.7 Hz, 1H), 2.06 (d, J=7.8 Hz, 1H), 1.80 (d, J=10.7 Hz, 2H), 1.48-1.62 (m, 2H), 1.12-1.27 (m, 4H).

Step 4. 4'-(((3-isothiocyanatocyclohexyl)oxy)methyl)-3-(trifluoromethyl)-1,1'-biphenyl. To a stirring solution of 3-((3'-(trifluoromethyl)-[1,1'-biphenyl]-4-yl)methoxy)cyclohexan-1-amine (36 mg, 0.10 mmol) in DCM (5 mL) at 0° C. was added 1,1-thiodicarbonylpyridin-2(1H)-one (76 mg, 0.33 mmol) and the mixture was allowed to warm to rt and stirred for 3 h. The crude reaction mixture was concentrated and purified by silica gel chromatography to afford 4'-(((3-isothiocyanatocyclohexyl)oxy)methyl)-3-(trifluoromethyl)-1,1'-biphenyl as a white solid: ¹H NMR (500 MHz, CDCl₃) δ ppm 7.82 (s, 1H), 7.76 (d, J=7.8 Hz, 1H), 7.60 (d, 9.3 Hz, 2H), 7.56 (d, J=9.3 Hz, 2H), 7.44 (d, J=8.3 Hz, 2H), 4.61 (s, 2H), 3.59 (app tt, J=3.9, 11.2 Hz 1H), 3.39 (app tt, J=4, 10.4 Hz, 1H), 2.51 (ddt, J=12.2, 3.9, 2 Hz, 1H), 2.05 (m, 1H), 1.2-1.92 (m, 6H).

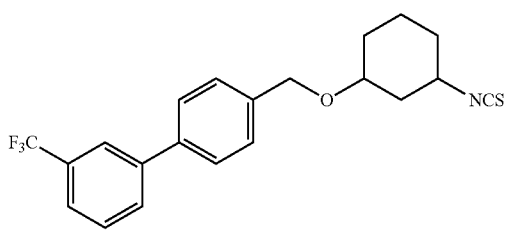

Example 59

3-Fluoro-4'-((((1r,4r)-4-isothiocyanatocyclohexyl)oxy)methyl)-4-methoxy-1,1'-biphenyl: ¹H NMR (500 MHz, CDCl₃) δ ppm 7.82 (s, 1H), 7.76 (d, J=7.8 Hz, 1H), 7.60 (d, 9.3 Hz, 2H), 7.56 (d, J=9.3 Hz, 2H), 7.44 (d, J=8.3 Hz, 2H), 4.61 (s, 2H), 3.59 (app tt, J=3.9, 11.2 Hz 1H), 3.39 (app tt, J=4, 10.4 Hz, 1H), 2.51 (ddt, J=12.2, 3.9, 2 Hz, 1H), 2.05 (m, 1H), 1.2-1.92 (m, 6H).

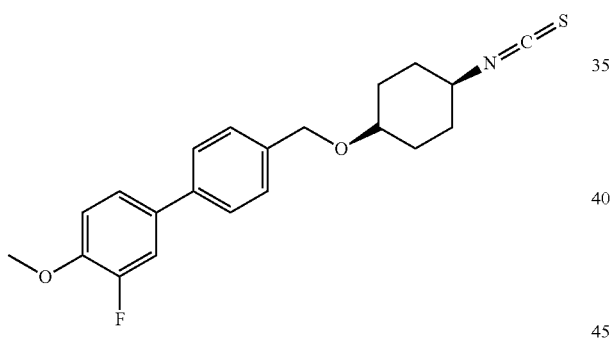

Example 60

1-Bromo-4-((((1R,3R)-3-isothiocyanatocyclopentyl)oxy)methyl)benzene: ¹H NMR (500 MHz, CDCl₃) δ ppm 7.38 (d, J=8.8 Hz, 2H), 7.1 (d, J=8.1 Hz, 2H), 4.33 (d, J=11.7 Hz, 1H), 4.29 (d, J=13.2 Hz, 1H), 4.15 (quin, J=6.6 Hz, 1H), 4.04-4.10 (m, 1H), 1.70-2.15 (m, 6H).

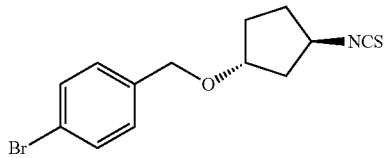

Method K.

Indene-isothiocyanate 6 (Scheme 13) was prepared according to Method K. Indene-amine 1 was protected with di-tert-butyl dicarbonate and triethyl amine as the base to afford 2. Alcohol 2 was alkylated with 4-bromobenzyl bromide in the presence of a base such as sodium hydride in an aprotic polar solvent as tetrahydrofuran to afford ether 3. Palladium mediated cross-coupling reaction between 3 and the appropriate boronic acid was used to generate biphenyl analog 4. Palladium catalysts suitable for use in the process of the disclosure include Pd(0) or Pd(II) catalysts such as dichlorobis(tri-o-tolylphosphine)palladium(II), tetrakis(triphenylphosphine)palladium(0), or the like. Unmasking of the amino group of 4 to generate amine 5 was achieved upon treatment with a strong organic acid as trifluoroacetic acid in a chlorinated solvent such as dichloromethane. Isothiocyanate 6 was prepared from 5 upon treatment with 1,1'-thiocarbonyldi-2(1H)-pyridone and an organic base such as triethylamine in an inert solvent as dichloromethane.

Scheme 13:

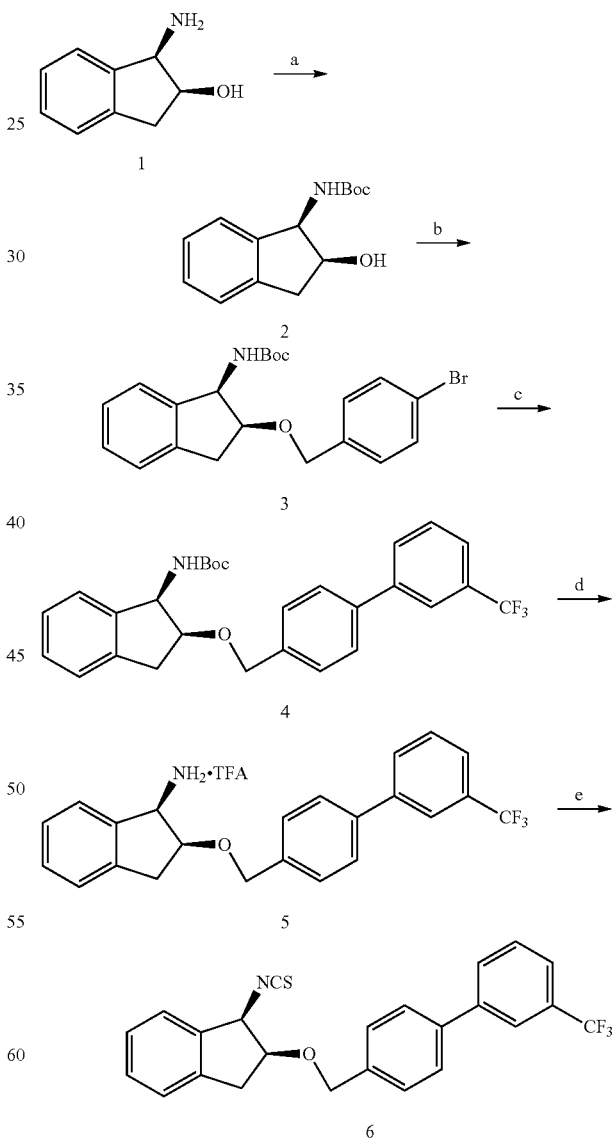

Reagents: (a) di-tert-butyl dicarbonate, DMF, Et₃N; (b) NaH, THF, 4-bromobenzylbromide (c) Pd(PPh₃)₄, aryl boronic acid, K₂CO₃, dioxane:H₂O (d) TFA, DCM (e) thiodicarbonylpyridone, DCM The following examples were prepared according to Method K.

Example 61

(1R,2S)-1-isothiocyanato-2-((3'-(trifluoromethyl)-[1,1'-biphenyl]-4-yl)methoxy)-2,3-dihydro-1H-indene. Step 1. tert-butyl ((1R,2S)-2-hydroxy-2,3-dihydro-1H-inden-1-yl)carbamate. To a stirring suspension of (1R,2S)-(+)-cis-amino-2-indanol (115 mg, 0.77 mmol) and sodium carbonate (183 mg, 1.72 mmol) in THF (2.9 mL) and water (1.3 mL) was added a solution of di-tert-butyl dicarbonate (190 mg, 0.88 mmol) in THF (0.7 mL) and stirred at 0° C. for 1 h, then rt for 2 h. The reaction mixture was diluted with water (50 mL), extracted with EtOAc (3×50 mL), and the combined organic phase was washed with brine and dried over sodium sulfate, filtered and concentrated under reduced pressure. The crude residue was purified by silica gel chromatography using 25% EtOAc/Hexanes eluent to afford tert-butyl ((1R,2S)-2-hydroxy-2,3-dihydro-1H-inden-1-yl)carbamate as a white solid (117 mg, 92%). $^1$H NMR (500 MHz, CDCl$_3$) δ ppm 7.11-7.25 (m, 5H), 5.32-5.44 (m, 1H), 4.85-5.00 (m, 1H), 4.35-4.50 (m, 1H), 3.31 (bs, 1H), 2.99 (dd, J=16.4, 4.6 Hz, 1H), 2.82 (dd, J=10.3, 8.8 Hz, 1H), 1.47 (s, 9H).

Step 2. tert-butyl ((1R,2S)-2-((4-bromobenzyl)oxy)-2,3-dihydro-1H-inden-1-yl)carbamate. To a stirring solution of tert-butyl ((1R,2S)-2-hydroxy-2,3-dihydro-1H-inden-1-yl)carbamate (383 mg, 1.54 mmol), in THF (4.5 mL) at 0° C. was added NaH (60% in mineral oil, 61 mg, 1.54 mmol) and stirred at 0° C. for 30 mins, then 4-bromobenzylbromide (385 mg, 1.54 mmol) was added and the reaction mixture was allowed to warm to rt and stir for 16 h. The reaction was cooled to 0° C. and quenched with slow addition of water (50 mL), and extracted with EtOAc (3×50 mL). The combined organic phase was washed with brine and dried over sodium sulfate, filtered and concentrated to afford a crude residue that was further purified by silica gel chromatography using 10% EtOAc/Hexanes as eluent to afford tert-butyl ((1R,2S)-2-((4-bromobenzyl)oxy)-2,3-dihydro-1H-inden-1-yl)carbamate as a white solid (57 mg, 10%): $^1$H NMR (500 MHz, CDCl$_3$) δ ppm 7.44 (d, J=8.3 Hz, 2H), 7.34 (dd, J=2.9, 4.4 Hz, 1H), 7.19-7.25 (m, 3H), 7.18 (d, J=8.3 Hz, 2H), 5.22 (bs, 2H), 4.56 (d, J=12.2 Hz, 1H), 4.51 (d, J=12.2 Hz, 1H), 4.33 (d, J=2.4 Hz, 1H), 3.05 (dd, J=2.9, 16.6 Hz, 1H), 3.01 (dd, J=4.9, 16.6 Hz, 1H), 1.5 (s, 9H).

Step 3. tert-butyl ((1R,2S)-2-((3'-(trifluoromethyl)-[1,1'-biphenyl]-4-yl)methoxy)-2,3-dihydro-1H-inden-1-yl)carbamate. A stirring solution of tert-butyl ((1R,2S)-2-((4-bromobenzyl)oxy)-2,3-dihydro-1H-inden-1-yl)carbamate (57 mg, 0.136), 3-trifluoromethylphenyl boronic acid (39 mg, 0.20 mmol), potassium carbonate (56 mg, 0.0.41 mmol) in 10:1 dioxane:water (6 mL) was purged for 10 mins with argon, then Pd(PPh$_3$)$_4$ (6 mg, 0.0068 mmol) was added and the mixture heated to 80° C. for 24 h under an atmosphere of argon. The reaction mixture was cooled to rt, quenched with sat. sodium bicarbonate (50 mL) and extracted with EtOAc (3×50 mL). The combined organic layers were washed with brine, dried over sodium sulfate, filtered and concentrated under reduced pressure to afford a crude residue which was further purified by silica gel chromatography eluting with 20% EtOAc/Hexanes gradient to afford tert-butyl ((1R,2S)-2-((3'-(trifluoromethyl)-[1,1'-biphenyl]-4-yl)methoxy)-2,3-dihydro-1H-inden-1-yl)carbamate as a white solid: $^1$H NMR (500 MHz, CDCl$_3$) δ ppm 7.8 (s, 1H), 7.73 (d, J=7.3 Hz, 1H), 7.59 (d, J=7.8 Hz, 1H), 7.55 (d, J=7.8 Hz, 2H), 7.42 (d, J=7.8 Hz, 2H), 7.25-7.36 (m, 3H), 6.95-7.15 (m, 2H).

Step 4. (1R,2S)-2-((3'-(trifluoromethyl)-[1,1'-biphenyl]-4-yl)methoxy)-2,3-dihydro-1H-inden-1-amine TFA Salt. A solution of tert-butyl ((1R,2S)-2-((3'-(trifluoromethyl)-[1,1'-biphenyl]-4-yl)methoxy)-2,3-dihydro-1H-inden-1-yl)carbamate (55 mg, 0.11 mmol) and TFA (0.1 mL) in chloroform (1.1 mL) was stirred at rt for 3 h. The crude reaction mixture was concentrated to afford an oily solid (44 mg, 99%): $^1$H NMR (500 MHz, CDCl$_3$) δ ppm 7.86 (s, 1H), 7.78 (d, J=7.3 1H), 7.56-7.66 (m, 4H), 7.50 (d, J=7.8 Hz, 2H), 7.27 (d, J=6.8 Hz, 2H), 7.12 (d, J=7.8 Hz, 1H), 7.04 (s, 1H), 6.95 (m, 1H), 4.60-4.80 (m, 4H), 3.05-3.22 (m, 2H).

Step 5. (1R,2S)-1-isothiocyanato-2-((3'-(trifluoromethyl)-[1,1'-biphenyl]-4-yl)methoxy)-2,3-dihydro-1H-indene. To a stirring solution of the (1R,2S)-2-((3'-(trifluoromethyl)-[1,1'-biphenyl]-4-yl)methoxy)-2,3-dihydro-1H-inden-1-amine TFA salt (44 mg, 0.089 mmol) in DCM (5 mL) at 0° C. was added NaHCO$_3$ (14 mg, 0.17 mmol), then 1,1-thiodicarbonylpyridin-2(1H)-one (61 mg, 0.26 mmol) and the mixture was stirred at rt for 2 h. The crude reaction mixture was concentrated under reduced pressure, and purified by silica gel chromatography to afford a white solid (31 mg, 66%): $^1$H NMR (500 MHz, CDCl$_3$) δ ppm 7.83 (s, 1H), 7.76 (d, J=7.8 Hz, 1H), 7.61 (d, J=8.3 Hz, 2H), 7.56-7.62 (m, 1H), 7.56 (d, J=7.8 Hz, 2H), 7.39 (d, J=7.3 Hz, 1H), 7.22-7.35 (m, 4H), 5.06 (d, J=5.4 Hz, 1H), 4.81 (d, J=11.7 Hz, 1H), 4.70 (d, J=11.7 Hz, 1H), 4.37 (dd, J=6.4, 11.7 Hz, 1H), 3.10-3.23 (m, 2H).

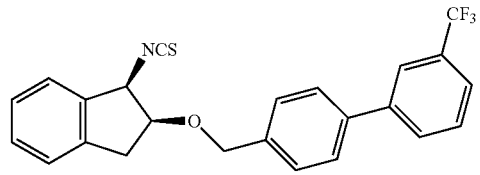

Example 62

(1S,2R)-2-((3'-fluoro-4'-methoxy-[1,1'-biphenyl]-4-yl)methoxy)-1-isothiocyanato-2,3-dihydro-1H-indene: $^1$H NMR (500 MHz, CDCl$_3$) δ ppm 7.55 (d, J=7.8 Hz, 2H), 7.51 (d, J=8.3 Hz, 2H), 7.39 (d, J=7.8 Hz, 1H), 7.24-7.37 (m, 5H), 7.03 (app t, J=8.3 Hz, 1H), 5.05 (d, J=5.4 Hz, 1H), 4.80 (d, J=11.7 Hz, 1H), 4.68 (d, J=11.7 Hz, 1H), 3.93 (s, 3H), 3.17 (app qd, J=15.6, 6.8 Hz, 2H).

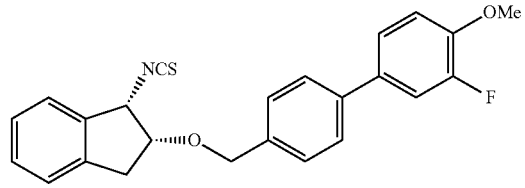

Method L.

Cyanamides 5 (Scheme 14) were prepared as follows. Coupling of hydroxy-azetidine 1 with an aryl bromide (e.g. 1-bromo-4-(bromomethyl)benzene) was accomplished upon treatment with a base such as sodium hydride in an aprotic polar solvent as N,N-dimethylformamide. Palladium mediated cross-coupling reaction between aryl-bromide 2 and the appropriate boronic acid was used to generate the biphenyl-type analogs 3. Palladium catalysts suitable for use in the process of the disclosure include Pd(0) or Pd(II) catalysts such as dichlorobis(tri-o-tolylphosphine)palladium(II), tetrakis(triphenylphosphine)palladium(0), or the like. Inorganic bases suitable for use in the inventive process include Na or K hydroxides, carbonates or bicarbonates, preferably $Na_2CO_3$ or $K_2CO_3$. Solvents suitable for use in the inventive process include polar or non-polar organic solvents such as toluene, dioxane. Unmasking of the azetidine nitrogen 3 was achieved upon treatment with an organic strong acid as trifluoroacetic acid in a chlorinated solvent such as dichloromethane. Generation of cyanamides 5 was accomplished upon treatment with cyanogen bromide and an organic base such as triethylamine in an inert solvent as dichloromethane.

Scheme 14:

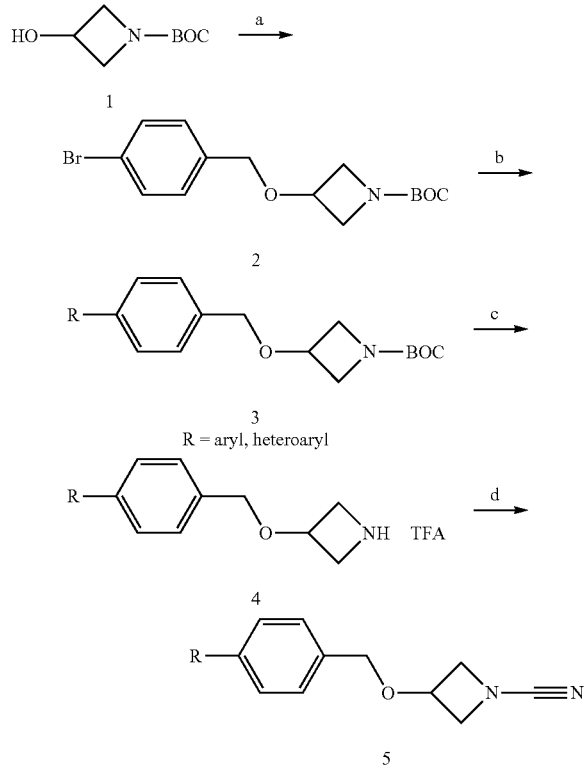

Reagents: (a) 4-bromobenzyl bromide, NaH, DMF; (b) R—B(OH)$_2$, K$_2$CO$_3$, Pd(PPh$_3$)$_4$, dioxane, H$_2$O; (c) trifluoroacetic acid, CH$_2$Cl$_2$; (d) CNBr, Et$_3$N, CH$_2$Cl$_2$.

The following examples were prepared according to Method L.

Example 63

3-((4'-Methoxy-[1,1'-biphenyl]-4-yl)methoxy)azetidine-1-carbonitrile. Step 1. tert-Butyl 3-((4-bromobenzyl)oxy)azetidine-1-carboxylate. Sodium hydride (60% dispersion in mineral oil; 663.2 mg, 16.58 mmol) was added portionwise into a cold (0° C.) solution of tert-butyl 3-hydroxyazetidine-1-carboxylate (2.38 g, 13.82 mmol) and DMF (20 mL). After stirring for 1 hour, 1-bromo-4-(bromomethyl)benzene (3.8 g, 15.2 mmol) was added and the new mixture was allowed to come to room temperature and stirred for 12 hours. The mixture was cooled to 0° C. and MeOH (4 mL) was added dropwise. Then, the mixture was poured into aqueous ammonium chloride and extracted with ethyl ether (2×). The organic extracts were dried over anhydrous MgSO$_4$. The solvents were removed under vacuum and the residue was purified on silica gel (Biogate; eluting solvents hexanes: EtOAc 4/1 ratio) to afford tert-butyl 3-((4-bromobenzyl)oxy)azetidine-1-carboxylate as off-white solid (4.32 g, 92% yield): $^1$H NMR (500 MHz, CDCl$_3$) δ ppm 7.47 (d, J=8 Hz, 2H), 7.20 (d, J=8 Hz, 2H), 4.41. (s, 2H), 4.28 (m, 1H), 4.05 (dd, J=8.5, 5.0 Hz, 2H), 3.85 (dd, J=8.5, 5.0 Hz, 2H), 1.41 (s, 9H).

Step 2. tert-Butyl 3-((4'-methoxy-[1,1'-biphenyl]-4-yl)methoxy)azetidine-1-carboxylate. Into a microwave vessel were added tert-butyl 3-((4-bromobenzyl)oxy)azetidine-1-carboxylate (200 mg, 0.58 mmol), (4-methoxyphenyl)boronic acid (177 mg, 1.16 mmol), K$_2$CO$_3$ (240 mg, 1.74 mmol), dioxane (8 mL) and water (2 mL). Argon gas was passed through the mixture for 10 minutes and then tetrakis(triphenylphosphine)palladium(0) (6.7 mg 0.0058 mmol) and then argon flow continued for 5 additional minutes. Then, the vessel was sealed and microwaved at 100° C. for 1 h. The mixture was diluted with EtOAc (30 mL) and washed with water and brine. The organics extracts were dried over anhydrous MgSO$_4$. The solvents were removed under vacuum and the residue was purified on silica gel (Biogate; eluting solvents hexanes: EtOAc 4/1 ratio) to afford tert-butyl 3-((4'-methoxy-[1,1'-biphenyl]-4-yl)methoxy)azetidine-1-carboxylate as viscous oil (189 mg, 88% yield): $^1$H NMR (500 MHz, CDCl$_3$) δ ppm 7.53 (d, J=8.0 Hz, 2H), 7.51 (d, J=8.5 Hz, 2H), 7.38 (d, J=8.0 Hz, 2H), 6.95 (d, J=8.5 Hz, 2H), 4.47. (s, 2H), 4.33 (m, 1H), 4.08 (dd, J=8.5, 5.0 Hz, 2H), 3.85 (dd, J=8.5, 5.0 Hz, 2H), 1.41 (s, 9H).

Step 3. 3-((4'-Methoxy-[1,1'-biphenyl]-4-yl)methoxy)azetidine TFA salt. Trifluoroacetic acid (0.36 mL, 4.7 mmol) was added into a mixture of tert-butyl 3-((4'-methoxy-[1,1'-biphenyl]-4-yl)methoxy)azetidine-1-carboxylate (175 mg, 0.47 mmol) and CH$_2$Cl$_2$ (10 mL). The mixture was stirred at room temperature for 6 h and then the volatiles were removed under vacuum. The residue was taken (3×) successively in CHCl$_3$ (10 mL) and the volatiles were removed under vacuum to ensure removal of excess TFA. The crude 3-((4'-methoxy-[1,1'-biphenyl]-4-yl)methoxy)azetidine. TFA salt (180 mg) was carried to the next step.

Step 4. 3-((4'-Methoxy-[1,1'-biphenyl]-4-yl)methoxy)azetidine-1-carbonitrile. Triethylamine (0.33 mL, 2.35 mmol) was added into a cold (0° C.) mixture of 3-((4'-methoxy-[1,1'-biphenyl]-4-yl)methoxy)azetidine. TFA salt (180 mg, 0.47 mmol), and CH$_2$Cl$_2$ (8 mL). After stirring for 30 minutes cyanogen bromide (99.5 mg, 0.94 mmol) was added and the mixture was allowed to come to room temperature and stirred for 4 h. Then, the mixture was diluted in EtOAc (30 mL) and washed with water and brine. The organics extracts were dried over anhydrous MgSO$_4$. The solvents were removed under vacuum and the residue was purified on silica gel (Biogate; eluting solvents hexanes: EtOAc 3/1 ratio) to afford 3-((4'-methoxy-[1,1'-biphenyl]-4-yl)methoxy)azetidine-1-carbonitrile as white solid (112 mg, 81% yield): $^1$H NMR (500 MHz, CDCl$_3$) δ ppm 7.55 (d, J=8 Hz, 2H), 7.51 (d, J=8.5 Hz, 2H), 7.34 (d, J=8 Hz, 2H), 6.97 (d, J=8.5 Hz, 2H), 4.47. (s, 2H), 4.41 (m, 1H), 4.24 (dd, J=8.5, 5.0 Hz, 2H), 4.11 (dd, J=8.5, 5.0 Hz, 2H); MS (ES) m/z 295.0904 [M$^+$1]+.

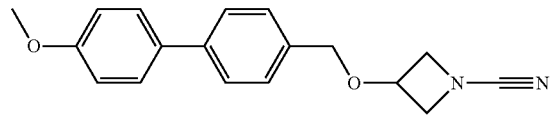 [SMILES: COc1ccc(-c2ccc(COC3CN(C#N)C3)cc2)cc1]

Example 64

3-([1,1'-Biphenyl]-4-ylmethoxy)azetidine-1-carbonitrile: $^1$H NMR (500 MHz, CDCl$_3$) δ ppm 7.6 (m, 4H), 7.42 (m, 2H), 7.39 (m, 3H), 4.47. (s, 2H), 4.41 (m, $^1$H), 4.24 (dd, J=8.5, 5.0 Hz, 2H), 4.11 (dd, J=8.5, 5.0 Hz, 2H); MS (ES) m/z 265.1104 [M+1]$^+$.

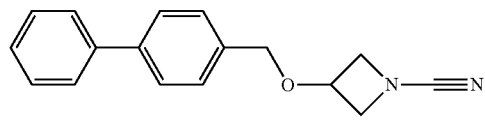 [SMILES: N#CN1CC(OCc2ccc(-c3ccccc3)cc2)C1]

Example 65

3-((2',4'-Dimethoxy-[1,1'-biphenyl]-4-yl)methoxy)azetidine-1-carbonitrile: $^1$H NMR (500 MHz, CDCl$_3$) δ ppm 7.5 (d, J=8.3 Hz, 2H), 7.32 (d, J=7.8 Hz, 2H), 7.22 (d, J=8.3 Hz, $^1$H) 6.56 (m, 2H), 4.47. (s, 2H), 4.41 (m, $^1$H), 4.24 (dd, J=8.6, 5.1 Hz, 2H), 4.11 (dd, J=8.6, 5.1 Hz, 2H), 3.86 (s, 3H), 3.8 (s, 3H); MS (ES) m/z 325.0971 [M$^+$1].

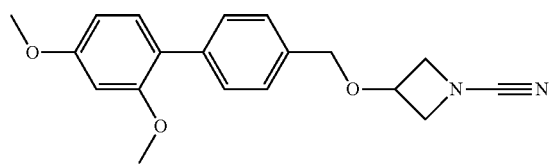 [SMILES: COc1ccc(-c2ccc(COC3CN(C#N)C3)cc2)c(OC)c1]

Example 66

3-([1,1'-Biphenyl]-3-ylmethoxy)azetidine-1-carbonitrile: $^1$H NMR (500 MHz, CDCl$_3$) δ ppm 7.5-7.58 (m, 3H), 7.53 (d, J=1.5 Hz, $^1$H), 7.42-7.47 (m, 3H), 7.37 (m, $^1$H), 7.29 (d, J=7.5 Hz, $^1$H), 4.51 (s, 2H), 4.41 (m, $^1$H), 4.24 (dd, J=8.7, 5.3 Hz, 2H), 4.11 (dd, J=8.7, 5.3 Hz, 2H); MS (ES) m/z 265.1104 [M$^+$1]$^+$.

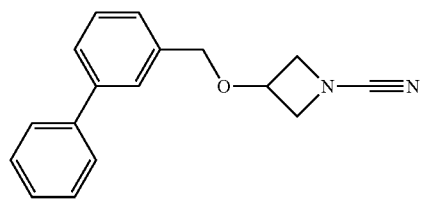 [SMILES: N#CN1CC(OCc2cccc(-c3ccccc3)c2)C1]

Example 67

3-((3'-Methoxy-[1,1'-biphenyl]-4-yl)methoxy)azetidine-1-carbonitrile: $^1$H NMR (500 MHz, CDCl$_3$) δ ppm 7.58 (d, J=8.0 Hz, 2H), 7.37 (d, J=8.0 Hz, 2H), 7.35 (d, J=8.5 Hz, $^1$H), 7.18 (dd, J=8.5, 1.5 Hz, $^1$H), 7.11 (t, J=1.5 Hz, $^1$H), 6.91 (dd, J=8.5, 2.5, Hz, $^1$H), 4.48 (s, 2H), 4.41 (m, $^1$H), 4.24 (dd, J=8.5, 5.0 Hz, 2H), 4.11 (dd, J=8.5, 5.0 Hz, 2H), 3.87 (s, 3H); MS (ES) m/z 295.0785 [M$^+$1]$^+$.

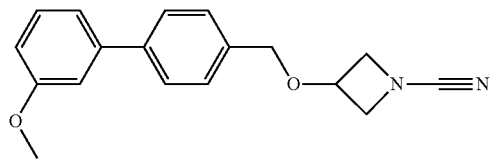 [SMILES: COc1cccc(-c2ccc(COC3CN(C#N)C3)cc2)c1]

Example 68

3-((2',5'-Dimethoxy-[1,1'-biphenyl]-4-yl)methoxy)azetidine-1-carbonitrile: $^1$H NMR (500 MHz, CDCl$_3$) δ ppm 7.54 (d, J=8.5 Hz, 2H), 7.34 (d, J=8.5 Hz, 2H), 6.92 (d, J=9.0 Hz, $^1$H), 6.58-6.89 (m, 2H), 4.48 (s, 2H), 4.41 (m, $^1$H), 4.24 (dd, J=8.6, 5.0 Hz, 2H), 4.11 (dd, J=8.6, 5.0 Hz, 2H), 3.81 (s, 3H), 3.75 (s, 3H); MS (ES) m/z 325.0972 [M$^+$1]$^-$.

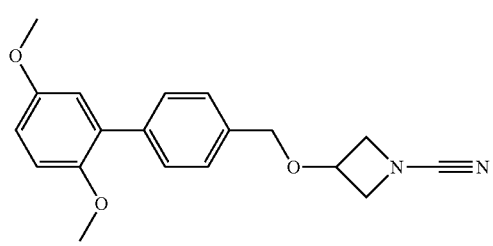 [SMILES: COc1ccc(OC)c(-c2ccc(COC3CN(C#N)C3)cc2)c1]

Example 69

3-((2',3'-Dimethoxy-[1,1'-biphenyl]-4-yl)methoxy)azetidine-1-carbonitrile: $^1$H NMR (500 MHz, CDCl$_3$) δ ppm 7.55 (d, J=8.5 Hz, 2H), 7.36 (d, J=8.5 Hz, 2H), 7.11 (t, J=8.0 Hz, $^1$H), 6.94 (m, 2H), 4.48 (s, 2H), 4.41 (m, $^1$H), 4.24 (dd, J=8.5, 5.0 Hz, 2H), 4.11 (dd, J=8.5, 5.0 Hz, 2H), 3.91 (s, 3H), 3.58 (s, 3H); MS (ES) m/z 325.0975 [M$^+$1]$^-$.

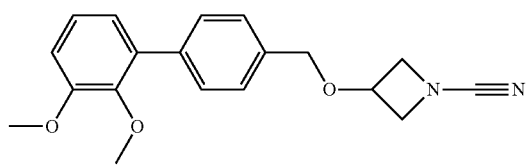 [SMILES: COc1cccc(-c2ccc(COC3CN(C#N)C3)cc2)c1OC]

Example 70

3-((3'-(Trifluoromethyl)-[1,1'-biphenyl]-4-yl)methoxy)azetidine-1-carbonitrile: $^1$H NMR (500 MHz, CDCl$_3$) δ ppm 7.82 (s, $^1$H), 7.76 (d, J=8.0, Hz, $^1$H), 7.56-7.61 (m, 4H), 7.41 (d, J=8.0 Hz, 2H), 7.11 (t, J=8.0 Hz, $^1$H), 6.94 (m, 2H), 4.50 (s, 2H), 4.42 (m, $^1$H), 4.26 (dd, J=8.5, 5.0 Hz, 2H), 4.14 (dd, J=8.5, 5.0 Hz, 2H); MS (ES) m/z 333.0578 [M$^+$1]$^+$.

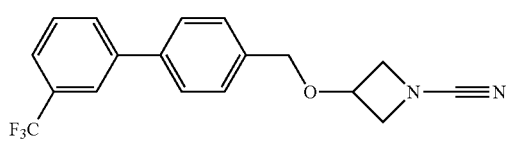 [SMILES: N#CN1CC(OCc2ccc(-c3cccc(C(F)(F)F)c3)cc2)C1]

Example 71

3-((3',5'-Bis(trifluoromethyl)-[1,1'-biphenyl]-4-yl)methoxy)azetidine-1-carbonitrile: $^1$H NMR (500 MHz, CDCl$_3$) δ ppm 8.0 (s, 2H), 7.62 (d, J=8.5, Hz, 2H), 7.46 (d, J=8.5, Hz, 2H), 7.26. (s, $^1$H), 4.51 (s, 2H), 4.43 (m, $^1$H), 4.26 (dd, J=8.5, 5.0 Hz, 2H), 4.14 (dd, J=8.5, 5.0 Hz, 2H); MS (ES) m/z 401.9792 [M$^+$1]$^+$.

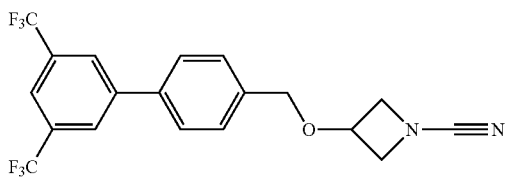

Example 72

3-((4-(Pyridin-3-yl)benzyl)oxy)azetidine-1-carbonitrile: $^1$H NMR (500 MHz, CDCl$_3$) δ ppm 8.85 (d, J=2.0 Hz, $^1$H), 8.6 (dd, J=5.0, 2.0 Hz, $^1$H), 7.88 (d, J=8.0, Hz, $^1$H), 7.59 (d, J=8.5 Hz, 2H), 7.43 (d, J=8.5 Hz, 2H), 7.39 (m, $^1$H), 4.50 (s, 2H), 4.42 (m, $^1$H), 4.26 (dd, J=8.5, 5.0 Hz, 2H), 4.14 (dd, J=8.5, 5.0 Hz, 2H); MS (ES) m/z 266.1086 [M$^+$1]$^+$.

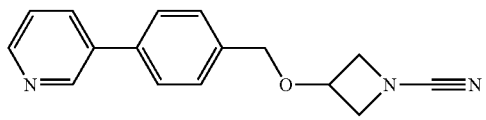

Example 73

3-((4-(6-Methoxypyridin-3-yl)benzyl)oxy)azetidine-1-carbonitrile: $^1$H NMR (500 MHz, CDCl$_3$) δ ppm 8.85 (d, J=5.5 Hz, $^1$H), 8.42 (s, $^1$H), 7.53 (d, J=8.5 Hz, 2H), 7.39 (d, J=8.5 Hz, 2H), 6.91 (d, J=5.5 Hz, $^1$H), 4.49 (s, 2H), 4.42 (m, $^1$H), 4.26 (dd, J=8.5, 5.0 Hz, 2H), 4.14 (dd, J=8.5, 5.0 Hz, 2H), 3.88 (s, 3H); MS (ES) m/z 296.0800 [M$^+$1]$^+$.

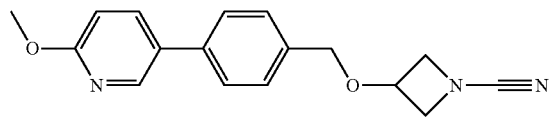

Example 74

3-((4-(2-Methoxypyridin-3-yl)benzyl)oxy)azetidine-1-carbonitrile: $^1$H NMR (500 MHz, CDCl$_3$) δ ppm 8.17 (dd, J=4.88, 1.46 Hz, $^1$H), 7.61 (dd, J=7.0, 2.0 Hz, $^1$H), 7.55 (d, J=8.5 Hz, 2H), 7.37 (d, J=8.5 Hz, 2H), 6.97 (dd, J=7.5, 5.5 Hz, $^1$H), 4.48 (s, 2H), 4.42 (m, $^1$H), 4.26 (dd, J=8.5, 5.5 Hz, 2H), 4.13 (dd, J=8.5, 5.5 Hz, 2H), 3.97 (s, 3H); MS (ES) m/z 296.0818 [M$^+$1]$^+$.

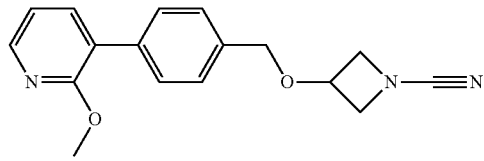 [SMILES: COc1ncccc1-c1ccc(COC2CN(C#N)C2)cc1]

Example 75

3-((2'-Methoxy-[1,1'-biphenyl]-4-yl)methoxy)azetidine-1-carbonitrile: $^1$H NMR (500 MHz, CDCl$_3$) δ ppm 7.53 (d, J=8.5 Hz, 2H), 7.33 (d, J=8.5 Hz, 2H), 7.29-7.31 (m, 2H), 7.04 (dt, J=7.0, 1.0 Hz, $^1$H), 7.01 (d, J=8.0 Hz, $^1$H), 4.48 (s, 2H), 4.42 (m, $^1$H), 4.26 (dd, J=8.5, 5.0 Hz, 2H), 4.13 (dd, J=8.5, 5.0 Hz, 2H), 3.81 (s, 3H); MS (ES) m/z 295.1101 [M$^+$1]$^+$.

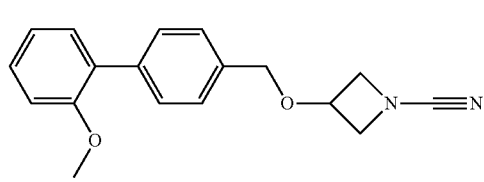 [SMILES: COc1ccccc1-c1ccc(COC2CN(C#N)C2)cc1]

Example 76

3-((4'-Methyl-[1,1'-biphenyl]-4-yl)methoxy)azetidine-1-carbonitrile: $^1$H NMR (500 MHz, CDCl$_3$) δ ppm 7.58 (d, J=8.0 Hz, 2H), 7.48 (d, J=8.5 Hz, 2H), 7.36 (d, J=8.5 Hz, 2H), 7.25 (d, J=8.0 Hz, 2H), 4.48 (s, 2H), 4.42 (m, $^1$H), 4.26 (dd, J=8.5, 5.5 Hz, 2H), 4.13 (dd, J=8.5, 5.5 Hz, 2H), 2.4 (s, 3H); MS (ES) m/z 279.1124 [M$^+$1]$^+$.

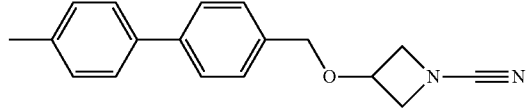 [SMILES: Cc1ccc(-c2ccc(COC3CN(C#N)C3)cc2)cc1]

Example 77

3-((4'-Fluoro-[1,1'-biphenyl]-4-yl)methoxy)azetidine-1-carbonitrile: $^1$H NMR (500 MHz, CDCl$_3$) δ ppm 7.52-7.55 (m, 4H), 7.38 (d, J=8.0 Hz, 2H), 7.12-7.15 (m, 2H), 4.48 (s, 2H), 4.42 (m, $^1$H), 4.26 (dd, J=8.5, 5.5 Hz, 2H), 4.13 (dd, J=8.5, 5.5 Hz, 2H), 2.4 (s, 3H); MS (ES) m/z 283.0827 [M$^+$1]$^+$.

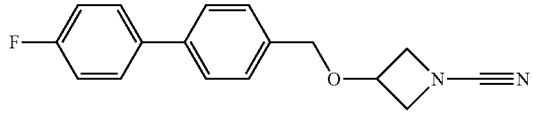 [SMILES: N#CN1CC(OCc2ccc(-c3ccc(F)cc3)cc2)C1]

Example 78

3-((3-Fluoro-3'-methoxy-[1,1'-biphenyl]-4-yl)methoxy)azetidine-1-carbonitrile: $^1$H NMR (500 MHz, CDCl$_3$) δ ppm 7.35-7.41 (m, 3H), 7.28 (dd, J=11.0, 2.0 Hz, $^1$H), 7.15 (d, J=8.5 Hz, ¹H), 7.08 (t, J=1.5 Hz, ¹H), 6.94 (dd, J=8.5, 2.5 Hz, ¹H), 4.45 (m, ¹H), 4.27 (dd, J=8.5, 5.5 Hz, 2H), 4.12 (dd, J=8.5, 5.5 Hz, 2H), 3.87 (s, 3H); MS (ES) m/z 313.0823 [M+1]+.

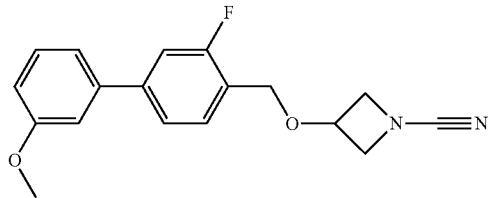 [SMILES: COc1cccc(-c2ccc(COC3CN(C#N)C3)c(F)c2)c1]

Example 79

3-((3'-Methoxy-3-(trifluoromethyl)-[1,1'-biphenyl]-4-yl) methoxy)azetidine-1-carbonitrile: ¹H NMR (500 MHz, CDCl₃) δ ppm 7.86 (d, J=1.5 Hz, ¹H), 7.78 (d, J=8.0 Hz, ¹H), 7.68 (d, J=8.0 Hz, ¹H), 7.39 (t, J=8.0 Hz, ¹H), 7.18 (dd, J=8.0, 1.0 Hz, ¹H), 7.1 (t, J=1.5 Hz, ¹H), 6.94 (m, ¹H), 4.64 (s, 2H), 4.45 (m, ¹H), 4.32 (dd, J=8.5, 5.5 Hz, 2H), 4.18 (dd, J=8.5, 5.5 Hz, 2H), 3.88 (s, 3H); MS (ES) m/z 363.0270 [M+1]+.

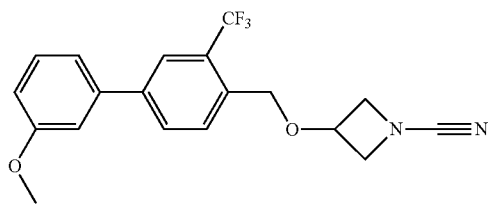 [SMILES: COc1cccc(-c2ccc(COC3CN(C#N)C3)c(C(F)(F)F)c2)c1]

Example 80

3-((3,3'-Dimethoxy-[1,1'-biphenyl]-4-yl)methoxy)azetidine-1-carbonitrile: ¹H NMR (500 MHz, CDCl₃) δ ppm 7.33-7.38 (m, 2H), 7.16-7.18 (m, 2H), 7.1 (m, ¹H), 7.1 (t, J=1.5 Hz, ¹H), 7.07 (d, J=1.5 Hz, ¹H), 6.91-6.93 (m, ¹H), 4.51 (s, 2H), 4.45 (m, ¹H), 4.25 (dd, J=8.5, 5.5 Hz, 2H), 4.12 (dd, J=8.5, 5.5 Hz, 2H), 3.91 (s, 3H), 3.87 (s, 3H); MS (ES) m/z 325.0850 [M+1]+.

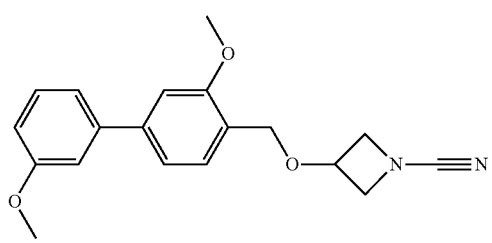 [SMILES: COc1cccc(-c2ccc(COC3CN(C#N)C3)c(OC)c2)c1]

Example 81

3-((4-Phenoxybenzyl)oxy)azetidine-1-carbonitrile: ¹H NMR (500 MHz, CDCl₃) δ ppm 7.32-7.38 (m, 2H), 7.26-7.29 (m, 3H), 7.12 (dt, J=7.5, 1.0 Hz, ¹H), 6.98-7.02 (m, 3H), 4.41 (s, 2H), 4.38 (m, ¹H), 4.23 (dd, J=8.5, 5.5 Hz, 2H), 4.09 (dd, J=8.5, 5.5 Hz, 2H).

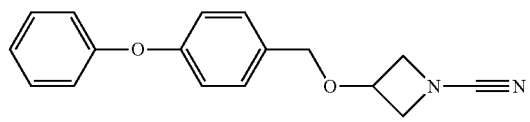 [SMILES: N#CN1CC(OCc2ccc(Oc3ccccc3)cc2)C1]

Example 82

3-((1-(3'-Methoxy-[1,1'-biphenyl]-4-yl)cyclopropyl) methoxy)azetidine-1-carbonitrile: ¹H NMR (500 MHz, CDCl₃) δ ppm 7.52 (d, J=8.5, ¹H), 7.33-7.38 (m, 3H), 7.17 (dd, J=7.0, 1.5 Hz, ¹H), 7.11 (d, J=8.5 Hz, ¹H), 6.88 (dd, J=7.0, 1.5 Hz, ¹H), 4.26 (m, ¹H), 4.19 (dd, J=8.5, 5.5 Hz, 2H), 4.09 (dd, J=8.5, 5.5 Hz, 2H), 3.86 (s, 2H), 0.96 (m, ¹H), 0.873 (m, ¹H); MS (ES) m/z 335.0792 [M+1]+.

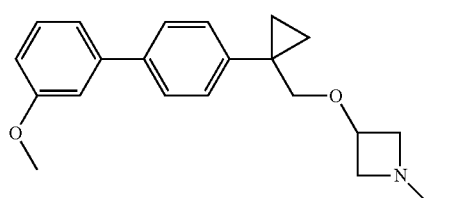

Example 83

3-((2',6'-Dimethoxy-[1,1'-biphenyl]-4-yl)methoxy)azetidine-1-carbonitrile ¹H NMR (500 MHz, CDCl₃) δ ppm 7.34-7.33 (m, 4H), 7.28 (t, J=7.5 Hz, 1H), 6.66 (d, J=8.5, 2H), 4.48 (s, 2H), 4.44-4.18 (m, 1H), 4.25-4.22 (m, 2H), 4.12-4.1 (m, 2H), 3.73 (s, 6H).

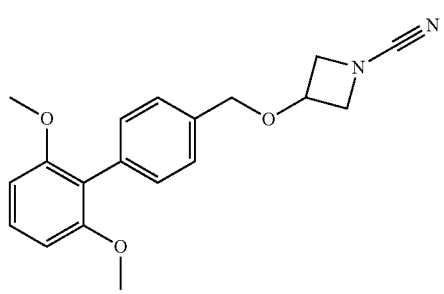 [SMILES: COc1cccc(OC)c1-c1ccc(COC2CN(C#N)C2)cc1]

Example 84

3-((4-(2,3-Dihydrobenzo[b][1,4]dioxin-6-yl)benzyl)oxy) azetidine-1-carbonitrile. ¹H NMR (500 MHz, CDCl₃) δ ppm 7.53 (dd, J=8.0, 1.5 Hz, 2H), 7.34 (d, J=8.0 Hz, 2H), 7.1 (d, J=2.5 Hz, 1H), 7.08 (dd, J=8.5, 2.0 Hz, 1H), 6.94 (d, J=8.5 Hz, 1H), 4.46 (s, 2H), 4.42-4.38 (m, 1H), 4.3 (s, 2H), 4.25-4.22 (m, 2H), 4.12-4.1 (m, 2H).

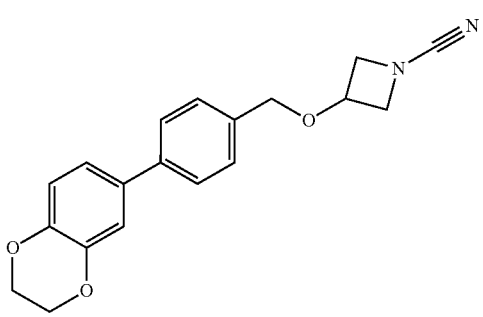 [SMILES: N#CN1CC(OCc2ccc(-c3ccc4c(c3)OCCO4)cc2)C1]

Example 85

3-((3'-(Benzyloxy)-[1,1'-biphenyl]-4-yl)methoxy)azetidine-1-carbonitrile. $^1$H NMR (500 MHz, CDCl$_3$) δ ppm 7.58 (dd, J=7.5, 2.0 Hz, 2H), 7.47 (m, 2H), 7.41-7.34 (m, 6H), 7.2-7.17 (m, 2H), 6.99 (dd, J=8.0, 2.5 Hz, 1H), 5.13 (s, 2H), 4.48 (s, 2H), 4.43-4.39 (m, 1H), 4.26-4.23 (m, 2H), 4.13-4.1 (m, 2H).

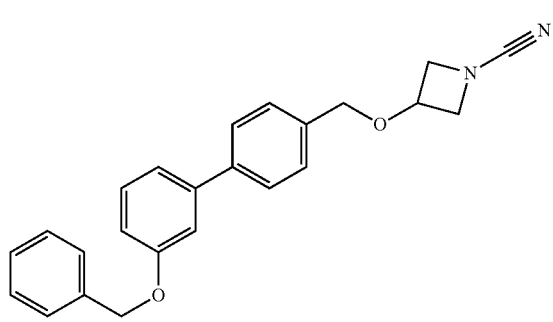 [SMILES: N#CN1CC(OCc2ccc(-c3cccc(OCc4ccccc4)c3)cc2)C1]

Method M.

The hydroxy-methyl azetidine 4 (Scheme 15) was prepared through a reduction process of an ester functionality using sodium borohydride as the hydride source. Following similar protocols as described in Method L, alcohol 7 was converted to final products 4.

Scheme 15:

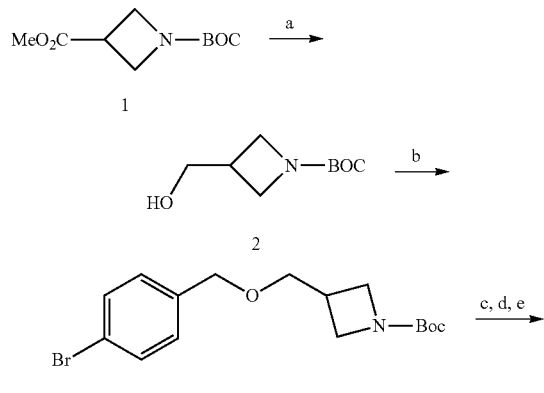

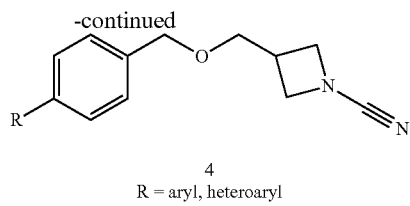

4
R = aryl, heteroaryl

Reagents: a: NaBH$_4$, MeOH, THF; b: Ar—CH$_2$Br, NaH, DMF; c: R—B(OH)$_2$, K$_2$CO$_3$, Pd(PPh$_3$)$_4$, dioxane, H$_2$O; d: TFA, CH$_2$Cl$_2$; e: CNBr, Et$_3$N, CH$_2$Cl$_2$ The following example was prepared according to Method M.

Example 86

3-((([1,1'-Biphenyl]-4-ylmethoxy)methyl)azetidine-1-carbonitrile. Step 1. tert-Butyl 3-(hydroxymethyl)azetidine-1-carboxylate. Sodium borohydride (756 mg, 20 mmol) was added portionwise into a solution of 1-(tert-butyl) 3-methyl azetidine-1,3-dicarboxylate (2.11 g, 10 mmol) and THF (10 mL). The mixture was heated to 80° C. and then MeOH (2 mL) was added very slowly over a 30 minute period. The mixture was stirred for 1 hour, cooled to room temperature and poured slowly into ice-cold HCl (0.5 N). The mixture was extracted (3×) with EtOAc and the organic extracts were dried over anhydrous MgSO$_4$. The solvents were removed under vacuum and the residue was purified on silica gel (Biogate; eluting solvents hexanes: EtOAc 2/1 ratio) to afford tert-butyl 3-(hydroxymethyl)azetidine-1-carboxylate as oil (1.69 g, 90% yield): $^1$H NMR (500 MHz, CDCl$_3$) δ ppm 3.98 (t, J=8.3, 2H), 3.77 (m, 2H), 3.68 (dd, J=8.77, 5.37 Hz, 2H), 2.7 (m, $^1$H).

Step 2. 3-((([1,1'-Biphenyl]-4-ylmethoxy)methyl)azetidine-1-carbonitrile. Compound of Example 86 was prepared from tert-butyl 3-(hydroxymethyl)azetidine-1-carboxylate and according to Method L using phenyl boronic acid to afford 3-((([1,1'-biphenyl]-4-ylmethoxy)methyl)azetidine-1-carbonitrile as white solid. $^1$H NMR (500 MHz, CDCl$_3$) δ ppm 7.6 (m, 4H), 7.44 (m, 2H), 7.39 (m, 3H), 4.21 (t, J=7.81, Hz, 2H), 4.0 (dd, J=7.81, 5.86 Hz, 2H), 3.6 (d, J=6.35 Hz, $^1$H), 2.98 (m, $^1$H); MS (ES) m/z 279.0874 [M$^+$1]$^+$.

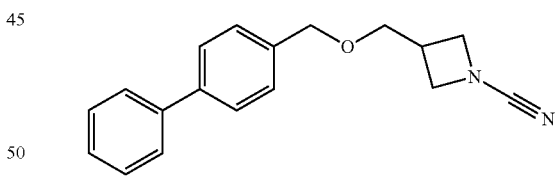

Method N.

The phenoxy azetidines 8 were prepared according to Scheme 16. Coupling of benzaldehyde 1 with phenol using an inorganic base, as potassium carbonate, in a polar solvent, as N,N-dimethylformamide produced adduct 2, which was further reduced with sodium borohydride to give benzylic alcohol 3. Treatment of 3 with phosphorus tribromide, in an aprotic solvent as tetrahydrofuran produced benzyl bromide 4. Coupling of benzyl bromide 4 with tert-butyl 3-hydroxyazetidine-1-carboxylate was accomplished upon treatment with a base such as sodium hydride in an aprotic polar solvent as N,N-dimethylformamide to yield 5. Unmasking of the azetidine nitrogen of 5 to generate 6 was achieved upon treatment with a strong organic acid as trifluoroacetic acid in a chlorinated solvent such as dichloromethane.

Cyanamides 7 were prepared upon treatment of 6 with cyanogen bromide and an organic base such as triethylamine in an inert solvent as dichloromethane. Palladium mediated cross-coupling reaction between cyanamide 7 and the appropriate boronic acid was used to generate phenoxy analog 8. Palladium catalysts suitable for use in the process of the disclosure include Pd(0) or Pd(II) catalysts such as dichlorobis(tri-o-tolylphosphine)palladium(II), tetrakis(triphenylphosphine)palladium(0), or the like. Cesium fluoride was used as the base under anhydrous conditions in dimethoxyethane as the solvent.

Scheme 16:

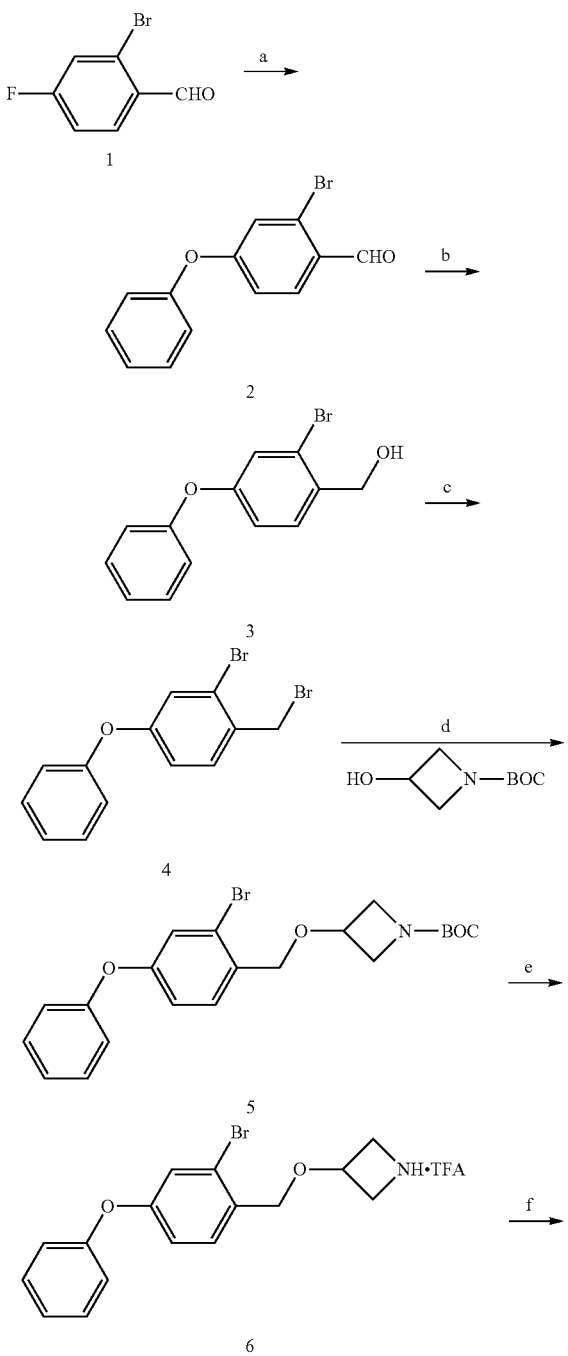

Reagents: (a) 4-F, 2 Br benzaldehyde, K₂CO₃, DMF; (b) NaBH₄, MeOH; (c) PBr₃, THF; (d) NaH, DMF; (e) TFA, CH₂Cl₂; (f) CNBr, Et₃N, CH₂Cl₂; (g) Ar—B(OH)₂, CsF, Pd(PPh₃)₄, dimethoxyethane The following examples were prepared according Method N.

Example 87

3-((5-Phenoxy-[1,1'-biphenyl]-2-yl)methoxy)azetidine-1-carbonitrile. Step 1. 2-Bromo-4-phenoxybenzaldehyde. Potassium carbonate (5.98 g, 43.28 mmol) was added into a mixture of phenol (2.31 g, 24.6 mmol), 2-bromo-4-fluorobanzaldehyde and DMF (50 mL). The mixture was stirred at 100° C. for 18 hours, cooled to room temperature and then poured into water (200 mL). The mixture was stirred for 30 minutes and the precipitated solid filtered and washed with water. 2-Bromo-4-phenoxybenzaldehyde as an off-white sold (6.15 g, 90% yield) was collected and used to the next step. $^1$H NMR (500 MHz, CDCl₃) δ ppm 10.24 (s, 1H), 7.9 (d, J=9.0 Hz, 1H), 7.45-7.42 (m, 2H), 7.27 (t, J=7.5 Hz, 1H), 7.17 (d, J=2.5 Hz, 1H), 7.09-7.08 (m, 2H), 6.98 (dd, J=9.0, 2.5 Hz, 1H).

Step 2. (2-Bromo-4-phenoxyphenyl)methanol. Sodium borohydride (544.3 mg, 14.4 mmol) was added in portions into a cold (0° C.) mixture of 2-bromo-4-phenoxybenzaldehyde (6.25 g, 22.56 mmol) and anhydrous methanol (30 mL). After the addition the mixture stirred for 30 minutes, and then it was carefully poured into ice water. The mixture was extracted with ethyl acetate and the organic extracts washed with water and brine and dried over anhydrous MsSO₄. The solvents were removed under vacuum and the residue was purified on silica gel (Biotage; eluting solvents hexanes: EtOAc 3/1 ratio) to afford (2-bromo-4-phenoxyphenyl)methanol as oil (5.92 g, 94.4% yield): $^1$H NMR (500 MHz, CDCl₃) δ ppm 7.42 (d, J=8.5 Hz, 1H), 7.38-7.34 (m, 4H), 7.2 (d, J=2.5 Hz, 1H), 7.16 (t, J=7.5 Hz, 1H), 7.0 (dd, J=8.5, 2.5 Hz, 1H), 4.71 (d, J=6.5 Hz, 2H), 1.97 (t, J=6.5 Hz, 1H).

Step 3. 2-Bromo-1-(bromomethyl)-4-phenoxybenzene. Phosphorus tribromide (4.3 mL, 44.74 mmol) was added dropwise into a cold (0° C.) mixture of (2-bromo-4-phenoxyphenyl)methanol (4.9 g, 17.56 mmol) and anhydrous tetrahydrofuran (50 mL). After the addition the mixture stirred at room temperature for 5 hours, and then it was carefully poured into ice water. The mixture was extracted with ethyl acetate and the organic extracts washed with saturated aqueous sodium bicarbonate (three times), water and brine and dried over anhydrous MgSO₄. The solvents were removed under vacuum and the residue was purified on silica gel (Biotage; eluting solvents hexanes: EtOAc 30/1 ratio) to afford 2-bromo-1-(bromomethyl)-4-phenoxybenzene as oil (4.26 g, 71% yield): ¹H NMR (500 MHz, CDCl₃) δ ppm 7.4-7.36 (m, 3H), 7.19-7.16 (m, 2H), 7.04-7.03 (m, 2H), 6.92 (dd, J=8, 2.5 Hz, 1H), 4.6 (s, 2H).

Step 4. tert-Butyl 3-((2-bromo-4-phenoxybenzyl)oxy)azetidine-1-carboxylate. Sodium hydride (60% dispersion in mineral oil; 300 mg, 7.51 mmol) was added portionwise into a cold (0° C.) solution of tert-butyl 3-hydroxyazetidine-1-carboxylate (1.0 g, 5.78 mmol) and DMF (15 mL). After stirring for 1 hour, 2-bromo-1-(bromomethyl)-4-phenoxybenzene (2.11 g, 6.17 mmol) was added and the mixture was allowed to come to room temperature and stirred for 3 hours. The mixture was carefully poured into saturated aqueous ammonium chloride and extracted with ethyl ether (2×). The organic extracts were dried over anhydrous MgSO₄. The solvents were removed under vacuum and the residue was purified on silica gel (Biotage; eluting solvents hexanes: EtOAc 3/1 ratio) to afford tert-butyl 3-((2-bromo-4-phenoxybenzyl)oxy)azetidine-1-carboxylate as oil (1.89 g, 75.6% yield): ¹H NMR (500 MHz, CDCl₃) δ ppm 7.4-7.35 (m, 3H), 7.19 (d, J=2.5 Hz, 1H), 7.15 (t, J=7.5 Hz, 1H), 7.03-7.0 (m, 2H), 6.97 (dd, J=8.0, 2.5 Hz, 1H), 4.48 (s, 2H), 4.37-4.34 (m, 1H), 4.11-4.08 (m, 2H), 3.92-3.89 (m, 2H), 1.44 (s, 9H).

Step 5. 3-((2-Bromo-4-phenoxybenzyl)oxy)azetidine. TFA salt. Trifluoroacetic acid (0.31 mL, 4.0 mmol) was added into a mixture of 3-((2-bromo-4-phenoxybenzyl)oxy)azetidine-1-carboxylate (173.4 mg, 0.4 mmol) and CH₂Cl₂ (10 mL). The mixture was stirred at room temperature for 6 h and then the volatiles were removed under vacuum. The residue was successively taken (3×) in CHCl₃ (10 mL) and the volatiles were removed under vacuum to ensure removal of excess TFA. The crude 3-((2-bromo-4-phenoxybenzyl)oxy)azetidine. TFA salt (179 mg) was carried to the next step.

Step 6. 3-((2-Bromo-4-phenoxybenzyl)oxy)azetidine-1-carbonitrile. Triethylamine (0.28 mL, 2.0 mmol) was added into a cold (0° C.) mixture of 3-((2-bromo-4-phenoxybenzyl)oxy)azetidine. TFA salt (179 mg, 0.4 mmol) and CH₂Cl₂ (7 mL). After stirring for 30 minutes cyanogen bromide (84.7 mg, 0.8 mmol) was added and the mixture was allowed to come to room temperature and stirred for 2 h. Then, the mixture was diluted in EtOAc (30 mL) and washed with water and brine. The organics extracts were dried over anhydrous MgSO4. The solvents were removed under vacuum and the residue was purified on silica gel (Biotage; eluting solvents hexanes: EtOAc 3/1 ratio) to afford 3-((2-bromo-4-phenoxybenzyl)oxy)azetidine-1-carbonitrile as oil (109 mg, 76.2% yield): ¹H NMR (500 MHz, CDCl₃) δ ppm 7.39-7.34 (m, 3H), 7.19 (d, J=2.5 Hz, 1H), 7.17 (t, J=7.5 Hz, 1H), 7.03-7.0 (m, 2H), 6.97 (dd, J=8.0, 2.5 Hz, 1H), 4.48 (s, 2H), 4.46-4.43 (m, 1H), 4.3-4.27 (m, 2H), 4.16-4.13 (m, 2H).

Step 7. 3-((5-Phenoxy-[1,1'-biphenyl]-2-yl)methoxy)azetidine-1-carbonitrile. Into a microwave vessel were added 3-((2-bromo-4-phenoxybenzyl)oxy)azetidine-1-carbonitrile (120 mg, 0.33 mmol), phenylboronic acid (60.4 mg, 0.49 mmol), cesium fluoride (100.3 mg, 0.66 mmol) and anhydrous dimethoxyethane (4 mL). Dry argon gas was passed through the mixture for 10 minutes and then tetrakis(triphenylphosphine)palladium(0) (12.4 mg 0.0099 mmol) was added and the argon flow continued for 5 additional minutes. Then, the vessel was sealed and microwaved at 100° C. for 1 hour. The mixture was diluted with EtOAc (30 mL) and washed with water and brine. The organics extracts were dried over anhydrous MgSO₄. The solvents were removed under vacuum and the residue was purified on silica gel (Biotage; eluting solvents hexanes: EtOAc 3/1 ratio) to afford 3-((5-phenoxy-[1,1'-biphenyl]-2-yl)methoxy)azetidine-1-carbonitrile as oil (94.6 mg, 79% yield): ¹H NMR (500 MHz, CDCl₃) δ ppm 7.44-7.39 (m, 4H), 7.38-7.31 (m, 4H), 7.14 (dt, J=7.5 Hz, 1.5 Hz, 1H), 7.07-7.05 (m, 2H), 7.01 (dd, J=8.0, 2.5 Hz, 1H), 6.94 (d, J=2.5 Hz, 1H), 4.26 (s, 2H), 4.25-4.2 (m, 1H), 4.14-4.11 (m, 2H), 3.94-3.91 (m, 2H).

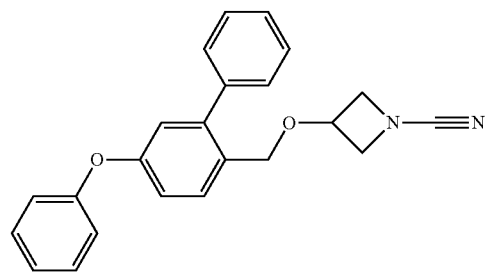 [SMILES: N#CN1CC(OCc2ccc(Oc3ccccc3)cc2-c2ccccc2)C1]

Example 88

3-((2'-Methoxy-5-phenoxy-[1,1'-biphenyl]-2-yl)methoxy)azetidine-1-carbonitrile: ¹H NMR (500 MHz, CDCl₃) δ ppm 7.41 (d, J=8.5 Hz, 1H), 7.36-7.33 (m, 3H), 7.16 (dd, J=7.5 Hz, 1.5 Hz, 1H), 7.16 (dt, J=7.5 Hz, 1.5 Hz, 1H), 7.07-7.05 (m, 2H), 7.03-6.95 (m, 3H), 6.89 (d, J=2.5 Hz, 1H), 4.23 (m, 1H), 4.15-4.12 (m, 2H), 4.05 (t, J=7.5 Hz, 2H), 3.8 (m, 2H), 3.76 (s, 3H).

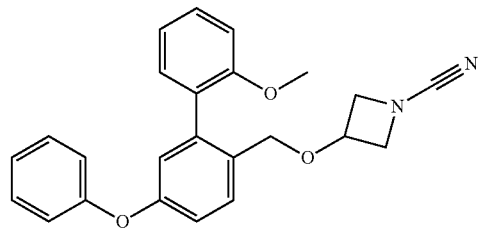 [SMILES: COc1ccccc1-c1cc(Oc2ccccc2)ccc1COC1CN(C#N)C1]

Example 89

3-((3'-Methoxy-5-phenoxy-[1,1'-biphenyl]-2-yl)methoxy)azetidine-1-carbonitrile: ¹H NMR (500 MHz, CDCl₃) δ ppm 7.41 (d, J=8.5 Hz, 1H), 7.36-7.32 (m, 3H), 7.14 (dt, J=7.5 Hz, 1.5 Hz, 1H), 7.06-7.04 (m, 2H), 7.01 (dd, J=8.0, 2.5 Hz, 1H), 6.95 (d, J=2.5 Hz, 1H), 6.92-6.88 (m, 3H), 4.27 (s, 2H), 4.26-4.24 (m, 1H), 4.17 (t, J=8.5 Hz, 2H), 3.98-3.95 (m, 2H), 3.85 (s, 3H).

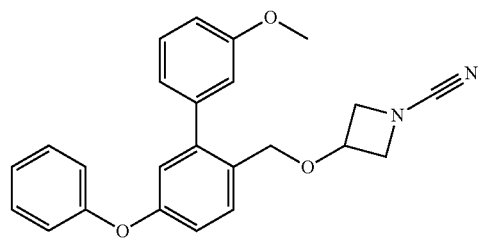 [SMILES: COc1cccc(-c2cc(Oc3ccccc3)ccc2COC2CN(C#N)C2)c1]

Example 90

3-((4'-Methoxy-5-phenoxy-[1,1'-biphenyl]-2-yl)methoxy)azetidine-1-carbonitrile: $^1$H NMR (500 MHz, CDCl$_3$) δ ppm 7.39 (d, J=8.0 Hz, 1H), 7.36-7.33 (m, 2H), 7.27-7.25 (m, 2H), 7.12 (dt, J=7.5 Hz, 1.5 Hz, 1H), 7.06-7.04 (m, 2H), 6.98-6.92 (m, 4H), 4.27 (s, 2H), 4.26-4.24 (m, 1H), 4.17 (t, J=8.5 Hz, 2H), 3.98-3.95 (m, 2H), 3.85 (s, 3H).

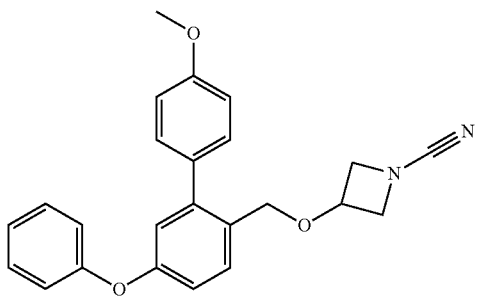 [SMILES: COc1ccc(-c2cc(Oc3ccccc3)ccc2COC2CN(C#N)C2)cc1]

Example 91

3-((2-(2-Methoxypyridin-3-yl)-4-phenoxybenzyl)oxy)azetidine-1-carbonitrile: $^1$H NMR (500 MHz, CDCl$_3$) δ ppm 8.22 (dd, J=5.5, 2.0 Hz, 1H), 7.48 (dd, J=7.0, 2.0 Hz, 1H), 7.42 (d, J=8.5 Hz, 1H), 7.37 (t, J=7.0 Hz, 2H), 7.13 (t, J=7.5 Hz, 1H), 7.07-7.03 (m, 2H), 7.02 (dd, J=8.5, 2.5 Hz, 1H), 6.98 (m, 1H), 6.88 (d, J=2.0 Hz, 1H), 4.22-4.16 (m, 3H), 4.12 (t, J=8.5 Hz, 2H), 3.9 (s, 3H), 3.89-3.85 (m, 2H).

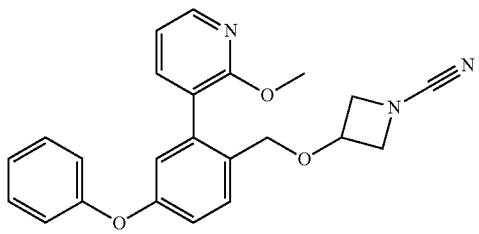 [SMILES: COc1ncccc1-c1cc(Oc2ccccc2)ccc1COC1CN(C#N)C1]

Example 92

3-((4'-Cyano-5-phenoxy-[1,1'-biphenyl]-2-yl)methoxy)azetidine-1-carbonitrile: $^1$H NMR (500 MHz, CDCl$_3$) δ ppm 7.73 (dd, J=8.0, 2.0 Hz, 2H), 7.48 (dd, J=8.0, 2.0 Hz, 2H), 7.42 (d, J=8.5 Hz, 1H), 7.37 (t, J=7.5 Hz, 2H), 7.17 (t, J=7.5 Hz, 1H), 7.07-7.03 (m, 3H), 6.91 (d, J=2.5 Hz, 1H), 4.29-4.26 (m, 1H), 4.22-4.19 (m, 4H), 4.0-3.98 (m, 2H).

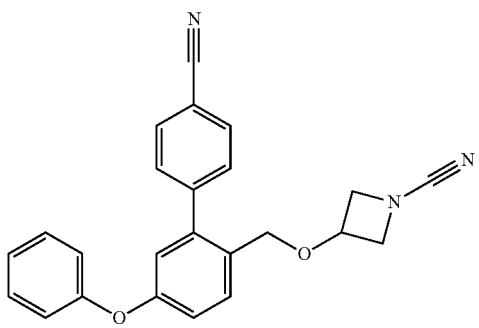 [SMILES: N#Cc1ccc(-c2cc(Oc3ccccc3)ccc2COC2CN(C#N)C2)cc1]

Example 93

3-((2'-Cyano-5-phenoxy-[1,1'-biphenyl]-2-yl)methoxy)azetidine-1-carbonitrile: $^1$H NMR (500 MHz, CDCl$_3$) δ ppm 7.76 (dd, J=8.0, 1.5 Hz, 1H), 7.67 (dt, J=8.0, 1.5 Hz, 1H), 7.52 (dt, J=8.0, 1.5 Hz, 1H), 7.44-7.41 (m, 2H), 7.38-7.34 (m, 2H), 7.13 (t, J=7.5 Hz, 1H), 7.09-7.07 (m, 3H), 6.91 (d, J=2.0 Hz, 1H), 4.25-4.17 (m, 2H), 4.15-4.12 (m, 3H), 3.83-3.79 (m, 2H).

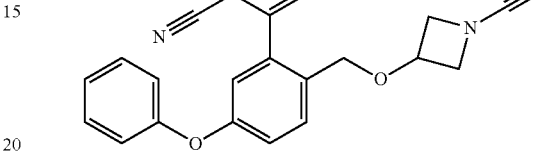

Example 94

3-((4-(Bis(4-fluorophenyl)methoxy)-2-bromobenzyl)oxy)azetidine-1-carbonitrile. This compound was prepared according to example 87 (Method N) with the modification of using bis(4-fluorophenyl)methanol at the first coupling step instead of phenol and sodium hydride as the base. Sodium hydride (60% dispersion in mineral oil; 217 mg, 5.44 mmol) was added portionwise into a cold (0° C.) solution of bis(4-fluorophenyl)methanol (1.0 g, 4.54 mmol) and DMF (10 mL). After stirring for 1 hour, 2-bromo-1-(bromomethyl)-4-phenoxybenzene (0.92 g, 4.54 mmol) was added and the mixture was allowed to come to room temperature and stirred for 3 hours. The mixture was carefully poured into saturated aqueous ammonium chloride and extracted with ethyl ether (2×). The organic extracts were dried over anhydrous MgSO$_4$. The solvents were removed under vacuum and the residue was purified on silica gel (Biotage; eluting solvents hexanes: EtOAc 4/1 ratio) to afford 4-(bis(4-fluorophenyl)methoxy)-2-bromobenzaldehyde as oil (0.67 g, 37.2% yield): $^1$H NMR (500 MHz, CDCl$_3$) δ ppm 10.1 (s, 1H), 7.83 (d, J=90 Hz, 1H), 7.35-7.32 (m, 4H), 7.19 (d, J=2.5 Hz, 1H), 7.08-7.04 (m, 4H), 6.96 (dd, J=9.0, 2.5 Hz, 1H), 6.26 (s, 1H).

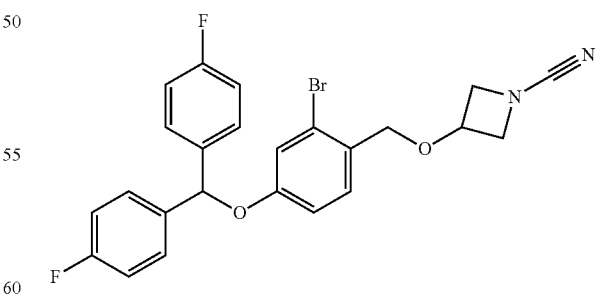

Following similar processes outlined in Method N, elaboration of 4-(bis(4-fluorophenyl)methoxy)-2-bromobenzaldehyde afforded 3-((4-(bis(4-fluorophenyl)methoxy)-2-bromobenzyl)oxy)azetidine-1-carbonitrile. $^1$H NMR (500 MHz, CDCl$_3$) δ ppm 7.34 (m, 4H), 7.24 (d, J=9.0 Hz, 1H), 7.17 (d, J=2.5 Hz, 1H), 7.06-7.03 (m, 4H), 6.87 (dd, J=9.0, 3.0 Hz, 1H), 6.16 (s, 1H), 4.41 (s, 2H), 4.41-4.38 (m, 1H), 4.25-4.22 (m, 2H), 4.11-4.08 (m, 2H).

Method O.

The spiro-azetidines 6 and 7 were prepared according to scheme 17. Treatment 3-oxoazetidine 1 with either alkyl or aryl Grignard reagents and alkyl or aryl lithium reagents produced alcohol 2. Coupling of alcohol 2 under base-transfer conditions (sodium hydroxide, tetrabutyl ammonium bromide) with aryl-alkyl halides afforded azetidine 3. Azetidine 3 was transformed to the desired spiro-azetidines 6 by following the same processes as described in Method L and N.

with aqueous ammonium chloride. The mixture was extracted with ethyl acetate, washed with brine and dried over anhydrous $MgSO_4$. The solvents were removed under vacuum and the residue was purified on silica gel (Biotage; eluting solvents hexanes: EtOAc 1/1 ratio) to afford tert-butyl 3-hydroxy-3-methylazetidine-1-carboxylate as oil (480 mg, 87% yield): $^1$H NMR (500 MHz, $CDCl_3$) δ ppm 3.87 (d, J=9.0 Hz, 2H), 3.82 (d, J=9.0, 2H), 2.46 (s, 1H), 1.51 (s, 3H), 1.44 (s, 9H).

Step b. tert-Butyl 3-((4-bromobenzyl)oxy)-3-methylazetidine-1-carboxylate. Into a mixture of tert-butyl 3-hydroxy-3-methylazetidine-1-carboxylate (480 mg, 2.56 mmol), Scheme 17:

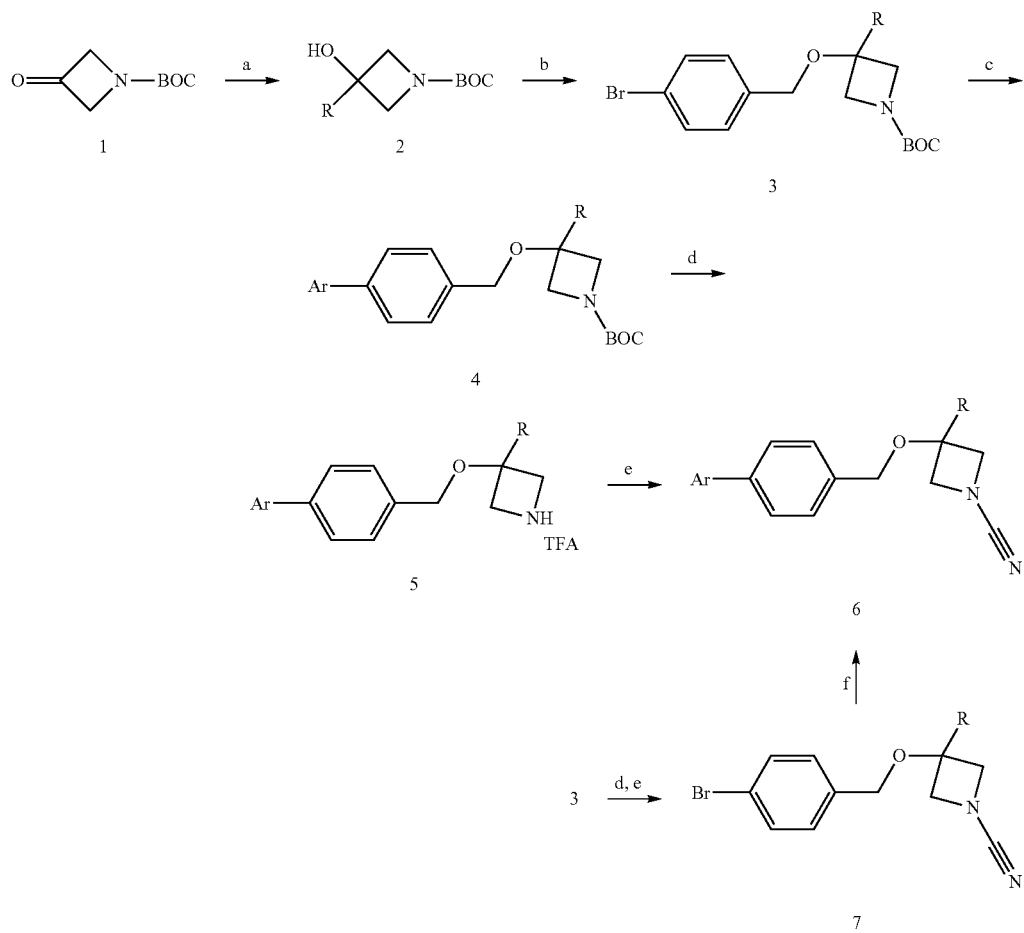

Reagents: (a) RMgBr or Ar—Li, THF; (b) 4N NaOH, Bu₄NBr, 4-Br-benzyl bromide, CH₂Cl₂; (c) Ar—B(OH)₂, K₂CO₃, Pd(PPh₃)₄, dioxane, H₂O; (d) TFA, CH₂Cl₂; (e) CNBr, Et₃N, CH₂Cl₂; (f) Ar—B(OH)₂, CsF, Pd(PPh₃)₄, dimethoxyethane The following examples were prepared according to Method O.

Example 95

3-((3'-Methoxy-[1,1'-biphenyl]-4-yl)methoxy)-3-methyl-azetidine-1-carbonitrile. Step a. tert-Butyl 3-hydroxy-3-methylazetidine-1-carboxylate. Methyl magnesium bromide (3M in diethyl ether; 2.92 mL, 8.76 mmol) was added portionwise into a cold (0° C.) solution of tert-butyl 3-oxoazetidine-1-carboxylate (0.5 g, 2.92 mmol) and anhydrous THF (3 mL). The mixture was allowed to come to room temperature and stirred for 3 hours and carefully quenched 1-bromo-4-(bromomethyl)benzene and dichloromethane (5 mL) were added NaOH (4N, 6 mL) and tetra-n-butylammonium bromide (82.6 mg, 0.256 mmol). The mixture was refluxed for 16 hours, cooled to room temperature and extracted with ethyl ether. The organic extracts were washed with water and brine and dried over anhydrous $MgSO_4$. The solvents were removed under vacuum and the residue was purified on silica gel (Biotage; eluting solvents hexanes: EtOAc 3/1 ratio) to afford tert-butyl 3-((4-bromobenzyl)oxy)-3-methylazetidine-1-carboxylate as oil (826 mg, 90.5% yield): $^1$H NMR (500 MHz, $CDCl_3$) δ ppm 7.48 (d, J=8.5 Hz, 2H), 7.22 (d, J=8.5 Hz, 2H), 4.38 (s, 2H), 3.98 (d, J=9.5 Hz, 2H), 3.74 (d, J=9.5 Hz, 2H), 1.55 (s, 3H), 1.44 (s, 9H).

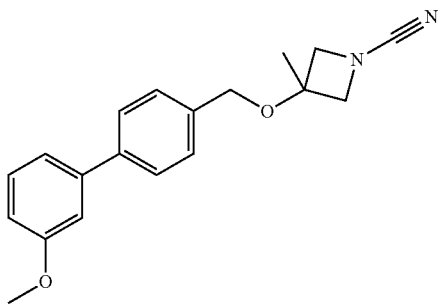 [SMILES: COc1cccc(-c2ccc(COC3(C)CN(C#N)C3)cc2)c1]

Application of similar processes outlined in Method L, and N elaboration of tert-butyl 3-((4-bromobenzyl)oxy)-3-methylazetidine-1-carboxylate afforded the following compounds:

Example 96

3-((3'-Methoxy-[1,1'-biphenyl]-4-yl)methoxy)-3-phenylazetidine-1-carbonitrile: $^1$H NMR (500 MHz, CDCl$_3$) δ ppm 7.58 (d, J=8.5 Hz, 2H) 7.50-7.46 (m, 4H), 7.45-7.42 (m, 1H), 7.37-7.34 (m, 3H), 7.17 (dd, J=7.5, 1.5 Hz, 1H), 7.11 (d, J=1.5 Hz, 1H), 6.91 (dd, J=8.0, 2.5 Hz, 1H), 4.52 (d, J=8.0 Hz, 2H), 4.46 (d, J=8.0 z, 2H), 4.22 (s, 4H), 3.87 (s, 3H).

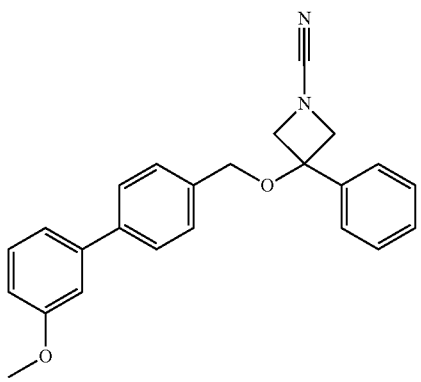 [SMILES: COc1cccc(-c2ccc(COC3(c4ccccc4)CN(C#N)C3)cc2)c1]

Example 97

3-((4-(Benzo[d][1,3]dioxol-5-yl)benzyl)oxy)-3-phenylazetidine-1-carbonitrile: $^1$H NMR (500 MHz, CDCl$_3$) δ ppm 7.51 (d, J=8.0 Hz, 2H) 7.48-7.46 (m, 4H), 7.41 (m, 1H), 7.32 (d, J=8.5 Hz, 2H), 7.06-7.04 (m, 2H), 6.89 (d, J=9.0 Hz, 1H), 6.0 (s, 2H), 4.55 (d, J=8.0 Hz, 2H), 4.46 (d, J=8.0z, 2H), 4.21 (s, 4H).

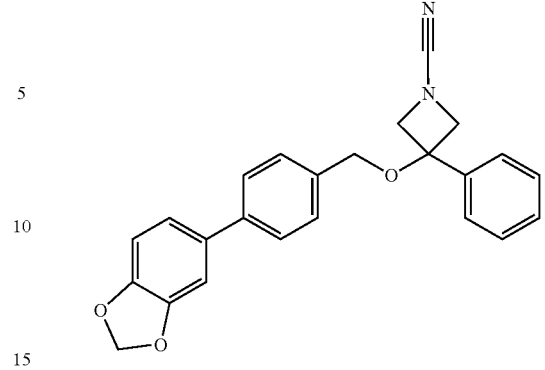

Example 98

3-((4-(2,3-Dihydrobenzo[b][1,4]dioxin-6-yl)benzyl)oxy)-3-phenylazetidine-1-carbonitrile: $^1$H NMR (500 MHz, CDCl$_3$) δ ppm 7.52 (d, J=8.0 Hz, 2H) 7.48-7.44 (m, 4H), 7.41 (m, 1H), 7.32 (d, J=8.0 Hz, 2H), 7.1 (d, J=2.5 Hz, 1H), 7.07 (dd, J=9.0 2.0 Hz, 1H), 6.94 (d, J=9.0 Hz, 1H), 4.52 (d, J=8.0 Hz, 2H), 4.45 (d, J=8.0z, 2H), 4.30 (s, 4H), 4.20 (s, 2H).

Method P.

Benzhydryl-cyanamides 6 were prepared according to Scheme 18. Coupling of 1-benzhydrylazetidin-3-ol with diphenylmethanol under acidic conditions (i.e. p-toluenesulfonic acid) produced azetidine 3. Unmasking of the azetidine with 1-chloroethyl chloroformate and following the processes of Method N afforded benzhydryl-cyanamides 6.

Scheme 18:

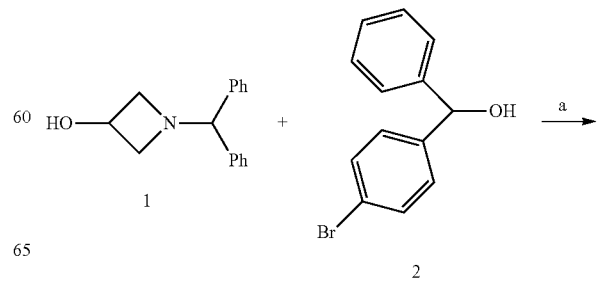

-continued

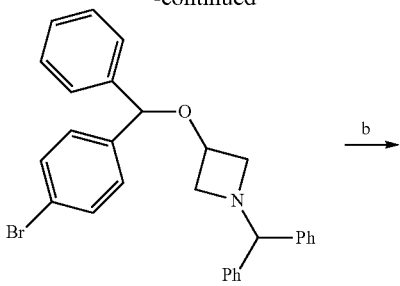

3

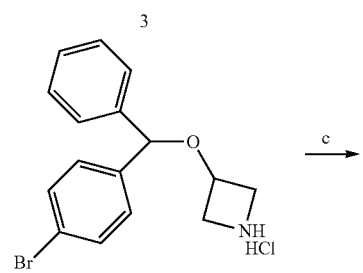

4

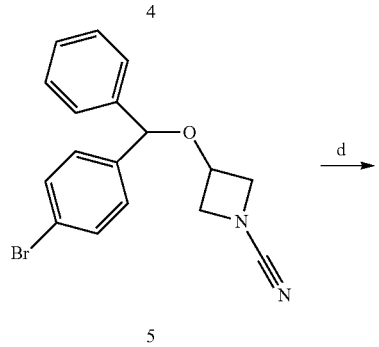

5

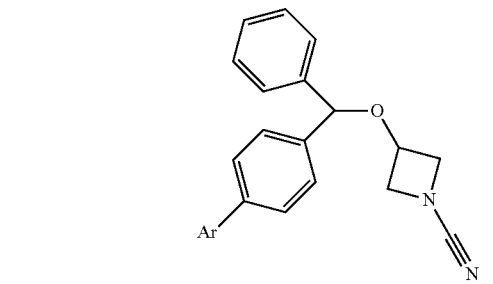

6

Reagents: (a) TsOH, CH₂Cl₂; (b) CH₃CH(Cl)OCOCl, CH₂Cl₂; (c) CNBr, Et₃N, CH₂Cl₂; (d) Ar—B(OH)₂, CsF, Pd(PPh₃)₄, dimethoxyethane The following examples were prepared according to Method P.

Example 99

3-((4-Bromophenyl)(phenyl)methoxy)azetidine-1-carbonitrile. Step a. 1-Benzhydryl-3-((4-bromophenyl)(phenyl)methoxy)azetidine. A mixture of 1-benzhydrylazetidin-3-ol (4.54 g, 19.0 mmol), (4-bromophenyl)(phenyl)methanol (5.9 g, 19.0 mmol), dichloromethane (50 mL) and p-toluenesulfonic acid (6.5 g, 38 mmol) was refluxed for 1 h under continuous removal of water with a Dean-Stark trap. The mixture cooled to room temperature, poured into water and extracted with ethyl acetate. The organic extracts were washed with water and brine and dried over anhydrous MgSO₄. The solvents were removed under vacuum and the residue was purified on silica gel (Biotage; eluting solvents hexanes: EtOAc 10/1 ratio) to afford 1-benzhydryl-3-((4-bromophenyl)(phenyl)methoxy)azetidine as oil (5.1 g, 55.5% yield): $^1$H NMR (500 MHz, CDCl₃) δ ppm 7.41-7.4 (m, 2H), 7.36-7.34 (m, 4H), 7.3-7.24 (m, 2H), 7.26-7.22 (m, 7H), 7.18-7.14 (m, 4H), 5.23 (s, 1H), 4.33 (s, 1H), 4.02-4.17 (m, 1H), 3.44-3.36 (m, 2H), 2.94-2.9 (m, 2H).

Step b. 3-((4-Bromophenyl)(phenyl)methoxy)azetidine hydrochloride. 1-Chloroethyl chloroformate (3.69 g, 25.82 mmol) was added to a cold (0° C.) mixture of 1-benzhydryl-3-((4-bromophenyl)(phenyl)methoxy)azetidine (5.0 g, 10.33 mmol), and dichloromethane (50 mL). The mixture was allowed to come to room temperature and stirred for 20 hours. The volatiles were removed under vacuum and the residue was dissolved in methanol and stirred for 1 hour. The methanol removed under vacuum and the crude product (3.68 g) was used to the next step. Following the processes of Method E, Example 40, steps 5-7 3-((4-bromophenyl)(phenyl)methoxy)azetidine hydrochloride afforded the compounds: $^1$H NMR (500 MHz, CDCl₃) δ ppm 7.45 (d, J=8.5 Hz, 2H), 7.36-7.3 (m, 3H), 7.27-7.25 (m, 2H), 7.18 (d, J=8.5, 2H), 5.25 (s, 1H), 4.42-4.37 (m, 1H), 4.18-4.11 (m, 2H), 4.08-4.03 (m, 2H).

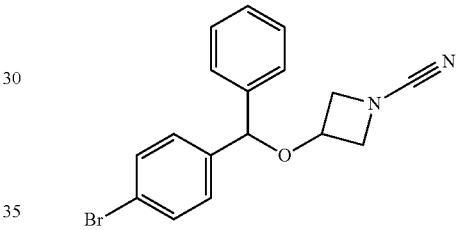

Example 100

3-((3'-Methoxy-[1,1'-biphenyl]-4-yl)(phenyl)methoxy)azetidine-1-carbonitrile: $^1$H NMR (500 MHz, CDCl₃) δ ppm 7.56 (d, J=8.0 Hz, 2H), 7.37-7.33 (m, 8H), 7.15 (dd, J=8.5, 1.0 Hz, 1H), 7.09 (t, J=2 Hz, 1H), 6.09 (dd, J=8.5, 2.5 Hz, 1H), 5.35 (s, 1H), 4.46-4.44 (m, 1H), 4.16-4.14 (m, 2H), 4.11 (m, 2H), 3.86 (s, 3H).

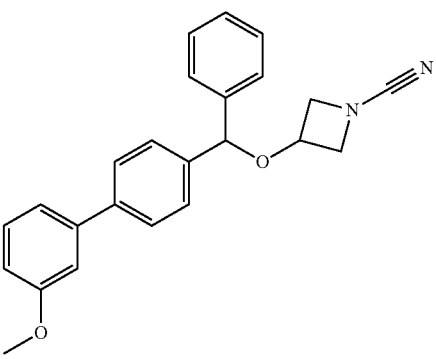 [SMILES: COc1cccc(-c2ccc(C(OC3CN(C#N)C3)c3ccccc3)cc2)c1]

Example 101

3-((4-(3,5-Dimethylisoxazol-4-yl)phenyl)(phenyl)methoxy)azetidine-1-carbonitrile: $^1$H NMR (500 MHz, CDCl₃) δ ppm 7.39-7.33 (m, 7H), 7.23 (d, J=8.0 Hz, 2H), 5.33 (s, 1H), 4.46-4.44 (m, 1H), 4.21-4.16 (m, 2H), 4.1 (m, 2H), 2.39 (s, 3H), 2.26 (s, 3H).

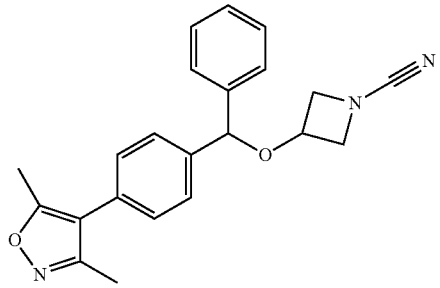 [SMILES: Cc1noc(C)c1-c1ccc(C(OC2CN(C#N)C2)c2ccccc2)cc1]

Example 102

3-((4-(1-Methyl-1H-pyrazol-4-yl)phenyl)(phenyl)methoxy)azetidine-1-carbonitrile: ¹H NMR (500 MHz, CDCl₃) δ ppm 7.73 (s, 1H), 7.59 (s, 1H), 7.43 (d, J=8.0 Hz, 2H) 7.34-7.26 (m, 7H), 5.3 (s, 1H), 4.44-4.42 (m, 1H), 4.14-4.1 (m, 4H), 3.94 (s, 3H).

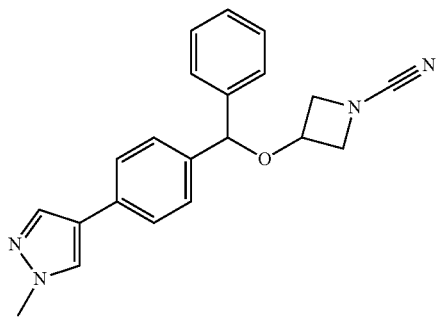 [SMILES: Cn1cc(-c2ccc(C(OC3CN(C#N)C3)c3ccccc3)cc2)cn1]

Method Q.

N-linked cyanamides 5 were prepared according to Scheme 19. Reductive amination of 3-oxoazetidine 1 with amines 2 using sodiumtriacetoxy borohydride under acidic conditions (i.e. AcOH) produced amines 3. Applications of the processes of Method N afforded N-linked cyanamides 5.

Scheme 19:

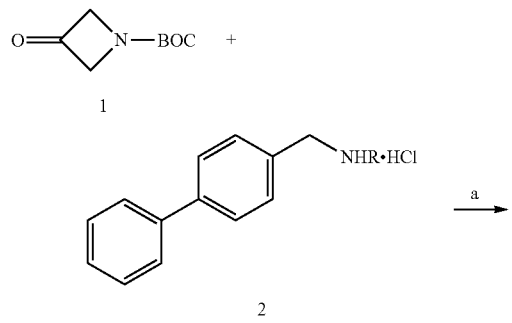

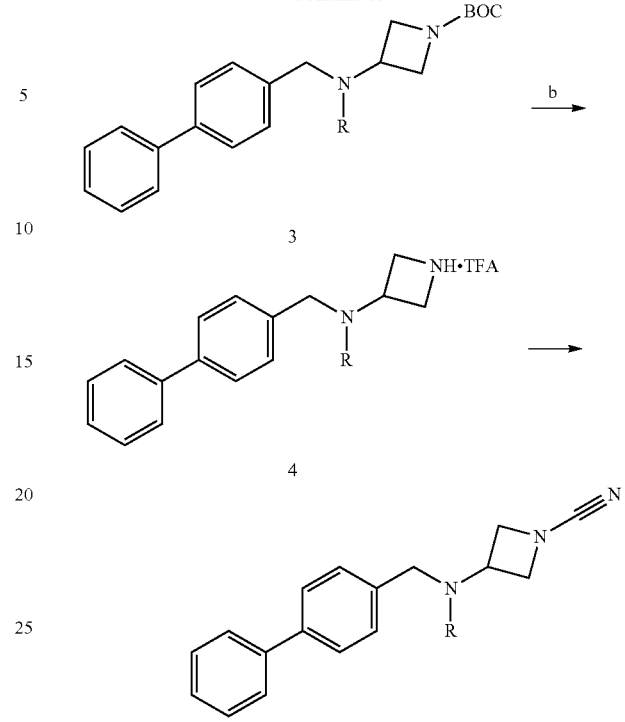

Reagents: (a) Na(OAc)₃BH, AcOH, THF; (b) TFA, CH₂Cl₂; (d) CNBr, Et₃N, CH₂Cl₂

The following examples were prepared according to Method Q.

Example 103

3-(([1,1'-Biphenyl]-4-ylmethyl)(methyl)amino)azetidine-1-carbonitrile. Step a. tert-Butyl 3-(([1,1'-biphenyl]-4-ylmethyl)(methyl)amino)azetidine-1-carboxylate. Into a mixture of 1-([1,1'-biphenyl]-4-yl)-N-methylmethanamine hydrochloride (254 mg, 1.09 mmol), tert-butyl 3-oxoazetidine-1-carboxylate (169.6 mg, 0.99 mmol), acetic acid (0.17 mL) and anhydrous tetrahydrofuran (3 mL), was added sodiumtriacetoxy borohydride (292 mg, 1.39 mmol). The mixture was stirred for 5 hours and then was quenched with saturated aqueous sodium bicarbonate. The mixture was extracted with ethyl acetate, washed with brine and dried over anhydrous MgSO4. The solvents were removed under vacuum and the residue was purified on silica gel (Biotage; eluting solvents hexanes: EtOAc 2/1 ratio) to afford tert-butyl 3-(([1,1'-biphenyl]-4-ylmethyl)(methyl)amino)azetidine-1-carboxylate as oil (326 mg, 84.9% yield): ¹H NMR (500 MHz, CDCl₃) δ ppm 7.59 (d, J=7.5 Hz, 2H), 7.56 (d, J=7.5 Hz, 2H), 7.4 (m, 2H), 7.36-7.34 (m, 3H), 3.97-3.94 (m, 2H), 3.88-3.85 (m, 2H), 3.43 (s, 2), 3.3-3.26 (m, 1H), 2.1 (s, 3H), 1.45 (s, 9H).

Following the processes of Method L, tert-Butyl 3-(([1,1'-biphenyl]-4-ylmethyl)(methyl)amino)azetidine-1-carboxylate afforded 3-(([1,1'-biphenyl]-4-ylmethyl)(methyl)amino)azetidine-1-carbonitrile.

3-(([1,1'-Biphenyl]-4-ylmethyl)(methyl)amino)azetidine-1-carbonitrile: ¹H NMR (500 MHz, CDCl₃) δ ppm 7.6-7.58 (m, 2H), 7.56 (d, J=8.0, 2H), 7.46 (t, J=8.0 Hz, 2H), 7.36-7.33 (m, 3H), 4.13-4.08 (m, 4H), 3.49 (m, 1H), 3.43 (s, 2H), 2.13 (s, 3H).

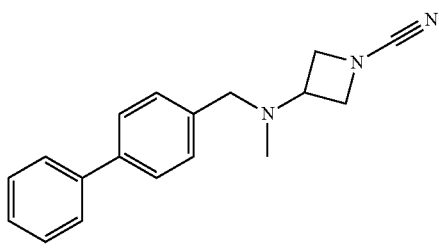 [SMILES: CN(Cc1ccc(-c2ccccc2)cc1)C1CN(C#N)C1]

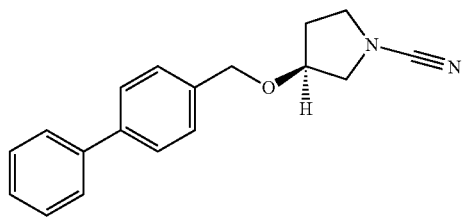 [SMILES: N#CN1CC[C@H](OCc2ccc(-c3ccccc3)cc2)C1]

Method R.

The preparation of pyrrolidine-1-carbonitriles 3 and 6 were prepared according to Scheme 20. (R)-Pyrrolidin-3-ol treatment with cyanogen bromide and trimethylamine afforded nitrile 2, which upon alkylation with aryl-alkyl halides produced pyrrolidine-1-carbonitrile 3. (S)-Pyrrolidin-3-ol produced pyrrolidine-1-carbonitrile 6.

Scheme 20:

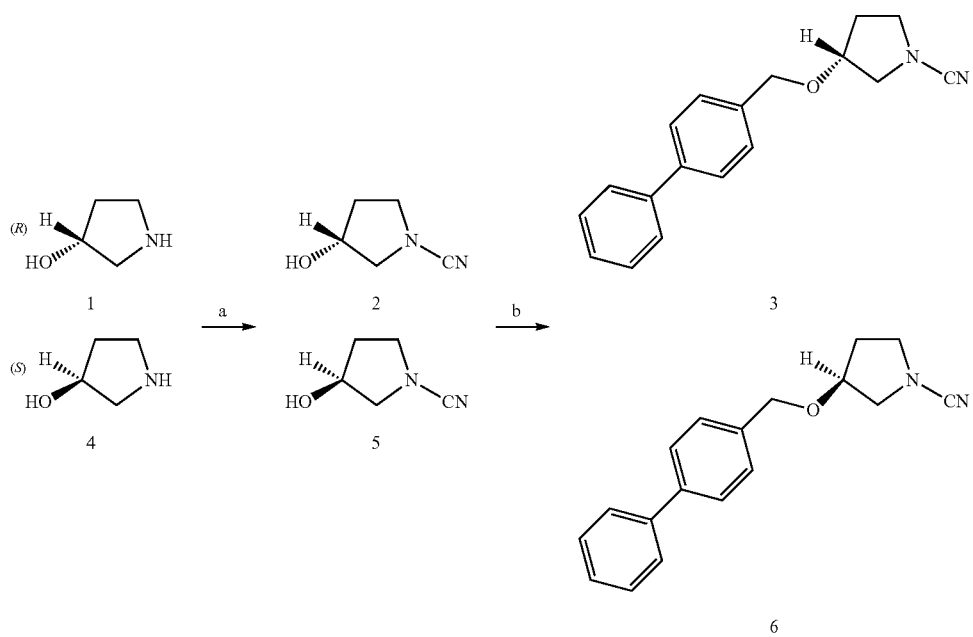

Reagents: (a) BrCN, Et₃N; (b) 4-Ph benzyl chloride NaH, DMF

The following examples were prepared according to Method R.

Example 104

(S)-3-([1,1'-Biphenyl]-4-ylmethoxy)pyrrolidine-1-carbonitrile: $^1$H NMR (500 MHz, CDCl$_3$) δ ppm 7.62-7.6 (m, 4H), 7.49 (t, J=8.0 Hz, 2H), 7.43 (d, J=8.0 Hz, 2H), 7.39 (dt, J=7.5, 1.5 Hz, 1H), 4.58 (s, 2H), 4.24-4.22 (m, 1H), 3.68-3.6 (m, 1H), 3.55-3.52 (m, 3H), 2.18-2.13 (m, 1H), 2.03-1.96 (m, 1H).

Example 105

(R)-3-([1,1'-Biphenyl]-4-ylmethoxy)pyrrolidine-1-carbonitrile: $^1$H NMR (500 MHz, CDCl$_3$) δ ppm 7.62-7.6 (m, 4H), 7.49 (t, J=8.0 Hz, 2H), 7.43 (d, J=8.0 Hz, 2H), 7.39 (dt, J=7.5, 1.5 Hz, 1H), 4.58 (s, 2H), 4.24-4.22 (m, 1H), 3.68-3.6 (m, 1H), 3.55-3.52 (m, 3H), 2.18-2.13 (m, 1H), 2.03-1.96 (m, 1H).

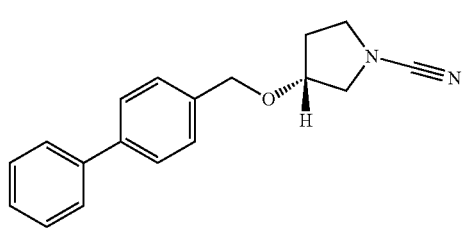 [SMILES: N#CN1CC[C@@H](OCc2ccc(-c3ccccc3)cc2)C1]

Method S.

The preparation of piperidine-1-carbonitrile 4 was prepared according to Scheme 21. The preparation followed the processes of Method N.

Scheme 21:

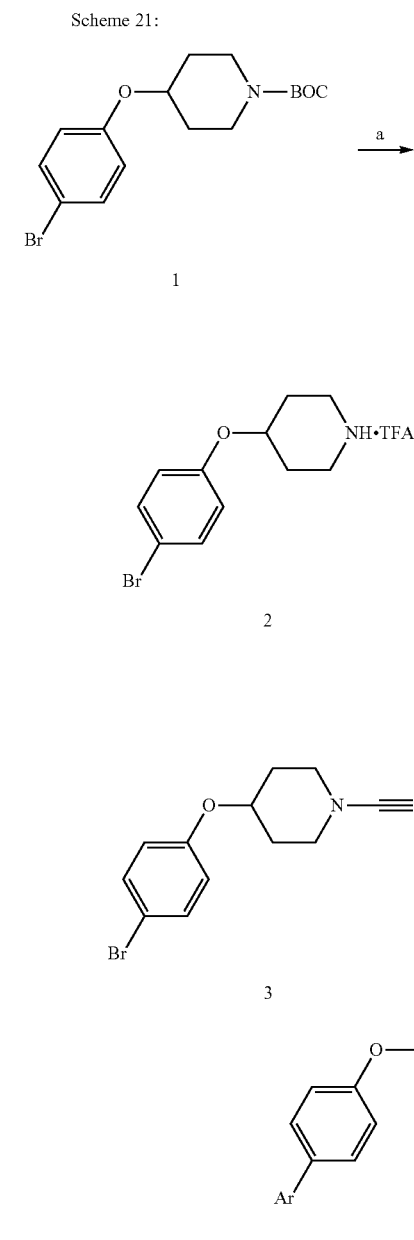

Reagents: (a) TFA, CH₂Cl₂; (b) CNBr, Et₃N, CH₂Cl₂; (c) Ar—B(OH)₂, CsF₃, Pd(PPh₃)₄, dimethoxyethane The following example was prepared according to Method S.

Example 106

4-(4-Bromophenoxy)piperidine-1-carbonitrile: ¹H NMR (500 MHz, CDCl₃) δ ppm 7.39 (d, J=8.5 Hz, 1H), 6.79 (d, J=8.5 Hz, 1H), 4.49-4.46 (m, 1H), 3.51-3.45 (m, 2H), 3.22-3.17 (m, 2H), 2.04-1.98 (m, 2H), 1.94-1.90 (m, 2H).

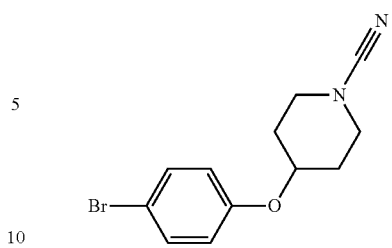

Method T.

The preparation of cyclobutane carbonitriles 4 and 5 were prepared according to Scheme 22. 3-Methylenecyclobutane-1-carbonitrile 1 was oxidized with NaIO₄/RuCl₃ to afford cyclobutanone 2, which upon reduction with NaBH₄ and alkylation with aryl-alkyl halides afforded carbonitriles 4 and 5.

Scheme 22:

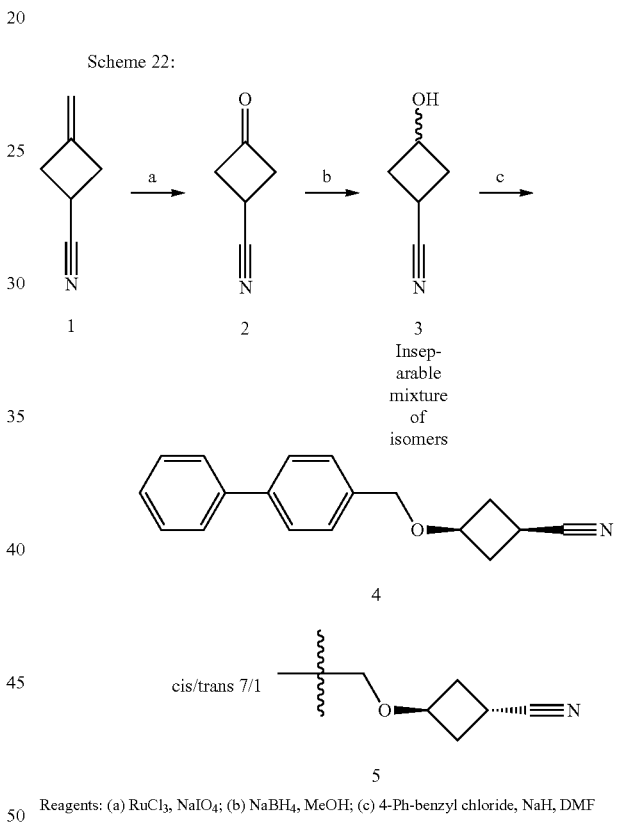

Reagents: (a) RuCl₃, NaIO₄; (b) NaBH₄, MeOH; (c) 4-Ph-benzyl chloride, NaH, DMF

The following examples were prepared according to Method T.

Example 107

(1R,3R)-3-([1,1'-Biphenyl]-4-ylmethoxy)cyclobutane-1-carbonitrile. Step 1. 3-Oxocyclobutane-1-carbonitrile. Sodium periodate (9.2 g, 42.96 mmol) was added to a mixture of 3-methylenecyclobutane-1-carbonitrile (1.0 g, 10.74 mmol), ruthenium (III) chloride hydrate (50 mg, 0.24 mmol) CH₃CN (20 mL), CH₂Cl₂ (20 mL) and water (20 mL). The mixture was stirred for 8 hours and then diluted with water (100 mL) and extracted with CH₂Cl₂ (2×). The organics were dried over anhydrous MgSO₄. The solvents were removed under vacuum and the residue was purified on silica gel (Biotage; eluting solvents hexanes: EtOAc 3/1 ratio) to afford 3-oxocyclobutane-1-carbonitrile as oil (326 mg, 99% yield): $^1$H NMR (500 MHz, CDCl$_3$) δ ppm 3.57-3.55 (m, 4H), 3.3-3.24 (m, 1H).

Step 2. 3-Hydroxycyclobutane-1-carbonitrile. Sodium borohydride (597 mg, 15.8 mmol) was added in portions into a cold (0° C.) mixture of 3-oxocyclobutane-1-carbonitrile (1.0 g, 10.52 mmol) and anhydrous methanol (10 mL). After the addition the mixture stirred for 30 minutes, and then it was carefully poured into ice water. The mixture was extracted with ethyl acetate and the organic extracts washed with water and brine and dried over anhydrous MsSO$_4$. The solvents were removed under vacuum and the residue was purified on silica gel (Biotage; eluting solvents hexanes: EtOAc 2/1 ratio) to afford 3-hydroxycyclobutane-1-carbonitrile, 8:1 isomeric mixture, as oil (920 mg, 92% yield): $^1$H NMR (500 MHz, CDCl$_3$) δ ppm [4.62 (m), 4.26 (m), 1H], [3.06 (m), 2.75 (m), 2H], [5.65 (m), 2.33 (m), 2H], 2.6 (m, 1), 2.31 (m, 1H).

Step 3. (1R,3R)-3-([1,1'-Biphenyl]-4-ylmethoxy)cyclobutane-1-carbonitrile. Sodium hydride (60% dispersion in mineral oil; 107.1 mg, 2.68 mmol) was added into a cold (0° C.) mixture of 3-hydroxycyclobutane-1-carbonitrile (200 mg, 2.06 mmol) and anhydrous DMF (5 mL). After stirring for 1 hour, 4-(chloromethyl)-1,1'-biphenyl (501.5 mg, 2.47 mmol) was added and the mixture was allowed to come to room temperature and stirred for 8 hours. Then, the mixture was poured into saturated aqueous ammonium chloride and extracted with ethyl acetate (3×). The organic extracts were dried over anhydrous MgSO$_4$. The solvents were removed under vacuum and the residue was purified on silica gel (Biotage; eluting solvents hexanes: EtOAc 2/1 ratio) to afford (1R,3R)-3-([1,1'-biphenyl]-4-ylmethoxy)cyclobutane-1-carbonitrile as oil, $^1$H NMR (500 MHz, CDCl$_3$) δ ppm 7.59-7.57 (m, 4H), 7.46-7.42 (m, 2H), 7.39 (d, J=8.5 Hz, 2H), 7.37-7.34 (m, 1H), 4.46 (s, 2H), 4.04-4.0 (m, 1H), 2.71-2.61 (m, 3H), 2.43-2.38 (m, 2H).

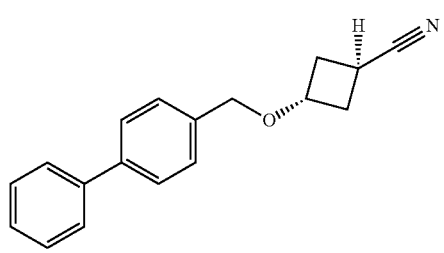 [SMILES: N#C[C@H]1C[C@H](OCc2ccc(-c3ccccc3)cc2)C1]

Example 108

(1S,3S)-3-([1,1'-biphenyl]-4-ylmethoxy)cyclobutane-1-carbonitrile: $^1$H NMR (500 MHz, CDCl$_3$) δ ppm 7.59-7.57 (m, 4H), 7.46-7.42 (m, 2H), 7.39 (d, J=8.5 Hz, 2H), 7.37-7.34 (m, 1H), 4.49 (s, 2H), 4.41-4.39 (m, 1H), 3.11-3.06 (m, 1H), 2.65-2.61 (m, 2H), 2.48-2.42 (m, 2H).

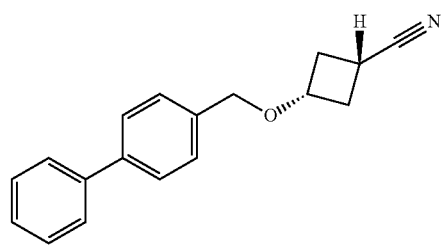 [SMILES: N#C[C@H]1C[C@@H](OCc2ccc(-c3ccccc3)cc2)C1]

Method U.

The preparation of azetidine-acetonitrile 4 was prepared according to Scheme 23. Amine 3 was prepared according to processes of Method N. The azetidine-acetonitrile 4 was prepared from 3 upon treatment with 2-hydroxyacetonitrile and trimethylamine

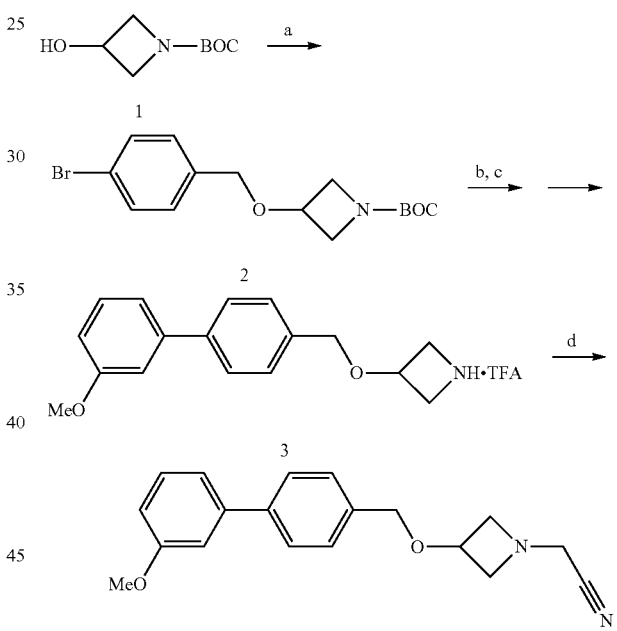

Reagents: (a) 4-Br-benzyl bromide, NaH, DMF; (b) Ar—B(OH)$_2$, K$_2$CO$_3$, Pd(PPh$_3$)$_4$, dioxane, H$_2$O; (c) TFA, CH$_2$Cl$_2$; (d) HOCH$_2$CN, Et$_3$N The following example was prepared according to Method U.

Example 109

2-(3-((3'-Methoxy-[1,1'-biphenyl]-4-yl)methoxy)azetidin-1-yl)acetonitrile: $^1$H NMR (500 MHz, CDCl$_3$) δ ppm 7.58 (d, J=8.5 Hz, 2H), 7.41 (d, J=8.5, 2H), 7.35 (t, J=7.5 Hz, 1H), 7.18 (d, J=8.5 H, 1H), 7.11 (t, J=3.0 Hz, 1H), 6.91 (dd, J=8.5, 2.5 Hz, 1H), 4.49 (s, 2H), 4.26-4.23 (m, 1H), 3.86 (s, 3H), 3.64-3.61 (m, 2H), 3.48 (s, 2H), 3.3-3.27 (m, 2H).

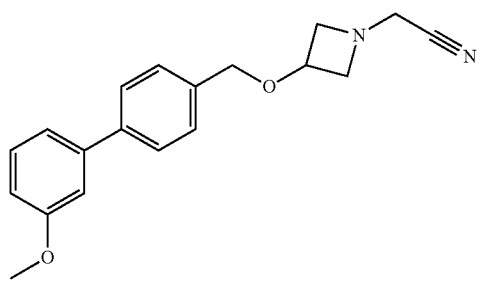 [SMILES: COc1cccc(-c2ccc(COC3CN(CC#N)C3)cc2)c1]

Method V.

The pyridine nitriles 4 and 5 were prepared according to Scheme 24 by coupling 5-hydroxypicolinonitrile with benzyl halides 2 and 3 in the presence of base, potassium carbonate, in a polar solvent, as N,N-dimethylformamide. The fluorinated analogs 7 and 8 were prepared from 3,5-difluoropicolinonitrile 6 upon reaction with [1,1'-biphenyl]-4-ylmethanol in the presence of a base, as sodium hydride, in a polar solvent, as N,N-dimethylformamide.

Scheme 24:

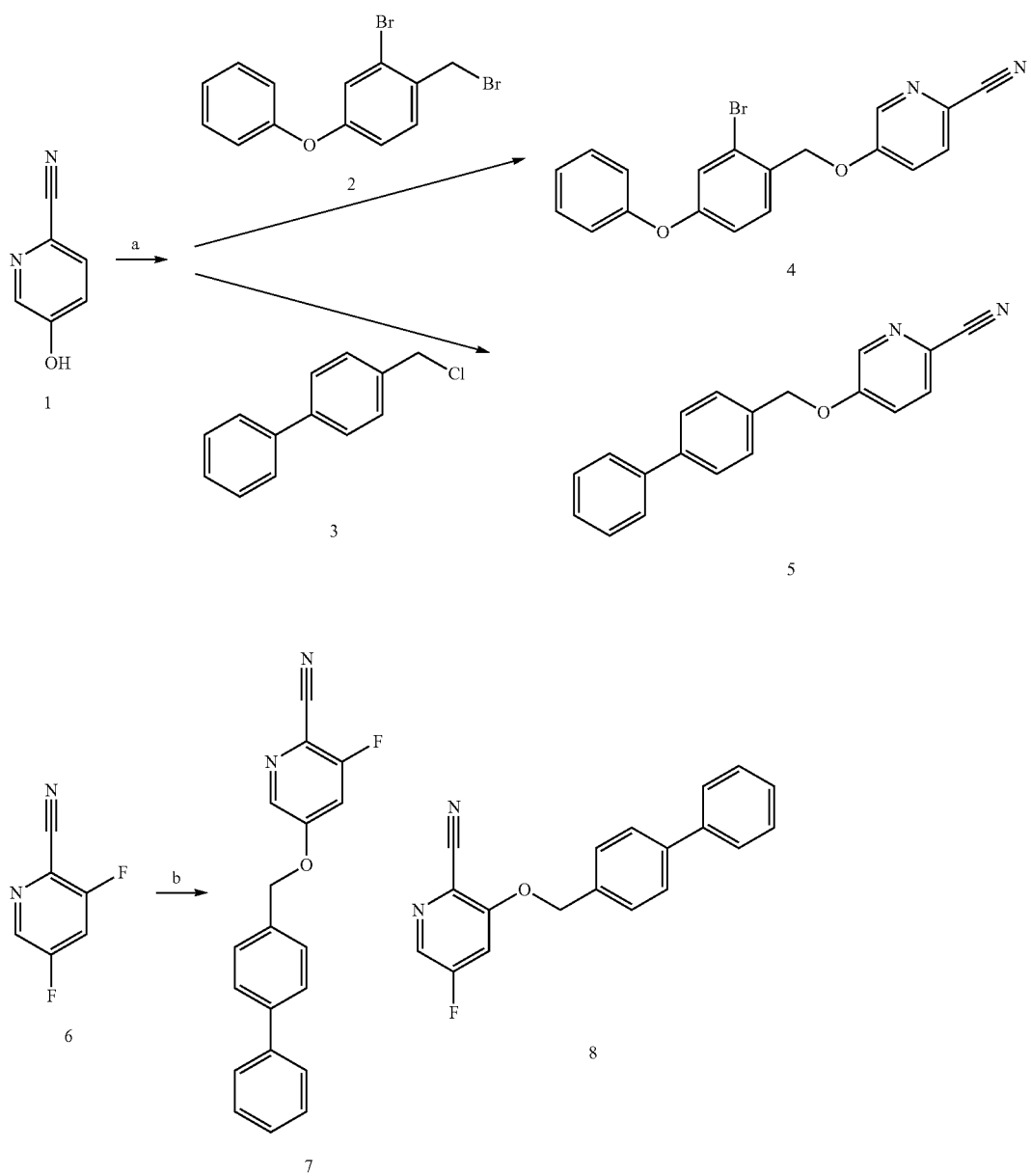

Reagents: (a) K$_2$CO$_3$, DMF; (b) NaH, DMF

The following examples were prepared according to Method V.

Example 110

5-((2-Bromo-4-phenoxybenzyl)oxy)picolinonitrile. Potassium carbonate (516 mg, 3.74 mmol) was added into mixture of 5-hydroxypicolinonitrile (224.8 mg, 1.87 mmol) and anhydrous DMF (5 mL). After stirring for 1 hour, 2-bromo-1-(bromomethyl)-4-phenoxybenzene (640 mg, 1.87 mmol) was added and the mixture was stirred at 60° C. for 1 hour and was filtered. The filtrate was taken in water (100 mL) and extracted with EtOAc. The organic extracts were dried over anhydrous MgSO$_4$. The solvents were removed under vacuum and the residue was purified on silica gel (Biotage; eluting solvents hexanes: EtOAc 3/1 ratio) to afford 5-((2-bromo-4-phenoxybenzyl)oxy)picolinonitrile as oil (570 mg, 80% yield). $^1$H NMR (500 MHz, CDCl$_3$) δ ppm $^1$H NMR (500 MHz, CDCl$_3$) δ ppm 8.46 (d, J=2.5 Hz, 1H), 7.67 (d, J=8.5 Hz, 1H), 7.42-7.37 (m, 3H), 7.32 (dd, J=9.0, 3.0 Hz, 1H), 7.24 (d, J=2.5 Hz, 1H), 7.19 (t, J=7.5 Hz, 1H), 7.05 (dd, J=8.5, 1.5 Hz, 2H), 6.99 (dd, J=8.5, 2.5 Hz, 1H), 5.2 (s, 2H).

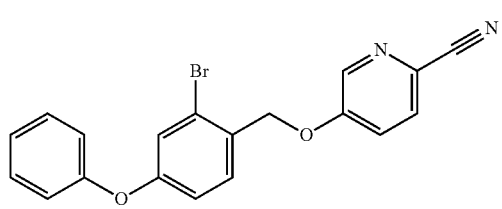 [SMILES: N#Cc1ccc(OCc2ccc(Oc3ccccc3)cc2Br)cn1]

Example 111

5-([1,1'-Biphenyl]-4-ylmethoxy)picolinonitrile: $^1$H NMR (500 MHz, CDCl$_3$) δ ppm 8.47 (d, J=3.0 Hz, 1H), 7.66-7.63 (m, 3H), 7.6-7.58 (m, 2H), 7.49-7.44 (m, 4H), 7.39-7.37 (m, 1H), 7.33 (dd, J=9.0, 3.0H, 1 Hz), 5.02 (s, 2H).

Example 112

5-([1,1'-Biphenyl]-4-ylmethoxy)-3-fluoropicolinonitrile: $^1$H NMR (500 MHz, CDCl$_3$) δ ppm 8.35 (d, J=2.44 Hz, 1H), 7.69-7.67 (m, 2H), 7.63-7.62 (m, 2H), 7.52-7.47 (m, 4H), 7.42 (t, J=6.8 Hz, 1H), 7.16 (dd, 7.4, 2.4 Hz, 1H), 5.25 s (2H).

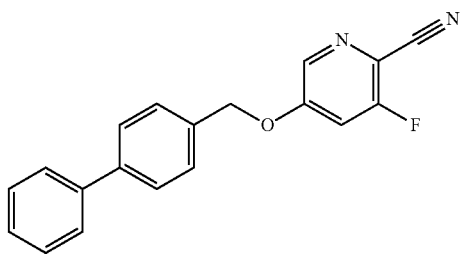 [SMILES: N#Cc1ncc(OCc2ccc(-c3ccccc3)cc2)cc1F]

Example 113

3-([1,1'-Biphenyl]-4-ylmethoxy)-5-fluoropicolinonitrile: $^1$H NMR (500 MHz, CDCl$_3$) δ ppm 8.21 (d, J=2.44 Hz, 1H), 7.68-7.67 (m, 2H), 7.63-7.61 (m, 2H), 7.55 (d, J=10.0 Hz, 2H), 7.49 (m, 2H), 7.42 (tt, J=6.8, 1.5, 1H), 7.18 (dd, 7.4, 2.4 Hz, 1H), 5.32 s (2H).

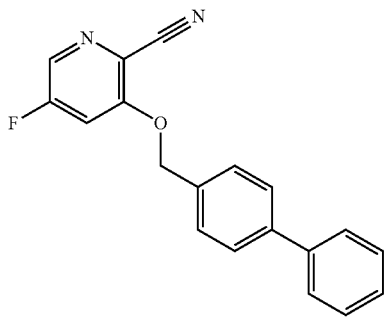 [SMILES: N#Cc1ncc(F)cc1OCc1ccc(-c2ccccc2)cc1]

Method W.

The pyridine-nitrile 3b was prepared according to Scheme 25. Alcohol 1 was coupled with carboxylic acid 2 using EDCI/DMAP as the coupling agent to yield 3a, which upon treatment with CuCN under microwave conditions afforded nitrile 3b.

Scheme 25:

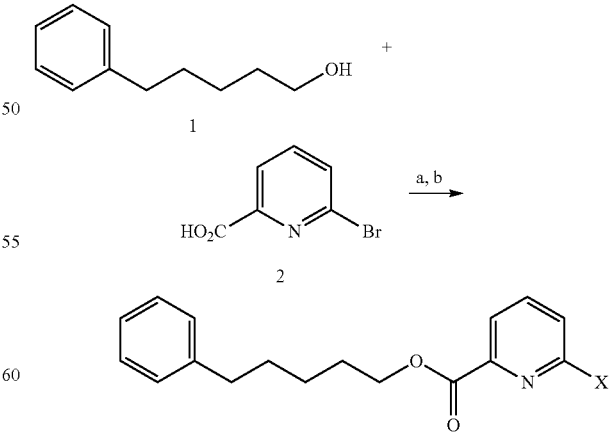

3a X = Cl
3b X = CN

Reagents: (a) DMAP, EDCl, DMF, rt (b) CuCN, DMF, 150° C. microwave, 30 mins

The following example was prepared according to Method W.

Example 114

Step 1. 5-phenylpentyl 6-bromopicolinate. To a stirring solution of 6-bromo picolinic acid (222 mg, 1.1 mmol) and 5-phenylpentanol (164 mg, 1.0 mmol) in DMF (5 mL) at 0° C. was added DMAP (391 mg, 3.2 mmol) then EDCI (481 mg, 3.1 mmol) and the reaction mixture was stirred at rt for 10 h. The reaction mixture was quenched with water (50 mL), extracted with 50% Et$_2$O/Hexanes (3×50 mL), washed with water (25 mL), brine (25 mL) then dried over sodium sulfate, filtered and concentrated. The crude residue was further purified by silica gel chromatography using 25% EtOAc/Hexanes as eluent to afford 5-phenylpentyl 6-bromopicolinate as a clear colorless oil (31 mg, 89%): $^1$H NMR (500 MHz, CDCl$_3$) δ ppm 8.02-8.05 (m, 1H), 7.65-7.71 (m, 2H), 7.25-7.30 (m, 2H), 7.15-7.20 (m, 3H), 4.39 (t, J=6.8 Hz, 2H), 2.64 (t, J=7.8 Hz, 2H), 1.84 (quin, J=7.8 Hz, 2H), 1.69 (quin, J=7.3 Hz, 2H), 1.47 (quin, J=8.3 Hz, 2H).

Step 2. 5-phenylpentyl 6-cyanopicolinate. A solution of 5-phenylpentyl 6-bromopicolinate (300 mg, 0.86 mmol), CuCN (154 mg, 1.72 mmol) in DMF (3.4 mL) was heated at 150° C. in a microwave for 30 mins. The crude reaction mixture was cooled to rt, then diluted with water (50 mL) and extracted with 50% Et$_2$O/Hexanes (3×50 mL), washed with water (25 mL), brine (25 mL). The combined organic extracts were dried over sodium sulfate, filtered and concentrated and the crude residue was further purified by silica gel chromatography using 25% EtOAc/Hexanes eluent to give 5-phenylpentyl 6-cyanopicolinate as a white solid (140 mg, 55%): $^1$H NMR (500 MHz, CDCl$_3$) δ ppm 8.28 (dd, J=1.0, 7.8 Hz, 1H), 8.01 (app t, J=7.8 Hz, 1H), 7.87 (dd, J=1.0, 7.3 Hz, 1H), 7.25-7.30 (m, 2H), 7.12-7.20 (m, 3H), 4.43 (t, J=6.8 Hz, 2H), 2.65 (t, J=7.8 Hz, 2H), 1.86 (quin, J=6.8 Hz, 2H), 1.71 (quin, J=7.7 Hz, 2H), 1.49 (quin, J=7.8 Hz, 2H).

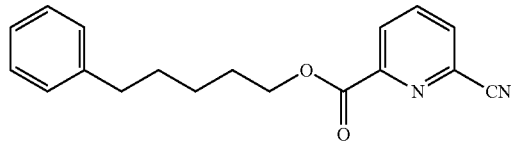 [SMILES: N#Cc1cccc(C(=O)OCCCCCc2ccccc2)n1]

Method X.

Pyrimidine-nitrile 3b was prepared according to Scheme 26. Alcohol 1 was coupled with pyrimidine 2 using the Mitsunobu protocol (DIEA/PPh$_3$/DIAD) to afford ester 3a, which was treated with Zn(CN)$_2$ under microwave conditions to afford nitrile 3b.

Scheme 26:

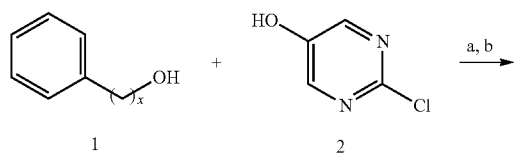

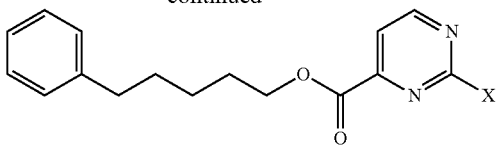

3a X = Cl
3b X = CN

Reagents: (a) DIEA, PPh$_3$, DIAD, THF, 0° C. (b) Zn(CN)$_2$, Pd(PPh$_3$)$_4$, 160° C. microwave, 1h The following examples were prepared according to Method W.

Example 115

Step 1. 2-chloro-5-((6-phenylhexyl)oxy)pyrimidine. To a stirring solution of chlorohydroxypyrimidine (250 mg, 1.92 mmol), 6-phenylhexanol (444 mg, 2.5 mmol), in THF (5 mL) was added DIEA (1.0 mL, 5.76 mmol), PPh$_3$ (1.0 g, 3.84 mmol) and the mixture was cooled to 0° C. and DIAD (0.756 mL, 3.84 mmol) was added dropwise. The mixture was allowed to warm to rt and stirred for 24 h. The crude reaction mixture was concentrated, and purified by silica gel chromatography using 0-10% EtOAc/hexanes to afford 2-chloro-5-((6-phenylhexyl)oxy)pyrimidine as a white solid (400 mg, 72%): $^1$H NMR (500 MHz, CDCl$_3$) δ ppm 8.26 (s, 2H), 7.15-7.30 (m, 5H), 4.03 (t, J=6.3 Hz, 2H), 2.63 (t, J=7.8 Hz, 2H), 1.81 (quin, J=8.3 Hz, 2H), 1.66 (quin, J=7.7 Hz, 2H), 1.49 (quin, J=7.8 Hz, 2H), 1.40 (J=7.8 Hz, 2H).

Step 2. 5-((6-phenylhexyl)oxy)pyrimidine-2-carbonitrile. A solution of 2-chloro-5-((6-phenylhexyl)oxy)pyrimidine (200 mg, 0.69 mmol) in DMF (5 mL) was purged with argon for 10 mins., then Zn(CN)$_2$ (122 mg, 1.04 mmol), and Pd(PPh$_3$)$_4$ (40 mg, 0.035 mmol) was added and the mixture heated in a microwave at 160° C. for 1 h. The reaction mixture was cooled to rt, then diluted with water (50 mL), extracted with 50% EtOAc/hexanes (3×50 mL), the combined organic phase was washed with water (25 mL), brine (25 mL), dried over sodium sulfate, filtered and concentrated. The crude residue was further purified by silica gel chromatography using 5-25% EtOAC/hexanes to afford 5-((6-phenylhexyl)oxy)pyrimidine-2-carbonitrile as a white solid (40 mg, 21%): $^1$H NMR (500 MHz, CDCl$_3$) δ ppm 8.42 (s, 2H), 7.15-7.31 (m, 5H), 4.12 (t, J=6.3 Hz, 2H), 2.63 (t, J=7.8 Hz, 2H), 1.85 (quin, J=6.8 Hz, 2H), 1.67 (quin, J=7.8 Hz, 2H), 1351 (quin, J=7.3 Hz, 2H), 1.41 (quin, J=7.8 Hz, 2H).

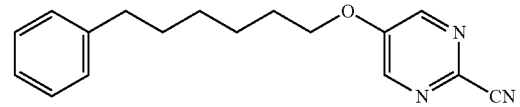 [SMILES: N#Cc1ncc(OCCCCCCc2ccccc2)cn1]

Example 116

5-((5-phenylpentyl)oxy)pyrimidine-2-carbonitrile: $^1$H NMR (500 MHz, CDCl$_3$) δ ppm 8.41 (s, 2H), 7.14-7.31 (m, 5H), 4.13 (t, J=6.2 Hz, 2H), 2.65 (t, J=7.7 Hz, 2H), 1.88 (quin, J=7.3 Hz, 2H), 1.71 (quin, J=7.5 Hz, 2H), 1.52 (quin, J=8.1 Hz, 2H).

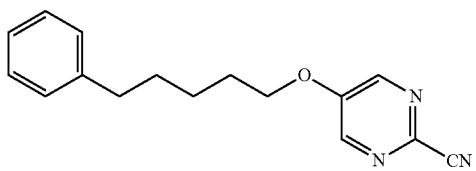 [SMILES: N#Cc1ncc(OCCCCCc2ccccc2)cn1]

Example 117

5-(2-(2-(benzyloxy)ethoxy)ethoxy)pyrimidine-2-carbonitrile: $^1$H NMR (500 MHz, CDCl$_3$) δ ppm 8.49 (s, 2H), 7.27-7.37 (m, 5H), 4.55 (s, 2H), 4.33 (t, J=4.4 Hz, 2H), 3.92 (t, J=4.4 Hz, 2H), 3.73 (t, J=4.4 Hz, 2H), 3.64 (t, J=4.9 Hz, 2H).

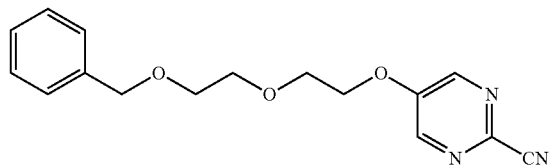 [SMILES: N#Cc1ncc(OCCOCCOCc2ccccc2)cn1]

Example 118 hNAAA overexpression and purification. The disclosure includes hNAAA constructs we prepared for expression, purification, protein characterization, and assay development to screen and identify potent and selective inhibitors. These different constructs and cell lines are shown in Table 1. The hNAAA cDNA was first cloned into the pcDNA 3.1/myc-His vector and a stable HEK293 (293WT) polyclonal cell line was created and propagated in DMEM supplemented with 10% FBS media. Prior to hNAAA secretion stimulation by ammonium chloride (NH$_4$Cl) the cells were grown to ~90% of confluency in the media DMEM/ 10% FBS. The secretion stimulation was then initiated by exchanging to DMEM serum-free media with NH$_4$Cl added (10 mM final concentration). Media containing secreted proteins was collected after 48 hours and NH$_4$Cl stimulated hNAAA secretion from the cells was repeated with fresh media another two times. Combined media with secreted enzyme was concentrated by protein precipitation with ammonium sulfate added to 60% saturation, and hNAAA containing a C-terminal myc and hexa-histidine tag (NAAA-MH) was purified by IMAC chromatography. The purified protein (~1 mg/liter cell culture media) used for assays was dialyzed into 80 mM Na-phosphate buffer (pH 6.7) containing 200 mM NaCl and 0.5 mM dithiothreitol (DTT), with three changes, and stored at −80° C. in 8 μg aliquots, sufficient to perform a fluorescence-based assay in one 96 well plate. For NMR experiments, the purified protein was dialyzed into 80 mM Na-phosphate buffer (pH 4.8) containing 200 mM NaCl and 0.5 mM dithiothreitol (DTT), with three changes, sterile filtered, concentrated to 5-10 mg/ml, and stored at 4° C. before use.

To increase the hNAAA yield using the same pcDNA3.1-hNAAA/myc-His construct we created stably transfected 293WT and 293F monoclonal cell lines. 293F cells offer two advantages over 293WT: a faster doubling time, and the ability to grow in suspension in chemically defined (CD) media that contains no added proteins. Both monoclonal cell lines were created by serial dilution of a freshly transfected polyclonal cell line, where colonies arising from individual cells were tested and selected for maximum enzyme specific activity from the lysed cells and from enzyme secreted into the serum-free media containing NH$_4$Cl. Both monoclonal cell lines effectively doubled the yield of hexa-histidine tagged purified protein obtained (2 mg/liter cell culture media) over the polyclonal cell line. We recently created a new 293F cell lines expressing hNAAA without tags (hNAAA-WT) at a level up to 5 mg per liter culture media (before purification, estimated based on activity). However, preliminary experiments with hNAAA-WT suggest it is considerably more difficult and laborious to purify than the hexa-histidine tagged protein. In addition, dynamic light scattering experiments suggest that >95% IMAC purified hNAAA-MH is monomeric heterodimer with a small amount of aggregate, whereas the multi-step purified hNAAA-WT contains much more aggregated protein. Therefore a construct expressing hNAAA only with C-terminal histidine tag (hNAAA-H; 20 amino acids including myc epitope tag was truncated in hNAAA-MH) is currently in preparation for generation of stably transfected 293F monoclonal cell lines. We believe the hNAAA-H engineered protein will have the advantages in ease of purification of hNAAA-MH, yet ostensibly be more amenable to crystallization than the hNAAA-MH protein because of the shorter tag, and that the small amount of aggregate may be removed via a gel-filtration chromatography step following the IMAC purification and/or be ameliorated by exploring different buffer conditions and additives to the purified protein.

TABLE 1

Human NAAA/HEK293 stable cell lines created for enzyme assay screening and structural biology experiments.

| Enzyme Construct | Vector | Cell Line | Monoclonal (M) or Polyclonal (P) | Protein Secreted per Liter Culture Media | Protein Purified per Liter Culture Media |
|---|---|---|---|---|---|
| NAAA-MH[1] | pcDNA 3.1/myc-His | 293WT | P | 1.5 | 1 |
| NAAA-MH[1] | pcDNA 3.1/myc-His | 293WT | M | 3 | 2 |
| NAAA-MH[1] | pcDNA 3.1/myc-His | 293F | M | 3 | 2 |
| Wild-type NAAA | pcDNA 3.1 | 293F | P | 5 | ~1 |
| NAAA-H[2] | pcDNA 3.1/myc-His | 293F | P | TBD[3] | TBD[3] |

[1]Wild-type NAAA with C-terminal 28 amino acid tag containing myc epitope and hexa-histidine sequence.
[2]Wild-type NAAA with C-terminal 8 amino acid tag containing hexa-histidine sequence.
[3]To be determined. Polyclonal cell line in process of being grown at multi-liter scale Two non-catalytic cysteines (Cys103 and Cys113) in hNAAA were mutated to identify their importance either for structure (possible disulfide bond formation) or enzymatic activity. These cysteines are located on the α-chain, whereas catalytic Cys126 is at the N-terminus of the α-chain. The two mutants C103A and C113A were created by site-directed mutagenesis, and transfected into 293WT cells to produce stably transfected cell lines. The mutant enzymes were purified from the media in the same manner as NAAA-MH. Kinetic assays were performed to generate saturation curves with the fluorescence-based assay, and the Km and Vmax parameters for the mutants were found to be identical to wild-type enzyme (NAAA-MH), suggesting these cysteines are not critical to the structure or function of the enzyme. In addition, we tested the ability of several of our more potent isothiocyanate inhibitors to inhibit the mutant enzymes. Our hypothesis was that these compounds could covalently react with these cysteines in order to produce their inhibitory effect, as we know they do not react with Cys126 (based on massspectrometric and kinetic assay experimental evidence). However, we determined that the level of inhibition of C103A and C113A by the isothiocyanate compounds was identical to that of the wild-type enzyme, providing further evidence that the isothiocyanate compounds are reversible, competitive inhibitors that bind in the enzyme active site.

Example 119

Evaluation of NAAA inhibition of Test Compounds
NAAA Assay: In order to have an assay method more conducive to high-throughput screening than those published for measuring the NAE hydrolyzing activity of NAAA, we developed the fluorogenic PEA analog N-(4-methyl coumarin)palmitamide (PAMCA), which is hydrolyzed to fluorescent 7-amino-4-methyl coumarin (AMC) and palmitic acid. For three point concentration inhibition assays with hNAAA the following procedure is used. Purified activated NAAA (final concentration of 0.25 µg/mL) is incubated in assay buffer (100 mM citrate-phosphate buffer, pH 4.5, 3 mM DTT, 0.1% Triton X-100, 0.05% BSA, and 150 mM NaCl) made up to a total volume of 180 µL, followed by addition of the compound dissolved in 10 µL DMSO (along with DMSO neat for the control sample) with the final concentrations for each compound of 100, 10, and 1 µM, in triplicate on a 96 well plate. These samples are allowed to incubate for 15 min at room temperature and then 10 µL of a PAMCA stock solution in DMSO (final PAMCA concentration [5 µM]) was added. After 5 minutes of agitation on a shaking plate, the reaction is allowed to proceed at 37° C. for 120 minutes, with fluorescence readings taken every 10 minutes at a wavelength of 460 nm (using an excitation wavelength of 360 nm) on a Synergy HT Plate Reader using Gen5 software from Bio-Tek. The enzyme activity is calculated by converting the relative fluorescence units to AMC formed, using a standard curve of AMC. For compounds that inhibit hNAAA in range $IC_{50}$ <1 µM full inhibition curves using eight different concentrations of inhibitor (8 point assay) are generated. The assay procedure used is the same as the three point assay. For ostensibly covalent compounds (as observed by a significant decrease in the slope of a plot of fluorescence vs. time in three point screen) samples are allowed to incubate for 2 hours at 37° C., instead of 15 minutes, before addition of 10 µL of a PAMCA stock solution in DMSO for a final PAMCA concentration of 5 µM. After 5 minutes of agitation on a shaking plate, the reaction is allowed to proceed at 37° C. for 120 minutes Inhibition constants are calculated using pro Fit software (Quantum Soft, Uetikon am See, Switzerland) and a Levenberg-Marquardt algorithm.

In order to have an assay method more conducive to high-throughput screening than those published for measuring the NAE hydrolyzing activity of NAAA [Proc. Natl. Acad. Sci. USA. 2009; 106(49):20966-71], we developed the fluorogenic PEA analog N-(4-methyl coumarin)palmitamide (PAMCA), which is hydrolyzed to fluorescent 7-amino-4-methyl coumarin (AMC) and palmitic acid. [J. Proteome Res. 2012; 11(2):972-981], [PloS One. 2012; 7: e43877]. For three point concentration inhibition assays with hNAAA the following procedure is used. Purified activated NAAA (final concentration of 0.25 µg/mL) is incubated in assay buffer (100 mM citrate-phosphate buffer, pH 4.5, 3 mM DTT, 0.1% Triton X-100, 0.05% BSA, and 150 mM NaCl) made up to a total volume of 180 µL, followed by addition of the compound dissolved in 10 µL DMSO (along with DMSO neat for the control sample) with the final concentrations for each compound of 100, 10, and 1 µM, in triplicate on a 96 well plate. These samples are allowed to incubate for 15 min at room temperature and then 10 µL of a PAMCA stock solution in DMSO (final PAMCA concentration [5 µM]) was added. After 5 minutes of agitation on a shaking plate, the reaction is allowed to proceed at 37° C. for 120 minutes, with fluorescence readings taken every 10 minutes at a wavelength of 460 nm (using an excitation wavelength of 360 nm) on a Synergy HT Plate Reader using Gen5 software from Bio-Tek. The enzyme activity is calculated by converting the relative fluorescence units to AMC formed, using a standard curve of AMC.

For compounds that inhibit hNAAA in range $IC_{50}$ <1 µM full inhibition curves using eight different concentrations of inhibitor (8 point assay) are generated. The assay procedure used is the same as the three point assay. For ostensibly covalent compounds (as observed by a significant decrease in the slope of a plot of fluorescence vs. time in three point screen) samples are allowed to incubate for 2 hours at 37° C., instead of 15 minutes, before addition of 10 µL of a PAMCA stock solution in DMSO for a final PAMCA concentration of 5 µM. After 5 minutes of agitation on a shaking plate, the reaction is allowed to proceed at 37° C. for 120 minutes. Inhibition constants are calculated using pro Fit software (Quantum Soft, Uetikon am See, Switzerland) and a Levenberg-Marquardt algorithm.

The $k_{inact}$ and $K_I$ are routinely determined for the more potent ($IC_{50}$<10 nM) covalent inhibitors. This fluorescence-based assay is performed in a similar manner to the eight point assay as above with the following exceptions noted here. The concentration range of compound used is 1 to 100 nM, and the compound is mixed with the PAMCA substrate (final concentration of 12.4 µM=2×$K_m$) on the 96 well plate and incubated for 15 minutes at 37° C. Then the enzyme in assay buffer (warmed to 37° C.) is added to the wells containing the compound and substrate, vigorously shaken for 5 seconds, and fluorescence readings initiated immediately (data collected for 30 minutes at 60 second intervals). The data for each inhibitor concentration are fit to a first order equation (Eq. 1) shown below in order to determine $k_{observed}$ ($k_{obs}$), where $F_t$ is the fluorescence at time t, $F_0$ is the fluorescence at t=infinite time, $F_1$ is the total fluorescence change, and $k_{obs}$ is the first order rate constant for enzyme inactivation. To determine the inhibitor dissociation constant ($K_I$) and the first order rate constant for enzyme inactivation at infinite inhibitor concentration ($k_{inact}$), the $k_{obs}$ values for each [I] obtained above were fit to a curve us according to Eq. 2, which simplifies to Eq. 3 at [S]=2×$K_m$ as used in this experiment. These curves were fit using pro Fit software (Quantum Soft, Uetikon am See, Switzerland) and a Levenberg-Marquardt algorithm.

$$F_t = F_0 - F_1 e^{-k_{obs} t} \quad [1]$$

$$k_{obs} = \frac{k_{inact}[I]}{[I] + K_I\left(1 + \frac{[S]}{K_m}\right)} \quad [2]$$

$$k_{obs} = \frac{k_{inact}[I]}{[I] + 3(K_I)} \quad [3]$$

For Table 2 the NAAA inhibition as $IC_{50}$ μM index is as follow:
A=0.01 μM-0.1 μM
B=0.11 μM-1.00 μM
C=>1.00 μM

| Example No. | NAAA Inhibition $IC_{50}$ μM |
|---|---|
| 1 | C |
| 2 | C |
| 3 | C |
| 4 | A |
| 5 | C |
| 6 | C |
| 7 | C |
| 8 | C |
| 9 | C |
| 10 | C |
| 11 | C |
| 12 | C |
| 13 | C |
| 14 | C |
| 15 | C |
| 16 | C |
| 17 | C |
| 18 | A |
| 19 | A |
| 20 | A |
| 21 | A |
| 22 | A |
| 23 | A |
| 24 | A |
| 25 | A |
| 26 | A |
| 27 | A |
| 28 | B |
| 29 | A |
| 30 | C |
| 31 | B |
| 32 | B |
| 33 | A |
| 34 | C |
| 35 | A |
| 36 | A |
| 37 | B |
| 38 | A |
| 39 | A |
| 40 | A |
| 41 | B |
| 42 | A |
| 43 | C |
| 44 | B |
| 45 | C |
| 46 | B |
| 47 | A |
| 48 | A |
| 49 | B |
| 50 | C |
| 51 | A |
| 52 | A |
| 53 | C |
| 54 | C |
| 55 | C |
| 56 | B |
| 57 | B |
| 58 | C |
| 59 | B |
| 60 | C |
| 61 | C |
| 62 | C |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | B |
| 105 | A |
| 106 | C |
| 107 | C |
| 108 | C |
| 109 | C |
| 110 | C |
| 111 | C |
| 112 | C |
| 113 | C |
| 114 | C |
| 115 | B |
| 116 | C |
| 117 | C |

Example 120

Figure 2:
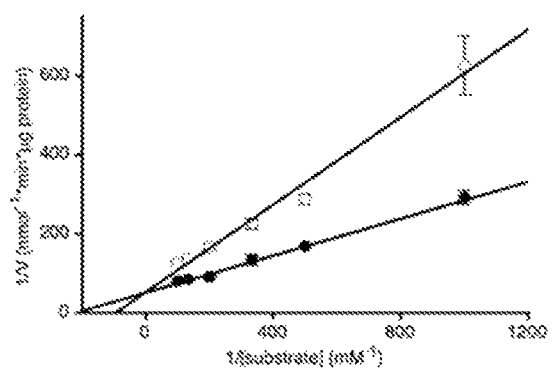
FIG. 2 shows the Lineweaver-Burk plot analysis of 4 inhibition of hNAAA. hNAAA was incubated with the fluorogenic substrate PAMCA at different concentrations in the absence (closed circles) and presence (open circles) of 4 at a concentration of 50 nM. The intersection of the lines at x=0 is indicative of a competitive inhibitor.

Example 4 inhibition kinetics of hNAAA (reversible or irreversible) was investigated using two methods: (1) Short (15 min) and long (180 min) pre-incubation of the inhibitor and enzyme prior to addition of N-(4-methyl coumarin) palmitamide (PAMCA) substrate (FIG. 1). Example's 4 inhibition concentration ($IC_{50}$) was unaffected by longer pre-incubation of hNAAA with 4. The profile of a Lineweaver-Burk (double reciprocal) plot suggested it was a competitive type inhibitor (FIG. 2); (2) Rapid dilution experiments of inhibited by Example 4 enzyme to a concentration of inhibitor bellow $IC_{50}$ to assess the recovery of the enzyme activity. The enzyme activity was fully recovered in a rapid dilution experiment indicative of ligand reversibility upon binding with the enzyme. These results suggested that compound of Example 4 was a reversible and non-covalent inhibitor of NAAA.

Example 121

Applicants also studied the compound of Example 4 in animal models of trinitrobenzene sulfonic acid (TNBS)- and dextran sodium sulfate (DSS)-induced colitis. This study aimed to investigate the effects of inhibiting NAAA responsible for PEA hydrolysis in colon inflammation in order to propose a potential therapeutic target for inflammatory bowel diseases. PEA is a known anti-inflammatory compound with analgesic, neuroprotective and anti-allergic properties, and was recently shown to exert PPARα dependent beneficial effects on colon inflammation [Laboratory Investigation; a Journal of Technical Methods and Pathology. 2004; 84: 1643-54].

Figure 3:
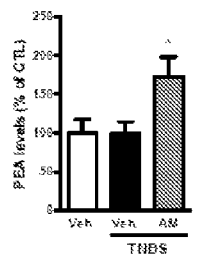
FIG. 3 shows the PEA levels in the colon of mice with TNBS-induced colitis. NAAA inhibitor Example 4 (10 mg/kg bid, ip) *p<0.05 versus the TNBS untreated group.
Figure 4:
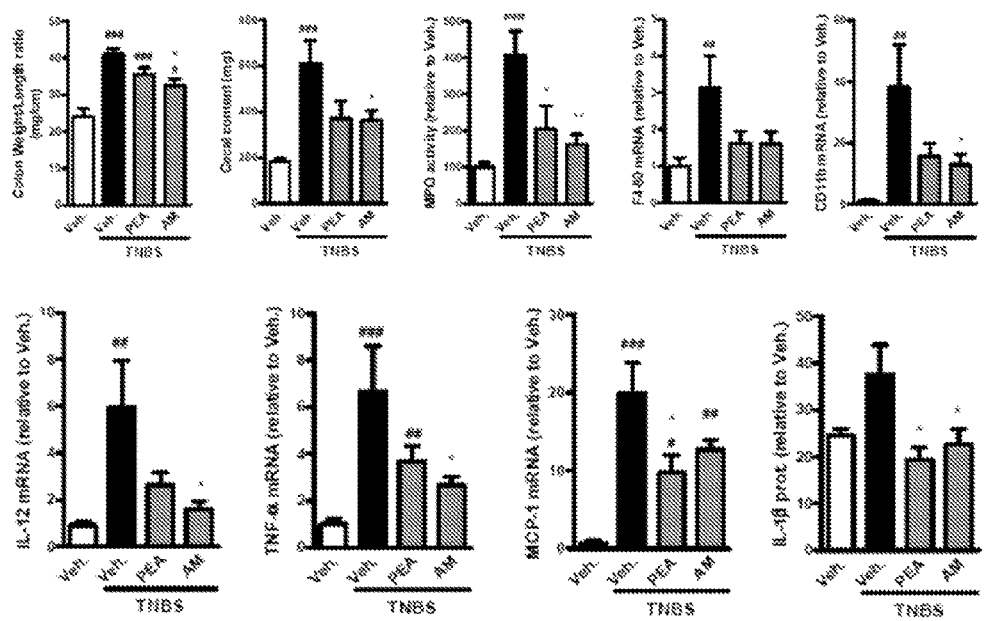
FIG. 4 shows the effects of PEA administration and NAAA inhibition on colon inflammation in TNBS-induced colitis. PEA (10 mg/kg) and NAAA inhibitor Example 4 (AM; 10 mg/kg bid, ip). Mice were sacrificed on day 3 after administration. Effects of PEA and Example 4 on colon weight/length ratio, feces and MPO activity, mRNA expression of F4-80, CD11b, IL-12, TNF-α, MCP-1 and IL-1β expression measured by ELISA. #p<0.05; ##p<0.005; ###p<0.001 versus control mice; *p<0.05 versus the TNBS-untreated group.

Administration of NAAA inhibitor Example 4 increased PEA levels (FIG. 3) in the colon and decreased all the measured parameters of colon inflammation. NAAA inhibition reduced the colon weight/length ratio and weight of the cecal content, leukocyte infiltration and activation measured by MPO activity and F4-80 and CD11b expression, and the expression of pro-inflammatory cytokines and chemokine's (FIG. 4).

Figure 5:
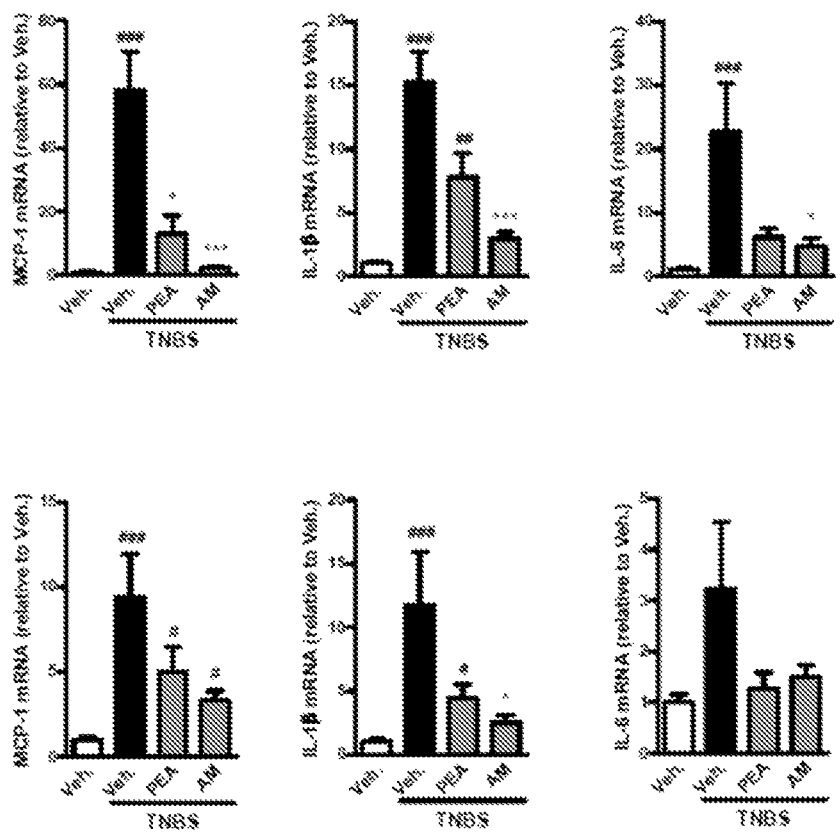
FIG. 5 shows the effects of PEA administration and NAAA inhibition on systemic inflammation resulting from TNBS-induced colitis. TNBS-induced colitis is accompanied by increased pro-inflammatory cytokines expression in the liver and brain. Effects of PEA administration and NAAA inhibition with Example 4 (10 mg/kg b.i.d) on pro-inflammatory cytokines expression in (A) the liver and (B) brain. Results are expressed as mean±SEM with n=10mice/group. *p<0.05; p<0.005; *p<0.001 versus the TNBS untreated group.

NAAA inhibition with compound of Example 4 also decreased pro-inflammatory cytokines and chemokines expression in the liver and brain (FIG. 5).

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology may be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like, include the number recited and refer to ranges which may be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound of Formula II, a tautomer thereof, a stereoisomer thereof, or a pharmaceutically acceptable salt thereof:

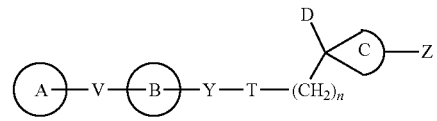

Formula II wherein:
Z is CN or —CH$_2$-CN; and
C is

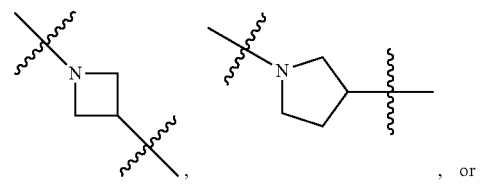

, or

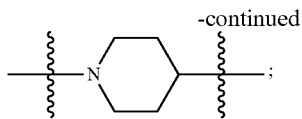

or

Z is NCS; and

C is a substituted or unsubstituted cyclobutyl, cyclopentyl, cyclohexyl, or

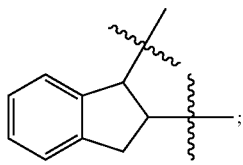 [SMILES: *C1Cc2ccccc2C1*]

and

D is hydrogen, $C_1$-$C_3$ alkyl, aryl, or heteroaryl;

T is O or $NR^1$, wherein $R^1$ is H or $C_1$-$C_3$ alkyl;

Y is absent or $C_1$-$C_3$ alkylene;

B is a substituted or unsubstituted 5-10 membered aryl or heteroaryl;

V is absent or O;

A is a substituted or unsubstituted 5-10 membered aryl or heteroaryl; and n is 0, 1, 2, or 3, wherein A, B and C, when substituted, are each independently substituted with one or more substituent groups selected from halogen, hydroxyl, alkoxy, alkenoxy, aryloxy, aralkyloxy, heterocyclyl, heterocyclylalkyl, heterocyclyloxy, heterocyclylalkoxy, carbonyl, carboxylate, ester, urethane, oxime, hydroxylamine, alkoxyamine, aralkoxyamine, thiol, sulfide, sulfoxide, sulfone, sulfonyl, pentafluorosulfanyl, sulfonamide, amine, N-oxide, hydrazine, hydrazide, hydrazone, azide, amide, urea, amidine, guanidine, enamine, imide, isocyanate, isothiocyanate, cyanate, thiocyanate, imine, nitro, nitrile or alkyl optionally substituted one or more times with halo, hydroxy, thio, amino, alkylamino, dialkylamino, alkoxy or carboxy.

2. The compound of claim 1, wherein C is

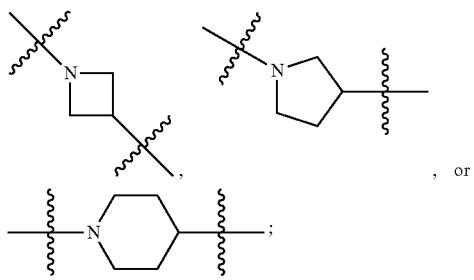

and Z is CN or —$CH_2$—CN.

3. The compound of claim 1, wherein C is a substituted or unsubstituted cyclobutyl, cyclopentyl, cyclohexyl, or

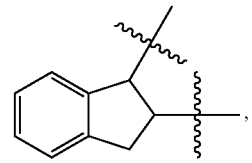 [SMILES: *C1Cc2ccccc2C1*]

and Z is NCS.

4. The compound of claim 1, wherein B is phenyl.

5. The compound of claim 1, wherein B is substituted phenyl.

6. The compound of claim 1, wherein n is 0.

7. A compound selected from the group consisting of:
4-(((1R,3R)-3-isothiocyanatocyclobutoxy)methyl)-4'-methyl-1,1'-biphenyl;
4-(((1S,3S)-3-isothiocyanatocyclobutoxy)methyl)-4'-methyl-1,1'-biphenyl;
4-(((1R,3R)-3-isothiocyanatocyclobutoxy)methyl)-1,1'-biphenyl;
4-(((1S,3S)-3-isothiocyanatocyclobutoxy)methyl)-1,1'-biphenyl;
3,4'-difluoro-4-(((1S,3S)-3-isothiocyanatocyclobutoxy)methyl)-1,1'-biphenyl;
3,3'-difluoro-4-(((1S,3S)-3-isothiocyanatocyclobutoxy)methyl)-4'-methoxy-1,1'-biphenyl;
4'-(((1R,3R)-3-isothiocyanatocyclobutoxy)methyl)-3-methoxy-1,1'-biphenyl;
4'-(((1S,3S)-3-isothiocyanatocyclobutoxy)methyl)-3-methoxy-1,1'-biphenyl;
4-ethoxy-3,3'-difluoro-4'-(((1S,3S)-3-isothiocyanatocyclobutoxy)methyl)-1,1'-biphenyl;
3,3'-difluoro-4-isopropoxy-4'-(((1S,3S)-3-isothiocyanatocyclobutoxy)methyl)-1,1'-biphenyl;
6-(3-fluoro-4-(((1S,3S)-3-isothiocyanatocyclobutoxy)methyl)phenyl)-2,3-dihydrobenzo[b][1,4]dioxine;
5-(3-fluoro-4-(((1S,3S)-3-isothiocyanatocyclobutoxy)methyl)phenyl)benzo[d][1,3]dioxole;
3-fluoro-4-(((1S,3S)-3-isothiocyanatocyclobutoxy)methyl)-3',4'-dimethoxy-1,1'-biphenyl;
3-(3-fluoro-4-(((1R,3R)-3-isothiocyanatocyclobutoxy)methyl)phenyl)-2-methoxypyridine;
5-(3-fluoro-4-methoxyphenyl)-2-(((1R,3R)-3-isothiocyanatocyclobutoxy)methyl)pyridine;
3,4'-difluoro-3'-(((1S,3S)-3-isothiocyanatocyclobutoxy)methyl)-4-methoxy-1,1'-biphenyl;
4-(3-fluoro-4-(((1R,3R)-3-isothiocyanatocyclobutoxy)methyl)phenyl)-3,5-dimethylisoxazole;
4-(3-fluoro-4-(((1R,3R)-3-isothiocyanatocyclobutoxy)methyl)phenyl)-1-methyl-1H-pyrazole;
3-fluoro-4-(((1R,3R)-3-isothiocyanatocyclobutoxy)methyl)-3'-(trifluoromethyl)-1,1'-biphenyl;
3'-(benzyloxy)-3-fluoro-4-(((1R,3R)-3-isothiocyanatocyclobutoxy)methyl)-1,1'-biphenyl;
2-bromo-1-(((1S,3S)-3-isothiocyanatocyclobutoxy)methyl)-4-phenoxybenzene;
2-(((1S,3S)-3-isothiocyanatocyclobutoxy)methyl)-5-phenoxy-1,1'-biphenyl;
3-fluoro-4'-((1R,3R)-3-isothiocyanatocyclobutoxy)-4-methoxy-1,1'-biphenyl;
3-fluoro-4'-((1S,3S)-3-isothiocyanatocyclobutoxy)-4-methoxy-1,1'-biphenyl;
(1R,3R)—N-([1,1'-biphenyl]-4-ylmethyl)-3-isothiocyanato-N-methylcyclobutan-1-amine,
(1S,3S)—N-([1,1'-biphenyl]-4-ylmethyl)-3-isothiocyanato-N-methylcyclobutan-1-amine, (1R,3R)—N-(4-(benzo[d][1,3]dioxol-5-yl)benzyl)-3-iso-thiocyanato-N-methylcyclobutan-1-amine;
(1R,3R)—N-(4-(benzo[d][1,3]dioxol-5-yl)benzyl)-N-ethyl-3-isothiocyanatocyclobutan-1-amine;
4'-(((3-isothiocyanatocyclohexyl)oxy)methyl)-3-(trifluoromethyl)-1,1'-biphenyl;
3-fluoro-4'-((((1R,4R)-4-isothiocyanatocyclohexyl)oxy)methyl)-4-methoxy-1,1'-biphenyl;
(1R,2S)-1-isothiocyanato-2-((3'-(trifluoromethyl)-[1,1'-biphenyl]-4-yl)methoxy)-2,3-dihydro-1H-indene;
(1S,2R)-2-((3'-fluoro-4'-methoxy-[1,1'-biphenyl]-4-yl)methoxy)-1-isothiocyanato-2,3-dihydro-1H-indene;
3-((4'-methoxy-[1,1'-biphenyl]-4-yl)methoxy)azetidine-1-carbonitrile;
3-([1,1'-biphenyl]-4-ylmethoxy)azetidine-1-carbonitrile;
3-((2',4'-dimethoxy-[1,1'-biphenyl]-4-yl)methoxy)azetidine-1-carbonitrile;
3-([1,1'-biphenyl]-3-ylmethoxy)azetidine-1-carbonitrile;
3-((3'-methoxy-[1,1'-biphenyl]-4-yl)methoxy)azetidine-1-carbonitrile;
3-((2',5'-dimethoxy-[1,1'-biphenyl]-4-yl)methoxy)azetidine-1-carbonitrile;
3-((2',3'-dimethoxy-[1,1'-biphenyl]-4-yl)methoxy)azetidine-1-carbonitrile;
3-((3'-(trifluoromethyl)-[1,1'-biphenyl]-4-yl)methoxy)azetidine-1-carbonitrile;
3-((3',5'-bis(trifluoromethyl)-[1,1'-biphenyl]-4-yl)methoxy)azetidine-1-carbonitrile;
3-((4-(pyridin-3-yl)benzyloxy)azetidine-1-carbonitrile;
3-((4-(6-methoxypyridin-3-yl)benzyl)oxy)azetidine-1-carbonitrile;
3-((4-(2-methoxypyridin-3-yl)benzyl)oxy)azetidine-1-carbonitrile;
3-((2'-methoxy-[1,1'-biphenyl]-4-yl)methoxy)azetidine-1-carbonitrile;
3-((4'-methyl-[1,1'-biphenyl]-4-yl)methoxy)azetidine-1-carbonitrile;
3-((4'-fluoro-[1,1'-biphenyl]-4-yl)methoxy)azetidine-1-carbonitrile;
3-((3-fluoro-3'-methoxy-[1,1'-biphenyl]-4-yl)methoxy)azetidine-1-carbonitrile;
3-((3'-methoxy-3-(trifluoromethyl)-[1,1'-biphenyl]-4-yl)methoxy)azetidine-1-carbonitrile;
3-((3,3'-dimethoxy-[1,1'-biphenyl]-4-yl)methoxy)azetidine-1-carbonitrile;
3-((4-phenoxybenzyl)oxy)azetidine-1-carbonitrile;
3-((2',6'-dimethoxy-[1,1'-biphenyl]-4-yl)methoxy)azetidine-1-carbonitrile;
3-((4-(2,3-dihydrobenzo[b][1,4]dioxin-6-yl)benzyl)oxy)azetidine-1-carbonitrile;
3-((3'-(benzyloxy)-[1,1'-biphenyl]-4-yl)methoxy)azetidine-1-carbonitrile;
3-(([1,1'-biphenyl]-4-ylmethoxy)methyl)azetidine-1-carbonitrile;
3-((5-phenoxy-[1,1'-biphenyl]-2-yl)methoxy)azetidine-1-carbonitrile;
3-((2'-methoxy-5-phenoxy-[1,1'-biphenyl]-2-yl)methoxy)azetidine-1-carbonitrile;
3-((3'-methoxy-5-phenoxy-[1,1'-biphenyl]-2-yl)methoxy)azetidine-1-carbonitrile;
3-((4'-methoxy-5-phenoxy-[1,1'-biphenyl]-2-yl)methoxy)azetidine-1-carbonitrile;
3-((2-(2-methoxypyridin-3-yl)-4-phenoxybenzyl)oxy)azetidine-1-carbonitrile;
3-((4'-cyano-5-phenoxy-[1,1'-biphenyl]-2-yl)methoxy)azetidine-1-carbonitrile;
3-((2'-cyano-5-phenoxy-[1,1'-biphenyl]-2-yl)methoxy)azetidine-1-carbonitrile;
3-((3'-methoxy-[1,1'-biphenyl]-4-yl)methoxy)-3-methylazetidine-1-carbonitrile;
3-((3'-methoxy-[1,1'-biphenyl]-4-yl)methoxy)-3-phenylazetidine-1-carbonitrile;
3-((4-(benzo[d][1,3]dioxol-5-yl)benzyl)oxy)-3-phenylazetidine-1-carbonitrile;
3-((4-(2,3-dihydrobenzo[b][1,4]dioxin-6-yl)benzyl)oxy)-3-phenylazetidine-1-carbonitrile;
3-(([1,1'-biphenyl]-4-ylmethyl)(methyl)amino)azetidine-1-carbonitrile;
(S)-3-([1,1'-biphenyl]-4-ylmethoxy)pyrrolidine-1-carbonitrile;
(R)-3-([1,1'-biphenyl]-4-ylmethoxy)pyrrolidine-1-carbonitrile;
(1R,3R)-3-([1,1'-biphenyl]-4-ylmethoxy)cyclobutane-1-carbonitrile;
(1S,3S)-3-([1,1'-biphenyl]-4-ylmethoxy)cyclobutane-1-carbonitrile;
2-(3-((3'-methoxy-[1,1'-biphenyl]-4-yl)methoxy)azetidin-1-yl)acetonitrile;
5-((2-bromo-4-phenoxybenzyl)oxy)picolinonitrile;
5-([1,1'-biphenyl]-4-ylmethoxy)picolinonitrile;
5-([1,1'-biphenyl]-4-ylmethoxy)-3-fluoropicolinonitrile; and
3-([1,1'-biphenyl]-4-ylmethoxy)-5-fluoropicolinonitrile;
or
a tautomer thereof;
a stereoisomer thereof; or
a pharmaceutically acceptable salt thereof.

8. A composition comprising a compound of claim 1, or a pharmaceutically acceptable salt thereof, and a pharmaceutically acceptable excipient.

9. A method for inhibiting N-acylethanolamine hydrolyzing acid amidase, the method comprising contacting the N-acylethanolamine hydrolyzing acid amidase with a compound of claim 1, or a pharmaceutically acceptable salt thereof.

10. A method for treating a N-acylethanolamine hydrolyzing acid amidase mediated condition in a subject, the method comprising administering to the subject a composition comprising an effective amount of a compound of claim 1, or a pharmaceutically acceptable salt thereof, and a pharmaceutically acceptable excipient.

11. A method of treating an inflammatory gastrointestinal motility disorder, irritable bowel syndrome, or an inflammatory bowel disorder in a subject in need thereof, the method comprising administering to the subject a therapeutically effective amount of a compound of claim 1, or a pharmaceutically acceptable salt thereof.

12. A method for treating ulcerative colitis in a patient in need thereof, the method comprising administering to the patient a therapeutically effective amount of the compound of claim 1, or a pharmaceutically acceptable salt thereof.

13. A method for treating Crohn's disease in a patient in need thereof, the method comprising administering to the patient a therapeutically effective amount of the compound of claim 1, or a pharmaceutically acceptable salt thereof.

14. A method for modulating the activity of N-acylethanolamine hydrolyzing acid amidase, the method comprising contacting a receptor thereof with an effective amount of the compound of claim 1, or a pharmaceutically acceptable salt thereof.

* * * * *

UNITED STATES PATENT AND TRADEMARK OFFICE
CERTIFICATE OF CORRECTION

PATENT NO. : 9,963,444 B2
APPLICATION NO. : 15/311817
DATED : May 8, 2018
INVENTOR(S) : Malamas et al.

Page 1 of 1

It is certified that error appears in the above-identified patent and that said Letters Patent is hereby corrected as shown below:

In the Specification

Column 1, Line 17 GOVERNMENT RIGHTS:
Delete "The United States Government has rights in this technology pursuant to Contract No. R01-DA003801 awarded by the National Institute of Health", and insert -- This invention was made with government support under Grant Number DA003801 awarded by the National Institutes of Health. The government has certain rights in the invention. --

Signed and Sealed this
Fourth Day of June, 2019

Andrei Iancu
*Director of the United States Patent and Trademark Office*